United States Patent
Davis et al.

(10) Patent No.: US 11,041,050 B2
(45) Date of Patent: *Jun. 22, 2021

(54) CATIONIC MUCIC ACID POLYMER-BASED DELIVERY SYSTEMS

(71) Applicant: California Institute Of Technology, Pasadena, CA (US)

(72) Inventors: Mark E. Davis, Pasadena, CA (US); Dorothy Pan, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/880,065

(22) Filed: May 21, 2020

(65) Prior Publication Data

US 2020/0283582 A1 Sep. 10, 2020

Related U.S. Application Data

(63) Continuation of application No. 16/351,168, filed on Mar. 12, 2019, now Pat. No. 10,717,825, which is a continuation of application No. 15/180,201, filed on Jun. 13, 2016, now Pat. No. 10,287,401.

(60) Provisional application No. 62/187,366, filed on Jul. 1, 2015.

(51) Int. Cl.
| | |
|---|---|
| C08G 81/00 | (2006.01) |
| A61K 47/34 | (2017.01) |
| C08G 69/40 | (2006.01) |
| C08G 79/08 | (2006.01) |
| C08G 73/02 | (2006.01) |
| C08J 3/12 | (2006.01) |
| A61K 9/50 | (2006.01) |

(52) U.S. Cl.
CPC ............ *C08G 81/00* (2013.01); *A61K 9/5031* (2013.01); *A61K 47/34* (2013.01); *C08G 69/40* (2013.01); *C08G 73/028* (2013.01); *C08G 79/08* (2013.01); *C08J 3/12* (2013.01)

(58) Field of Classification Search
CPC ...... C08G 81/00; C08G 73/028; C08G 79/08; C08G 69/40; A61K 9/5031; A61K 47/34; C08J 3/12
See application file for complete search history.

(56) References Cited

U.S. PATENT DOCUMENTS

| | | |
|---|---|---|
| 4,631,190 A | 12/1986 | Shen et al. |
| 5,217,999 A | 6/1993 | Levitzki et al. |
| 5,302,606 A | 4/1994 | Spada et al. |
| 5,330,992 A | 7/1994 | Eissenstat et al. |
| 5,457,105 A | 10/1995 | Barker |
| 5,578,325 A | 11/1996 | Domb et al. |
| 5,596,878 A | 1/1997 | Hanson et al. |
| 5,616,582 A | 4/1997 | Barker |
| 5,693,631 A | 12/1997 | Whittemore et al. |
| 5,710,173 A | 1/1998 | Tang et al. |
| 5,747,498 A | 5/1998 | Schnur et al. |
| 5,770,599 A | 6/1998 | Gibson |
| 5,948,878 A | 9/1999 | Burgess et al. |
| 5,972,707 A | 10/1999 | Roy et al. |
| 6,007,845 A | 12/1999 | Domb et al. |
| 6,034,081 A | 3/2000 | Whittemore et al. |
| 6,048,736 A | 4/2000 | Kosak |
| 6,060,466 A | 5/2000 | Whittemore et al. |
| 6,225,346 B1 | 5/2001 | Tang et al. |
| 6,391,874 B1 | 5/2002 | Cockerill et al. |
| 6,596,878 B2 | 7/2003 | Chen et al. |
| 6,645,944 B2 | 11/2003 | Re et al. |
| 6,713,485 B2 | 3/2004 | Carter et al. |
| 6,716,863 B2 | 4/2004 | Tasaka et al. |
| 6,727,256 B1 | 4/2004 | Carter et al. |
| 6,828,320 B2 | 12/2004 | Cockerill et al. |
| 6,900,221 B1 | 5/2005 | Norris et al. |

(Continued)

FOREIGN PATENT DOCUMENTS

| | | |
|---|---|---|
| CN | 102123698 A | 7/2011 |
| JP | 2000-514440 | 10/2000 |

(Continued)

OTHER PUBLICATIONS

Adeli et al. "Tumor-targeted drug delivery systems based on supramolecular interactions between iron oxide-carbon nanotubes PAMAM-PEG-PAMAM linear-dendritic copolymers", J. Iran. Chem. Soc., 2013, 10, 701-708.

(Continued)

*Primary Examiner* — Robert S Cabral
(74) *Attorney, Agent, or Firm* — BakerHostetler

(57) ABSTRACT

The present disclosure is directed to nanoparticle delivery systems for delivering biological agents, pharmaceutical compositions of comprising these nanoparticles, and methods of using these compositions. Certain embodiments of the present disclosure provide nanoparticles comprising polymers comprising alternating charged and uncharged segments comprising one or more of the following structural units of Formula (I) Formula (III):

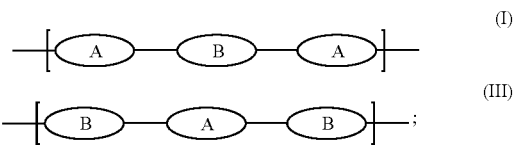

wherein A is an uncharged segment comprising polyalkylene glycol; and B is a cationically charged segment comprising at least one polyhydroxy linkage.

26 Claims, 25 Drawing Sheets

(56) References Cited

U.S. PATENT DOCUMENTS

| | | |
|---|---|---|
| 6,984,653 B2 | 1/2006 | Tasaka et al. |
| 7,018,609 B2 | 3/2006 | Hwang et al. |
| 7,087,613 B2 | 8/2006 | Norris et al. |
| 7,091,192 B1 | 8/2006 | Davis et al. |
| 7,094,427 B2 | 8/2006 | Han et al. |
| 7,157,466 B2 | 1/2007 | McClure et al. |
| 7,166,302 B2 | 1/2007 | Hwang et al. |
| 7,270,808 B2 | 9/2007 | Cheng et al. |
| 7,300,935 B2 | 11/2007 | Cho et al. |
| 7,427,605 B2 | 9/2008 | Davis et al. |
| RE41,065 E | 12/2009 | Schnur et al. |
| 8,367,116 B2 | 2/2013 | Pratt et al. |
| 8,367,166 B2 | 2/2013 | Dahl et al. |
| 8,377,474 B2 | 2/2013 | Hsu et al. |
| 8,557,292 B2 | 10/2013 | Davis et al. |
| 8,746,999 B2 | 6/2014 | Davis et al. |
| 8,968,714 B2 | 3/2015 | Davis et al. |
| 9,132,097 B2 | 9/2015 | Davis et al. |
| 9,186,327 B2 | 11/2015 | Davis et al. |
| 9,334,367 B2 | 5/2016 | Davis et al. |
| 9,468,681 B2 | 10/2016 | Davis et al. |
| 9,610,355 B2 | 4/2017 | Davis et al. |
| 9,913,911 B2 | 3/2018 | Davis et al. |
| 10,155,051 B2 | 12/2018 | Davis et al. |
| 10,287,401 B2 | 5/2019 | Davis et al. |
| 2002/0054902 A1 | 5/2002 | Pardridge |
| 2002/0061288 A1 | 5/2002 | Hubbell et al. |
| 2003/0055212 A1 | 3/2003 | Freund et al. |
| 2003/0059399 A1 | 3/2003 | Holmes-Farley et al. |
| 2003/0147966 A1 | 8/2003 | Franzen et al. |
| 2004/0023334 A1 | 2/2004 | Prior |
| 2004/0126838 A1 | 7/2004 | Defrees et al. |
| 2004/0220146 A1 | 11/2004 | Freeman et al. |
| 2005/0090732 A1 | 4/2005 | Ivkov et al. |
| 2005/0148607 A1 | 7/2005 | Suzuki et al. |
| 2006/0055069 A1 | 3/2006 | Dimatteo et al. |
| 2006/0078997 A1 | 4/2006 | Lugade et al. |
| 2006/0134062 A1 | 6/2006 | Huval et al. |
| 2006/0153907 A1 | 7/2006 | Zalipsky et al. |
| 2006/0159736 A1 | 7/2006 | Zalipsky et al. |
| 2006/0246524 A1 | 11/2006 | Bauer et al. |
| 2006/0263435 A1 | 11/2006 | Davis et al. |
| 2008/0099172 A1 | 5/2008 | Pelton et al. |
| 2008/0214584 A1 | 9/2008 | Ohta et al. |
| 2009/0169638 A1 | 7/2009 | Davis et al. |
| 2009/0281024 A1 | 11/2009 | Zankel et al. |
| 2010/0029545 A1 | 2/2010 | Sumerlin et al. |
| 2010/0040556 A1 | 2/2010 | Davis et al. |
| 2010/0069500 A1 | 3/2010 | Dhal et al. |
| 2010/0166865 A1 | 7/2010 | Kumar et al. |
| 2010/0303850 A1 | 12/2010 | Lipford et al. |
| 2010/0309691 A1 | 12/2010 | Baptiste et al. |
| 2010/0330686 A1 | 12/2010 | Park |
| 2011/0086431 A1 | 4/2011 | Lugade et al. |
| 2012/0225129 A1 | 9/2012 | Eliasof et al. |
| 2012/0259021 A1 | 10/2012 | Jiang et al. |
| 2012/0309691 A1 | 12/2012 | Zhou et al. |
| 2012/0328564 A1 | 12/2012 | Govindan et al. |
| 2014/0249202 A1 | 9/2014 | Davis et al. |
| 2014/0249203 A1 | 9/2014 | Davis et al. |
| 2014/0348754 A1 | 11/2014 | Wiley et al. |
| 2015/0045419 A1 | 2/2015 | Lam et al. |
| 2015/0376237 A1 | 12/2015 | Borros et al. |
| 2016/0000934 A1 | 1/2016 | Davis et al. |
| 2017/0071857 A1 | 3/2017 | Wiley et al. |

FOREIGN PATENT DOCUMENTS

| | | |
|---|---|---|
| JP | 2004-525858 A | 11/2001 |
| JP | 2005-511761 | 4/2005 |
| JP | 2005-119255 | 5/2005 |
| JP | 2008-512640 | 4/2008 |
| JP | 2008-516240 A | 5/2008 |
| JP | 2010-501004 A | 5/2008 |
| JP | 2009-508494 | 3/2009 |
| JP | 2012-500208 A | 1/2012 |
| JP | 2014-514431 A | 6/2014 |
| WO | 91/15495 A1 | 10/1991 |
| WO | 92/20642 A1 | 11/1992 |
| WO | 92/21660 A1 | 12/1992 |
| WO | 94/03427 A1 | 2/1994 |
| WO | 94/14808 A1 | 7/1994 |
| WO | 96/00226 A1 | 1/1996 |
| WO | 97/13771 A1 | 4/1997 |
| WO | 97/47658 A1 | 12/1997 |
| WO | 98/02437 A1 | 1/1998 |
| WO | 99/10022 A2 | 3/1999 |
| WO | 00/10007 A2 | 2/2000 |
| WO | 00/44728 A1 | 8/2000 |
| WO | 01/01921 A1 | 1/2001 |
| WO | 01/77107 A1 | 10/2001 |
| WO | 01/82900 A1 | 11/2001 |
| WO | 01/98277 A2 | 12/2001 |
| WO | 01/98299 A1 | 12/2001 |
| WO | 02/02552 A1 | 1/2002 |
| WO | 03/00688 A1 | 1/2003 |
| WO | 03/31442 A1 | 4/2003 |
| WO | 03/49740 A1 | 6/2003 |
| WO | 03/50108 A1 | 6/2003 |
| WO | 03/53446 A1 | 7/2003 |
| WO | 2005/119255 A2 | 12/2005 |
| WO | 2007/034479 A2 | 3/2007 |
| WO | 2007/061919 A2 | 5/2007 |
| WO | 2008/011561 A2 | 1/2008 |
| WO | 2008/060734 A2 | 5/2008 |
| WO | 2009/036022 A1 | 3/2009 |
| WO | 2010/019718 A2 | 2/2010 |
| WO | 2010/120262 A1 | 10/2010 |
| WO | 2011/072133 A1 | 6/2011 |
| WO | 2011/159161 A2 | 12/2011 |
| WO | 2012/079047 A2 | 6/2012 |
| WO | 2012/158622 A2 | 11/2012 |
| WO | 2014/033549 A2 | 3/2014 |
| WO | 2014/133547 A1 | 9/2014 |
| WO | 2014/133549 A1 | 9/2014 |
| WO | 2014/185964 A1 | 11/2014 |
| WO | 2016/037166 A1 | 3/2016 |
| WO | 2017/003668 A1 | 1/2017 |

OTHER PUBLICATIONS

Adkins et al., "NKTR-102 efficacy versus irinotecan in a mouse model of brain metastases of breast cancer", BMC Cancer, 2015, 15, 685.

Allen, T.M. Ligand-Targeted Therapeutics in Anticancer Therapy. Nature Reviews, vol. 2, pp. 750-763, Oct. 2002.

Andrew James Clark. "Delivery of Targeted Nanoparticles Across the Blood-Brain Barrier Using a Detachable Targeting Ligand." California Institute of Technology, PhD Thesis, 2016, pp. i-xxiii and 1-177 (200 total sheets). (Year: 2016).

Armstrong et al., "The Hydrodynamic Radii of Macromolecules and Their Effect on Red Blood Cell Aggregation", Biophysical Journal, 2004, 87(6), 4259-4270.

Aversa et al., "Metastatic breast cancer subtypes and central nervous system metastases", Breast, 2014, 23, 623-628.

Ballarin-Gonzalez et al. "Polycation-based nanoparticle delivery of RNAi therapeutics: Adverse effects and solutions", Advanced Drug Delivery Reviews, 2012, 64, 1717-1729.

Bao et al., "0X26 modified hyperbranched polyglycerol-conjugated poly(lactic-co-glycolic acid) nanoparticles: Synthesis, characterization and evaluation of its brain delivery ability", Journal of Materials Science: Materials in Medicine, May 9, 2012, vol. 23, No. 8, 1891-1901.

Barnholtz-Sloan et al., "Incidence Proportions of Bain Metastases in patients diagnosed (1973 to 2001) in the Metropolitan Detroit Center Surveillance System", J. Clin. Oncol., 2004, 22, 2865-2872.

Barros et al., "Safety profile of RNAi nanomedicines", Advanced Drug Delivery Reviews, 2012,64, 1730-1737.

Bartlett et al., "Physicochemical and Biological Characterization of Targeted, Nucleic Acid-Containing Nanoparticles", Bioconjugate Chemistry, 2007, 18, 456-468.

(56) References Cited

OTHER PUBLICATIONS

Bellocq et al., "Transferrin-Containing Cyclodextrin Polymer-Based Particles for Tumor-Targeted Gene Delivery", Bioconjug Chem, 2003, 14, 1122-1132.
Bohn et al., "Semi-automated rapid quantification of brain vessel density using fluorescent microscopy", J. Neurosci. Methods, 2016, 270, 124-131.
Brissault et al., "Synthesis of poly(propylene glycol)-block-polyethylenimine tri block copolymers for the delivery of nucleic acids", Macromol. Biosci., 2012, 11, 652-661.
Chang et al., "Characterization of endocytosis of transferrin-coated PLGA nano particles by the blood-brain barrier", International Journal of Pharmaceutics, Sep. 11, 2009, vol. 379, No. 2, 285-292.
Chen et al., "Modern Methods for delivery of drugs across the blood-brain barrier", Adv. Drug Deliv. Rev., 2012, 64, 640-665.
Choi et al., "Mechanism of active targeting in solid tumors with transferrin-containing gold nanoparticles", PNAS, Jan. 2010, 107(3), 1235-1240.
Christie et al., "Targeted polymeric micelles for siRNA treatment of experimental cancer by intravenous injection", ACS Nano., 2012, 6, 5174-5189.
Clark et al., "Increased brain uptake of targeted nanoparticles by adding an acid-cleavable linkage between transferrin and the nanoparticle core", Proc. Natl. Acad. Sci. USA, 2015, 112, 12486-12491.
Coderre et al., "The Radiation Biology of Boron Neutron Capture Therapy", Radiat Res, 1999, 151, 1-18.
D'Addio et al., "Effects of block copolymer properties on nanocarrier protection from in vivo clearance", Journal of Controlled Release, 2012, 162, 208-217.
Dautry-Varsat et al., "pH and the Recycling of Transferrin During Receptor-Mediated Endocytosis", P Natl Acad Sci, 1983, 80, 2258-2262.
Davis et al., "Evidence of RNAi in Humans from Systemically Administered siRNA Via Targeted Nanoparticles", Nature, 2010, 464, 1067-1070.
Davis et al., "Nanoparticle therapeutics: An emerging treatment modality for cancer", Nat. Rev. Drug Discov., Sep. 2008, 7, 771-782.
Davis et al., "The First Targeted Delivery of siRNA in Humans Via a Self-Assembling, Cyclodextrin Polymer-Based Nanoparticle: From Concept to Clinic", Molecular Pharmaceutics, 2009, 6, 659-668.
Duncan, R. Polymer conjugates as anticancer nanomedicines. Nature Reviews, vol. 6, pp. 688-701, Sep. 2006.
Friden et al., "Characterization, Receptor Mapping and Blood-Brain Barrier Transcytosis of Antibodies to the Human Transferrin Receptor", J Pharm Exp Ther, 1996, 278, 1491-1498.
Fujita, N. etal., Boronic Acids in Molecular Self-Assembly, Chem. Asian J., 2008, vol. 3, pp. 1076-1091.
Gallas et al., "Chemistry and formulations for siRNA therapeutics", Chem. Soc. Rev., 2012, 42, 7983-7997.
Georgieva et al., "Smuggling Drugs into the Brain: An Overview of Ligands Targeting Transcytosis for Drug Delivery Across the Blood Brain Barrier", Pharmaceutics, 2014, 6(4), 557-583.
Goldman, C.K. et al., "In Vitro and In Vivo Gene Delivery Mediated by a Synthetic Polycationic Amino Polymer", Nature, Biotechnology, May 1997, 15, 462-466.
Gomes-da-Silva et al., "Challenging the future of siRNA therapeutics against cancer: the crucial role of nanotechnology", Cell. Mol. Life. Sci., 2013, 71, 1417-1438.
Gosh, P., et al., "Gold nanoparticles in delivery applications", 2008, Adv., Drug Deliv. Rev., pp. 1307-1315.
Gu et al., "Cationic amphiphilic macromolecule (CAM)-lipid complexes for efficient siRNA gene silencing", Journal of Controlled Release, 2014, 184, 28-35.
Han et al., "Single-Antibody, Targeted Nanoparticle Delivery of Camptothecin", Molecular Pharmaceuticals, Jul. 1, 2013, vol. 10, No. 7, 2558-2567.

Han et al., "Targeted Nanoparticles Assembled via Complexation of Boronic-Acid-Containing Targeting Moieties to Dial-Containing Polymers", Bioconjugate Chemistry, Mar. 6, 2013, vol. 24, No. 4, 669-677.
Han et al., "Targeted polymer-based nanoparticles containing camptothecin: Development and function", American Association for Cancer Research, Apr. 15, 2012, vol. 72, Issue 8 Supplement, 1-2.
Han, Development of targeted, polymeric delivery vehicles for camptothecin and siRNA via boronic acid-diol complexation, Han han, Thesis (Dissertation Ph.D) of California Institute of Technology, pp. 125-128,2013.
Hanmei Bao et al: "OX26 modified hyperbranched polyglycerolconjugated poly(lactic-glycolic acid) nanoparticles: synthesis, characterization and evaluation of its brain delivery ability", Journal of Materials Science: Materials in Medicine, Kluwer Academic Publishers, BO, vol. 23, No. 8, May 9, 2012 (May 9, 2012), pp. 1891-1901.
Hou et al., "Development of Zeptomole and Attomolar Detection Sensitivity of Biotin-Peptide Using a Dot-Blot GoldNanoparticle Immunoassay", Anal. Chem., 2007, 79(3), 980-985.
Jiang et al., "Nanoparticle-Mediated Cellular Response is Size-Dependent", Nature Nanotech, 2008, 3(3), 145-150.
Kale et. al., "Design, Synthesis, and Characterization of pH-Sensitive PEG-PE Conjugates for Stimuli-Sensitive Pharmaceutical Nanocarriers: The Effect of Substitutes at the Hydrazone Linkage on the pH Stability of PEG-PE Conjugates", Bioconjugate Chem. 2007, 18, 363-370.
Kamaly et al., "Targed Polymeric Therapeutic Nanoparticles: Design, Development and Clinical Translation", Chem Soc. Rev, 2012, 41, 2971.
Kanasty et al., "Delivery materials for siRNA therapeutics", Nat. Mater., 2013, 12, 967-977.
Kennecke et al., "Metastatic Behavior of breast cancer subtypes", J. Clin. Oncol., 2010, 28, 3271-3277.
Lin et al., "Brain Metastases: the HER2 paradigm", Clin. Cancer Res., 2007, 13, 1648-1655.
Lytton-Jean et al., "Five Years of siRNA delivery: Spotlight on gold nanoparticles", Small, 2011, 7(14), 1932-1937.
Malek et al., "In Vivo Pharmacokinetics, Tissue Distribution and Underlying Mechanisms of Various PEI(-PEG)/siRNA Complexes", Toxicology and Applied Pharmacology, 2009, 236, 97-108.
Mangani et al., "EXAFS Studies on Copper Transferrin", J Inorganic Biochem., 1992, 48(1), 33-40.
Mehta et al., Therapeutic approaches for HER2-positive brain metastases: Circumventing the blood-brain barrier, Cancer Treat. Rev., 2013, 39, 261-269.
Merkel et al., "Stability of siRNA Polyplexes from Poly(ethylenimine) and Poly(ethylenimine)-g-poly(ethlene glycol) Under in Vivo Conditions: Effects on Pharmacokinetics and Biodistribution Measured by Fluorescence Fluctuation Spectroscopy and Single Photon Emission Computed Tomography (SPECT) Imaging", Journal of Controlled Release, 2009, 138, 148-159.
Mikado et al., "Application of Neutron Capture Autoradiography to Boron Delivery Seeking Techniques for Selective Accumulation of Boron Compounds to Tumor with Intra-Arterial Administration of Boron Entrapped Water-in-Oil-Water Emulsion", Nucl Instrum Meth A, 2009, 605, 171-174.
Mittapalli et al., "Paclitaxel-hyaluronic nanoconjugates prolong overall survival in a preclinical brain metastases of breast cancer model", Mol. Cancer Ther., 2013, 12, 2389-2399.
Mittapalli et al., "Quantitative Fluoescence microscopy measures vascular pore size in primary and metastatic brain tumors", Cancer Res., 2017, 77, 238-246.
Mohammad et al., "Liosomal irinotecan accumulates in metastatic lesions, crosses the blood-tumor barrier (BTB) and prolongs survival in an experimental model of brain metastases of triple negative breast cancer", Pharm. Res. 2018, 35.
Morikawa et al., "Capecitabine and lapatinib uptake in surgically resected brain metastases from metastatic breast cancer patients: a prospective study", Neuro. Oncol., 2015, 17, 289-295.

(56) References Cited

OTHER PUBLICATIONS

Nelson et al., "Balancing cationic and hydrophobic content of PEGylated siRNA polyplexes enhances endosome escape, stability, blood circulation time, and bioactivity in vivo", ACS Nano., 2013, 7, 8870-8880.
Neuwelt et al., "Strategies to Advance Translational Research into Brain Barriers", Lancet Neural, 2008, 7(1), 84-96.
Oehrlich et al., "Clinical outcome of brain metastases differs significantly among breast cancer subtypes", Oncol. Lett., 2017, 14, 194-200.
Office Action issued for China Patent Application No. 200980131484.0 filed Feb. 12, 2011 dated Feb. 21, 2012 with English translation attached.
Osswald et al., "Impact of blood-brain barrier integrity on tumor growth and therapy response in brain metastases", Clin Cancer Res., 2016, 22, 6078-6087.
Pan et al., "Cationic Mucic acid polymer-based siRNA delivery systems", Bioconjugate Chemistry, 2015, 26(8), 1791-1803.
Pardridge et al., "Delivery of Biologies across the blood-brain barrier with molecular trojan horse technology", BioDrugs, 2017, 31, 503-519.
Pardridge et al., "Drug targeting to the brain", Pharm. Res., 2007, 24, 1733-1744.
Pardridge, "Blood-Brain Barrier Drug targeting: The Future of Brain Drug Development", Molecular Interventions, Mar. 2003, vol. 3, No. 2, 90-105.
Pardridge, "The Blood-Brain Barrier: Bottleneck in Brain Drug Development", NeuroRX, 2005, 2(1), 3-14.
Peer et al., "Nanocarriers as an emerging platform for cancer therapy", Nat. Nanotechnol., Dec. 2007, 2, 751-760.
Pun et al., "Development of a nonviral gene delivery vehicle for systemic application", Bioconjugate Chem., 2002, 13, 630-639.
Pun et al., "Targeted Delivery of RNA-Cleaving DNA Enzyme (DNAzyme) to Tumor Tissue by Transferrin-Modified, Cyclodextrin-Based Particles", Cancer Biology and Therapy, 3, 7, Jul. 2004, 641-650.
Ramakrishna et al., "Recommendations on disease management for patients with advanced human epidermal growth factor receptor 2-positive breast cancer and brain metastases: American Society of Clinical Oncology Clinical Practice Guideline", J. Clin. Oncol., 2014, 32, 2100-2108.
Reineke et al., "Structural Effects of Carbohydrate-Containing Polycations on Gene Delivery. 1. Carbohydrate Size and its Distance from Charge Centers", Bioconjugate Chem, 2003, 14, 247-254.
Rostami et al., "Brain metastasis in breast cancer: a comprehensive literature review", J. Neurooncol., 2016, 127, 407-414.
Sapsford et al., "Functionalizing Nanoparticles with Biological Molecules: Developing Chemistries that Facilitate Nanotechnology", Chemical Reviews, Feb. 22, 2013, 113, 1904-2074.
Saraiva et al., "Nanoparticle-mediated brain drug delivery: Overcoming blood-brain barrier to treat neurodegenerative diseases", Journal of Controlled Release, 2016, 235, 34-47.
Sato et al., "Polymer brush-stabilized polyplex for a siRNA carrier with long circulatory half-life," Journal of Controlled Release, 2007, 122, 209-216.
Sawyer et al: Convection-enhanced delivery of camptothecin-loaded polymer nanoparticles for treatment of intracranial tumors, Drug Deliv Transl Res. Feb. 1, 2011; 1(1): 34-42.
Sawyer et al: New Methods for Direct Delivery of Chemotherapy for Treating Brain Tumors, Yale Journal of Biology and Medicine 79, 2006, 141-152.
Shah et al., "Investigational chemotherapy and novel pharmacokinetic mechanisms for the treatment of breast cancer brain metastases", Pharmacol. Res., 2018, 132, 47-68.
Sonavane, G., et al. "Biodistribution of colloidal gold nanoparticles after intravenous administration: Effect of particle size", Colloids and Surfaces B: Biointerfaces, 2008, pp. 276-280.
Taskar et al., "Lapatinib distribution in HER2 Overexpressing experimental brain metastases of breast cancer", Pharm. Res., 2012, 29, 770-781.
Terrell-Hall et al., "Trastuzumab distribution in an in-vivo and in-vitro model of brain metastases of breast cancer", Oncotarget, 2017, 8, 83734-83744.
Torchilin et al., "TAT Peptide on the Surface of Liposomes Affords Their Efficient Intracellular Delivery Even At Low Temperature and in the Presence of Metabolic Inhibitors", PNAS, Jul. 2001, 98(15), 8786-8791.
Tuffin et al., "Immunoliposome Targeting to Mesangial Cells: A Promising Strategy for Specific Drug Delivery to the Kidney", J. Am. Soc. Nephrol., 2005, 16, 3295-3305.
Uchida et al., "Quantitative targeted absolute proteomics of human blood-brain barrier transporters and receptors", J. Neurochem., 2011, 117, 333-345.
Van Rooy et al., "Identification of Peptide Ligands for Targeting the Blood-Brain Barrier", Pharmaceutical Research, Apr. 2010, 27(4), 673-682.
Wiley et al: "Transcytosis and brain uptake of transferrincontaining nanoparticles by tuning avidity to transferrin receptor", Proceedings of the National Academy of Sciences, vol. 110, No. 21,May 6, 2013 (May 6, 2013), pp. 8662-8667.
Wolf, W. et al., "'F-MRS Studies of Fluorinated Drugs in Humans", Advanced Drug Delivery Reviews, 2000, 41, 55-74.
Wu et al., "Recent progress in copolymer-mediated siRNA delivery", Journal of Drug Targeting, 2012, 20(7), 551-560.
Wu et al., "RNAi Therapies: Drugging the Undruggable", Science Transl. Med., 2014, 6, 240ps7, 1-8.
Wyatt et al., "Method of establishing breast cancer brain metastases affects brain uptake and efficacy of targeted, therapeutic nanoparticles", Bioeng. Trans. Med., 2018, doi: 10.1002/btm2.10108.
Xiao et al., "The Effect of Surface Charge on in Vivo Biodistribution of PEG-oligocholic Acid Based Micellar Nanoparticles", Biomaterials, 2011, 32, 3435-3446.
Xue et al. "Highlighting the role of polymer length, carbohydrate size, and nucleic acid type in potency of glycopolycation agents for pDNA and siRNA delivery", Biomacromolecules, 2013, 14, 3903-3915.
Yu et al., "Boosting Brain Uptake of a Therapeutic Antibody by Reducing Its Affinity for a Transcytosis Target", Sci Transl Med, 2011, 3(84), 1-8.
Zhong et al. "Low molecular weight linear polyethyleneimine-b-poly(ethylene glycol)-b-polyethyleneimine triblock copolymers: Synthesis, characterization, and in vitro gene transfer properties", Biomacromolecules, 2005, 6, 3440-3448.
Zhou et al: Highly penetrative, drug-loaded nanocarners improve treatment of glioblastoma. PNAS Early Edition, 2013, 1-6.
Zhu et al. "Amphiphilic cationic [dendritic poly(L-lysine)]-block-poly(L-lactide)-block-[dendritic poly(L-lysine)]s in aqueous solution: Self-aggregation and interaction with DNA as gene delivery carries", Macromol. Biosci., 2011, 11, 174-186.
Zuckerman et al., "Correlating animal and human phase la/1b clinical data with CALAA-01, a targeted, polymer-based nanoparticle containing siRNA", Proc. Natl. Acad. Sci. USA, 2014, 111, 11449-11454.

Mucic acid ethylenediamine

Dimethyl Suberimidate

Dimethyl Suberimidate - hydrolyzed

Dimethyl Suberimidate – hydrolyzed to carboxylate

CATIONIC MUCIC ACID POLYMER-BASED DELIVERY SYSTEMS

CROSS REFERENCE TO RELATED APPLICATIONS

This application is a continuation of U.S. patent application Ser. No. 16/351,168, filed Mar. 12, 2019, which is a continuation of U.S. patent application Ser. No. 15/180,201, filed Jun. 13, 2016, that issued as U.S. Pat. No. 10,287,401 on May 14, 2019, which claims the benefit of priority to U.S. Patent Application Ser. No. 62/187,366, filed Jul. 1, 2015, the contents of each of which are incorporated by reference herein for all purposes.

GOVERNMENT RIGHTS

This invention was made with government support under Grant No. CA151819 awarded by National Institutes of Health. The government has certain rights in the invention.

TECHNICAL FIELD

The present disclosure is directed to polymer and polymer conjugate-based nanoparticle delivery systems for delivering biological agents, and methods of making and using these compositions.

BACKGROUND

Therapeutics that use RNA interference (RNAi) as their mechanism of action have great promise for the treatment of human disease. For example, siRNA has attractive features for use as a therapeutic, including: (i) the ability to target essentially any gene (thus, all targets are in principle druggable), (ii) potent, single-digit, picomolar $IC_{50}$'s (concentration required for 50% inhibition) for mRNA inhibition in well-designed siRNAs, (iii) chemical modifications and sequence designs that can minimize off-target effects and immune stimulation without compromising potency and target specificity, and (iv) a catalytic RNAi mechanism of action, resulting in extended siRNA inhibition of mRNA target expression. Although a major obstacle to the translation of siRNA into an effective and efficient therapeutic is the delivery of the nucleic acid to the target, siRNA-based experimental therapeutics have reached the clinic.

Therapeutics investigated for cancer treatment are primarily administered systemically and use some type of synthetic compounds (positively charged lipids or polymers) in their formulations to deliver siRNA. A number of these formulations are now called nanoparticles (NPs). CALAA-01 was the first siRNA-based therapeutic to reach the clinic for the treatment of cancer. This targeted nanoparticle contains a cyclodextrin-based polycation (CDP) that assembles with siRNA via electrostatic interactions between positive charges on the polymer and negative charges on the siRNA backbone. CALAA-01 was able to deliver siRNA to solid tumors in patients and release functional siRNA that inhibited the target using an RNAi mechanism (the first example in a human). While CALAA-01 revealed several positive attributes, one of its shortcomings is that it has a very limited circulation time. The fast clearance of CALAA-01 that is observed in animals (mice, rats, dogs, and non-human primates) is also observed in humans.

SUMMARY

The development of a polymer system for siRNA delivery that both increases the circulation time of siRNA-containing nanoparticles and decreases the amount of non-siRNA components within the formulation would be advantageous. The present disclosure is directed to delivery systems that overcome some of the shortcomings of the prior art. Among the aspects of the present disclosure is a family of cationic mucic acid-based polymers (cMAP), including diblock and triblock copolymers, for siRNA delivery in vivo, and nanoparticles derived therefrom. These compounds and structures and their methods of making and using are described more within this specification.

Certain embodiments of the present disclosure provide polymers comprising alternating charged and uncharged segments comprising one or more of the following structural units of Formula (I) or Formula (II) or Formula (III):

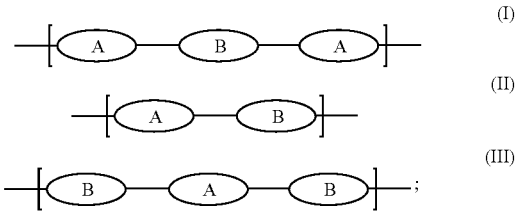

wherein
A is an uncharged segment comprising polyalkylene glycol;
B is a cationically charged segment comprising at least one polyhydroxy linkage comprising at least one pair of vicinal diols.

In certain aspects, A is or comprises polyethylene glycol and an appropriate linking group. In other embodiments, the polyalkylene glycol moieties within these polymers have a nominal number averaged molecular weight in a range of from about 500 Daltons to about 50,000 Daltons In overlapping aspects, B is a cationically charged segment comprising at least one polyhydroxy comprising at least one pair of vicinal diols that comprises a sugar linkage. In some embodiments, these polyhydroxy linkages comprise mucic acid. B may further comprise at least one repeating subunit comprising a structure of Formula (V):

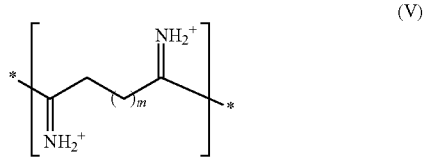

wherein m is 1, 2, 3, 4, 5, 6, 7, 8, 9, or 10, preferably 4-6 or 5.

In other embodiments, in these polymers, B may comprise at least one repeating subunit comprising cMAP, whose subunit structure is represented as Formula (VI):

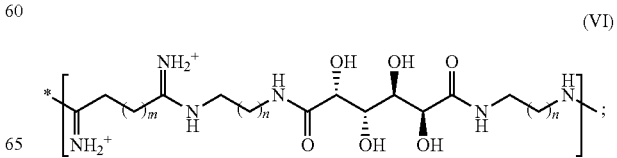

wherein
  m is independently at each occurrence 1, 2, 3, 4, 5, 6, 7, 8, 9, or 10, preferably 4-6 or 5; and
  n is independently at each occurrence 1, 2, 3, 4, or 5.

In some specific embodiments, the polymers may be described by a structure of Formula (VII):

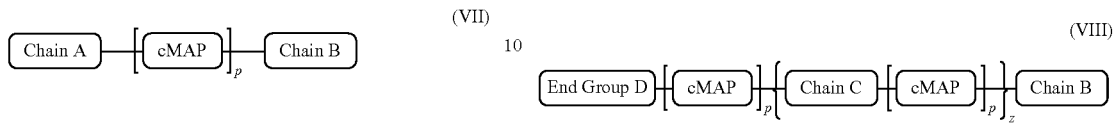
(VII)

wherein
Chain A is

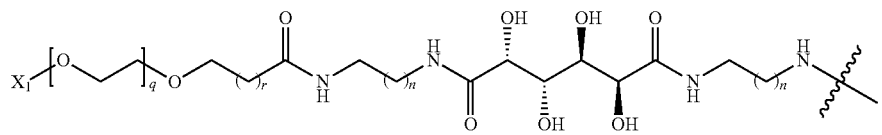

Chain B is

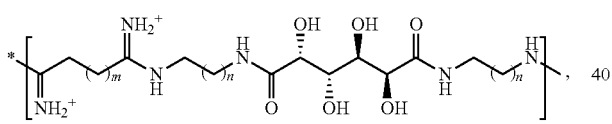

cMAP is

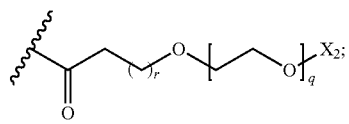

p and q are sufficient to provide a number average molecular weight for the subunits comprising cMAP and PEG, respectively, independently in a range of from about 500 Da to about 50,000 Da;

m is independently at each occurrence 1, 2, 3, 4, 5, 6, 7, 8, 9, or 10, preferably 4-6 or 5;

n and r are independently at each occurrence 0, 1, 2, 3, 4, or 5; and $X_1$ and $X_2$ are independently at each occurrence $C_{1-6}$ alkyl, optionally substituted with —OH, —COOH, —C(=O)O(alkyl), —C(=O)O(aryl), —NH$_2$, —NH(alkyl), —N(alkyl)$_2$, or a salt or protected analog thereof.

Other structures considered within the scope of this disclosure include those polymers described by a structure of Formula (VIII):

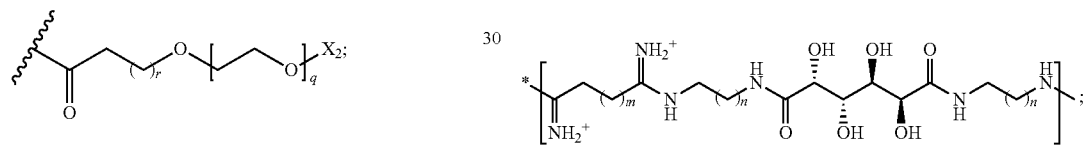
(VIII)

wherein
cMAP is

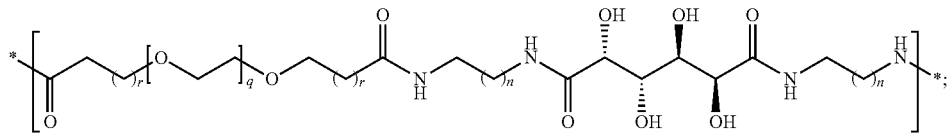

Chain B is

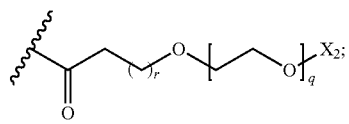

Chain C is

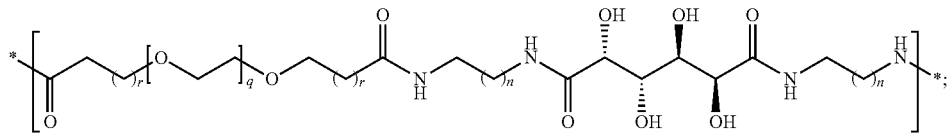

End Group D is:

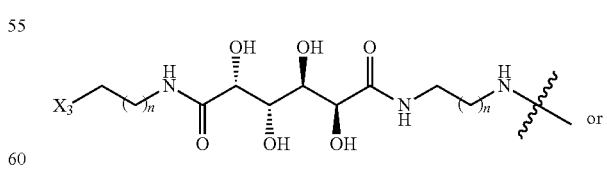
or
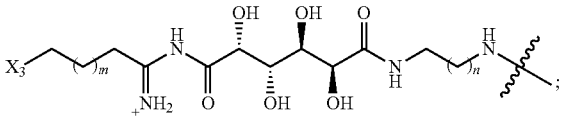

p and q are sufficient to provide a number average molecular weight for the subunits comprising cMAP and PEG, respectively, independently in a range of from about 500 Da to about 50,000 Da;

m is independently at each occurrence 1, 2, 3, 4, 5, 6, 7, 8, 9, or 10, preferably 4-6 or 5;

n and r are independently at each occurrence 0, 1, 2, 3, 4, or 5;

z is equal to or greater than 1 (up to about 2, 4, 6, 8, or 10); and $X_2$ is independently at each occurrence $C_{1-6}$ alkyl, optionally substituted with —OH, —COOH, —C(=O)O(alkyl), —C(=O)O(aryl), —NH$_2$, —NH(alkyl), —N(alkyl)$_2$, or a salt or protected analog thereof and $X_3$ is —OH, —COOH, —C(=O)O(alkyl), —C(=O)O(aryl), —NH$_2$, —NH(alkyl), —N(alkyl)$_2$, or a salt or protected analog thereof.

Still other polymer can be described by a structure of Formula (IX):

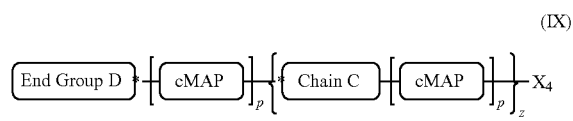

wherein
End Group D is:

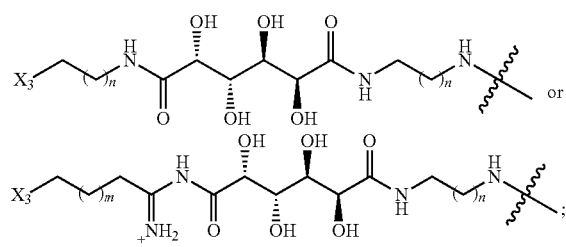

cMAP is

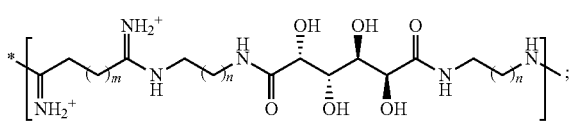

Chain C is

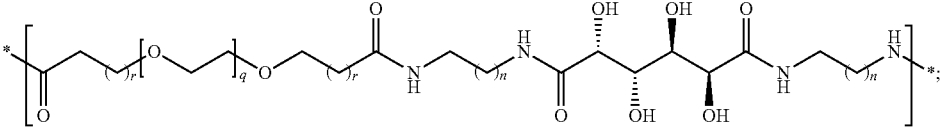

p and q are sufficient to provide a number average molecular weight for the subunits comprising cMAP and PEG, respectively, independently in a range of from about 500 Da to about 50,000 Da, preferably from about 1000 Da to about 5000 Da;

m is independently at each occurrence 1, 2, 3, 4, 5, 6, 7, 8, 9, or 10, preferably 4-6 or 5;

n and r are independently at each occurrence 0, 1, 2, 3, 4, or 5;

z is equal to or greater than 1 (up to about 2, 4, 6, 8, or 10); and $X_3$ and $X_4$ are independently at each occurrence —OH, —COOH, —C(=O)O(alkyl), —C(=O)O(aryl), —NH$_2$, —NH(alkyl), —N(alkyl)$_2$, or a salt or protected analog thereof.

Also considered within the scope of the present disclosure are polymer conjugates each comprising a polymer of any one of the preceding structures and a second boronic acid-containing polymer comprising a structure of Formula (X)

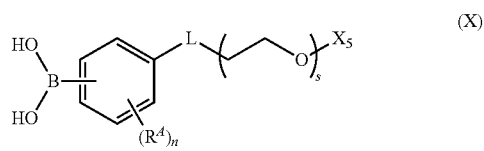

wherein
the polymer and the second boronic acid-containing polymer are reversibly connected to one another by a borate condensation linkage between the boronic acid moieties of Formula (X) and at least one pair of vicinal diols of the polyhydroxy linkages of Formula (I), (II), (III), (IV), (VI), (VII), (VIII), or (IX), $X_5$ being at the distal end of this connection;

$R^A$ is nitro (or other electron withdrawing group);

n is 0, 1, 2, 3, or 4, preferably 1;

s is 20-1200;

L is a linking group between the phenyl ring and the polyethylene oxide linkage; and $X_5$ is $C_{1-6}$ alkyl, optionally substituted with —OH, —COOH, —C(=O)O(alkyl), —C(=O)O(aryl), —NH$_2$, or a salt or protected analog thereof.

The disclosure also includes a nanoparticle or plurality of nanoparticles comprising any of the polymers or polymer conjugates described herein. Preferably the nanoparticles are monodispersed. The nanoparticles may further comprise encapsulated biological agents, for example siRNA and/or may be further conjugated to one or more targeting ligands. When administered to a patient, the bioavailability of the biological agent is better than the same bioavailability of the biological agent when administered by itself.

In some additional embodiments, the polymers, polymer conjugates, and nanoparticles, optionally comprising a biological agent and/or targeting ligand are formulated into pharmaceutical compositions. Other embodiments provide for treating patients by the administration of these formulated compositions to patients in need of treatment by the respective biological agents.

Still further embodiments provide the methods of making the inventive polymers.

BRIEF DESCRIPTION OF THE DRAWINGS

The present application is further understood when read in conjunction with the appended drawings. For the purpose of illustrating the subject matter, exemplary embodiments of the subject matter are shown in these drawings; however, the presently disclosed subject matter is not limited to the specific methods, devices, and systems disclosed. In addition, the drawings are not necessarily drawn to scale. In the drawings:

FIG. 24A shows a comparison of siRNA alone with CALAA-01, the CDP system with AD2-PEG for stabilization, and cMAP+5-nPBA-PEGm showing greater stability than CDP with AD$_2$-PEG and CALAA-01. FIG. 24B shows a comparison of cMAP+5-nPBA-PEGm to the copolymer and triblock formulations. FIG. 24C shows a comparison of cMAP+5-nPBA-PEGm to the triblock formulation with excess components filtered away. n=3 mice.

DETAILED DESCRIPTION OF ILLUSTRATIVE EMBODIMENTS

Figure 1:
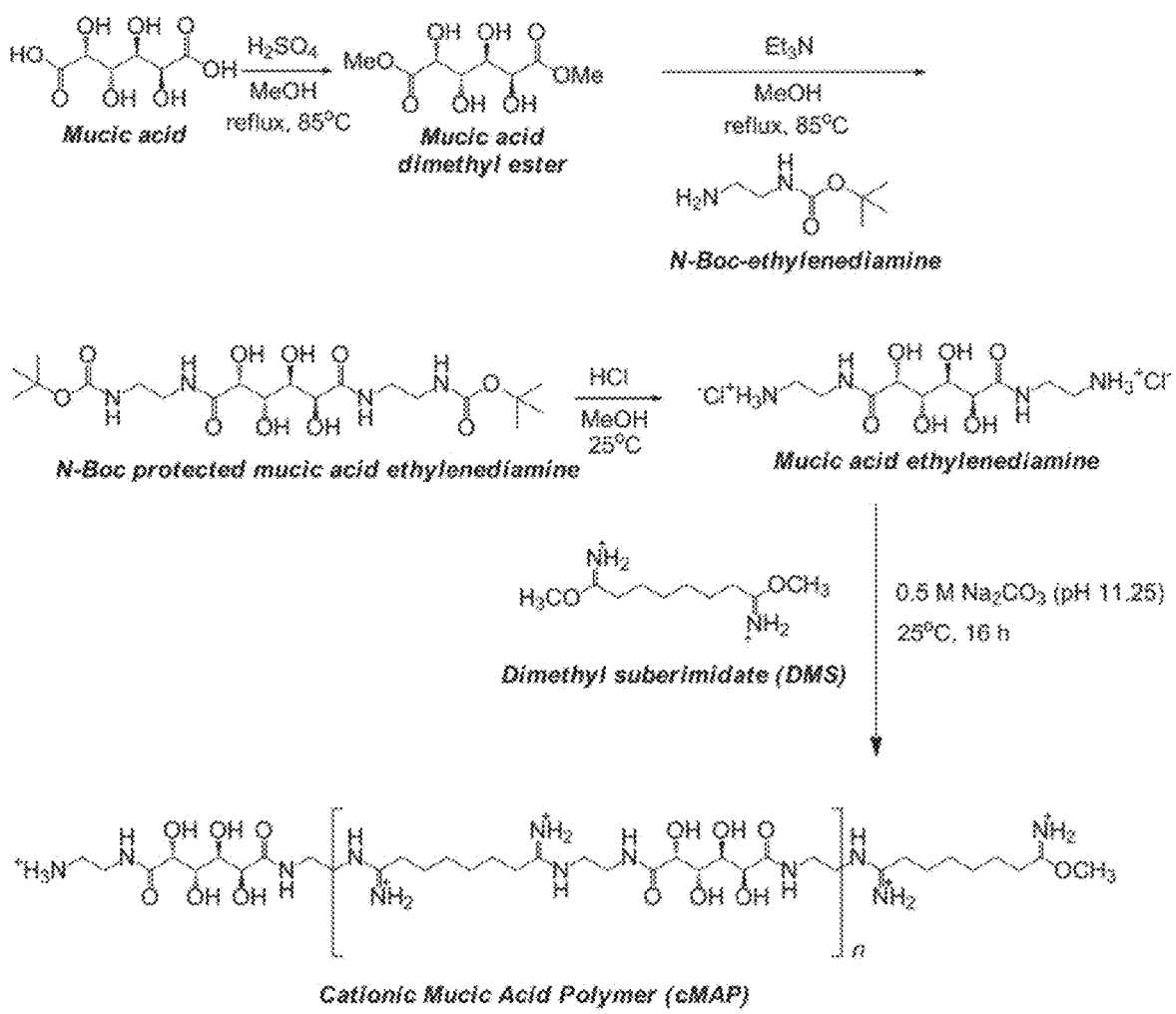
FIG. 1 shows a schematic representation of a synthesis of cationic Mucic Acid Polymer (cMAP).

The present disclosure is directed to delivery systems that overcome some of the shortcomings of the prior art.

The present inventors have investigated the origin of the short circulation time referred elsewhere herein and have shown that CALAA-01 disassembles at the glomerular basement membrane (GBM) in the kidney. The present inventors speculated that this clearance mechanism may affect any NP formulation that is primarily assembled through electrostatic interactions between cationic delivery components and anionic nucleic acids. Other siRNA delivery systems that use either cationic polymers or lipids have shown similar short circulation times and renal clearance.

A number of the current polymeric and liposomal systems used to deliver siRNA in vivo contain excess cationic components in their formulations (positive to negative charge ratios are commonly greater than 1), in addition to a large amount of material, e.g., poly(ethylene glycol) (PEG), used to sterically stabilize the formed NPs. Excess cationic components can have unwanted side effects in vivo, causing adverse reactions such as platelet aggregation, complement activation, and inflammatory reactions.

The development of a polymer system for siRNA delivery that both increases the circulation time of siRNA-containing nanoparticles and decreases the amount of non-siRNA components within the formulation would be advantageous. Described herein is a family of cationic mucic acid-based polymers (cMAP) for siRNA delivery in vivo. This polymer delivery system has some features analogous to the CDP system, since the latter system did function in humans. The cationic polymer developed here uses a simpler sugar, exemplified as mucic acid, rather than the cyclodextrin, and enables an alternative strategy for surface functionalization. Instead of nanoparticle surface functionalization via inclusion complex formation (CDP) with adamantane (AD), the cMAP contains vicinal diols that are binding sites for boronic acids which can be used to PEGylate and target the cMAP-based nanoparticles. Nanoparticles formed with mucic acid containing polymers for the delivery of small molecule drugs have incorporated targeting agents via this method of assembly. The basic cMAP was also further reacted with functionalized PEG into linear block copolymers. Reaction at the end-groups of cMAP with either a di-activated, carboxylic acid-PEG or an activated, carboxylic acid-PEG-methoxy (PEGm) leads to two possible copolymers: a cMAP-PEG copolymer or an mPEG-cMAP-PEGm triblock polymer. The cMAP-PEG copolymer can assemble with siRNA to form PEG loops on the surface to stabilize the nanoparticle, while the mPEG-cMAP-PEGm triblock can form a PEG brush configuration on the nanoparticle surface. The latter triblock approach has been explored previously with CDP and plasmid DNA (pDNA), and that triblock polymer did not have the ability to encapsulate the pDNA. It has been shown that polymers that encapsulate pDNA may not be good at condensing siRNA and vice versa. Here, we demonstrate that the mPEG-cMAP-PEGm triblock polymer is able to form siRNA-containing nanoparticles (which can have ca. 30 wt % of the formulation being siRNA) with increased circulation times in mice. Additionally, the nanoparticles can be easily assembled directly in phosphate buffered saline (PBS) without any additional 5-nPBA-PEGm to stabilize the NPs.

The present disclosure may be understood more readily by reference to the following description taken in connection with the accompanying Figures and Examples, all of which form a part of this disclosure. It is to be understood that this disclosure is not limited to the specific products, methods, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the disclosure herein is not to be constrained by the correctness or incorrectness of any such suggested mechanism or mode of action or reason for improvement. Throughout this text, it is recognized that the descriptions refer to compositions and methods of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the disclosure which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the disclosure that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of" For those embodiments provided in terms of "consisting essentially of" the basic and novel characteristic(s) is the facile operability of the methods (and the systems used in such methods and the compositions derived therefrom) to prepare and use the inventive materials, and the materials themselves, where the methods and materials are capable of delivering the highlighted properties using only the elements provided in the claims. That is, while other materials may also be present in the inventive compositions, the presence of these extra materials is not necessary to provide the described benefits of those compositions (i.e., the effects may be additive) and/or these additional materials do not compromise the performance of the product compositions. Similarly, where additional steps may also be employed in the methods, their presence is not necessary to achieve the described effects or benefits and/or they do not compromise the stated effect or benefit.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C." Likewise, a term such as $C_{1-3}$ alkyl also includes, as separate embodiments, $C_1$ alkyl, $C_2$ alkyl, $C_3$ alkyl, $C_{1-2}$ alkyl, and $C_{2-3}$ alkyl.

Throughout this specification, words are to be afforded their normal meaning, as would be understood by those skilled in the relevant art. However, so as to avoid misunderstanding, the meanings of certain terms will be specifically defined or clarified.

Reference to alcohols, aldehydes, amines, carboxylic acids, ketones, or other similarly reactive functional groups also includes their protected analogs. For example, reference to hydroxy or alcohol also includes those substituents wherein the hydroxy is protected by acetyl (Ac), benzoyl (Bz), benzyl (Bn, Bnl), β-Methoxyethoxymethyl ether (MEM), dimethoxytrityl, [bis-(4-methoxyphenyl)phenylmethyl] (DMT), methoxymethyl ether (MOM), methoxytrityl [(4-methoxyphenyl)diphenylmethyl, MMT), p-methoxybenzyl ether (PMB), methylthiomethyl ether, pivaloyl (Piv), tetrahydropyranyl (THP), tetrahydrofuran (THF), trityl (triphenylmethyl, Tr), silyl ether (most popular ones include trimethylsilyl (TMS), tert-butyldimethylsilyl (TBDMS), triiso-propylsilyloxymethyl (TOM), and triisopropylsilyl (TIPS) ethers), ethoxyethyl ethers (EE). Reference to amines also includes those substituents wherein the amine is protected by a BOC glycine, carbobenzyloxy (Cbz), p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), carbamate, p-methoxybenzyl (PMB), 3,4-dimethoxybenzyl (DMPM), p-methoxyphenyl (PMP), tosyl (Ts) group, or sulfonamide (Nosyl & Nps) group. Reference to substituent containing a carbonyl group also includes those substituents wherein the carbonyl is protected by an acetal or ketal, acylal, or diathane group. Reference to substituent containing a carboxylic acid or carboxylate group also includes those substituents wherein the carboxylic acid or carboxylate group is protected by its methyl ester, benzyl ester, tert-butyl ester, an ester of 2,6-disubstituted phenol (e.g. 2,6-dimethylphenol, 2,6-diisopropylphenol, 2,6-di-tert-butylphenol), a silyl ester, an orthoester, or an oxazoline.

Embodiments of the present disclosure include polymers comprising alternating charged and uncharged segments comprising one or more of the following structural units of Formula (I) or Formula (II) or Formula (III):

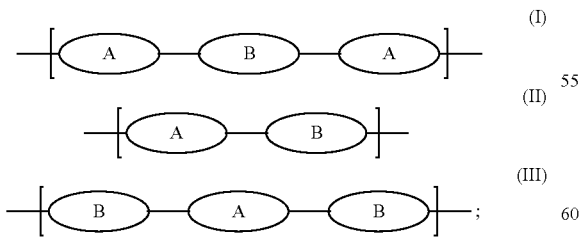

wherein
A is an uncharged segment comprising polyalkylene glycol; B is a cationically charged segment comprising at least one polyhydroxy linkage comprising at least one pair of vicinal diols.

In the polymers of the present disclosure, the term polyalkylene glycol refers to any polymer containing the functional linkage:

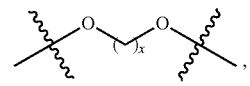

where x is in a range of from 1 to about 6, though practically and preferably is either 2 or 3, preferably 2 (at higher values of x, the polyalkylene glycol shows poor hydrophilicity). So in preferred embodiments, A is or comprises a polyethylene glycol and an optional (but preferably) appropriate linking group, the linking group being necessary to bond to the other components of the general polymer. Preferably, at each occurrence, the polyalkylene glycol, generally, and polyethylene glycol specifically has a nominal number average molecular weight ($MW_n$) in a range of from about 500 Daltons to about 50,000 Daltons. In more specific embodiments, the polyalkylene/polyethylene glycol moieties have values of $MW_n$ of from about 500 Da to about 1 kDa, from about 1 kDa to about 5 kDa, from about 5 kDa to about 10 kDa, from about 10 kDa to about 15 kDa, from about 15 kDa to about 20 kDa, from about 20 kDa to about 30 kDa, from about 30 kDa to about 40 kDa, from about 40 kDa to about 50 kDa, or any combination of two or more of these ranges.

In certain of these embodiments, B is a cationically charged segment comprising at least one polyhydroxy linkage comprising at least one pair of vicinal diols. Polyhydroxy sugar or carbohydrate linkages are preferred for their biocompatibility, though chiral and achiral synthetic polyhydroxy linkage may also be employed (e.g., polyhydroxy (meth)acrylic acid). In certain preferred embodiments, the polyhydroxy linkage comprises mucic acid, wherein B comprises at least one repeating subunit comprising a structure of Formula (IV), presented either as (IV) or (IVA):

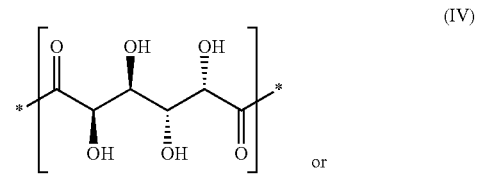

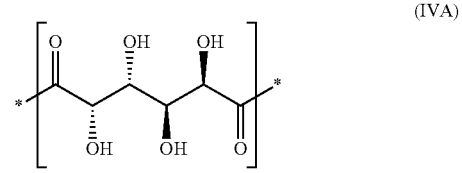

These structures are rotational isomers of each other and for present purposes are functionally equivalent. As used herein, representation of one of these structures connotes either or both of these structures in the context of their use.

In other embodiments, B further comprises at least one repeating subunit comprising a structure of Formula (V):

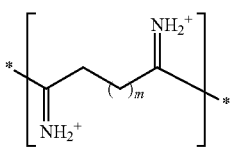

(V)

wherein m is 1, 2, 3, 4, 5, 6, 7, 8, 9, or 10, preferably 4-6 or 5. Such linkages are useful linking groups both for their cationic character and for their convenience of use in linking the polyhydroxy (e.g., mucic acid) moieties with the poly-alkylene glycol. When combined with the mucic acid linkage described above, the combination of linkages (IV) and (V) presents a substructure comprising at least one repeating subunit comprising cMAP, whose subunit structure is represented as Formula (VI):

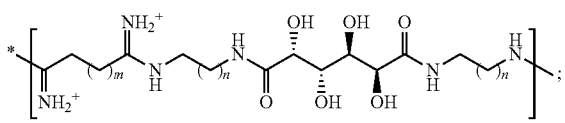

(VI)

wherein m is independently at each occurrence 1, 2, 3, 4, 5, 6, 7, 8, 9, or 10, preferably 4-6 or 5; and n is independently at each occurrence 1, 2, 3, 4, or 5, preferably 1. Note that m and n are not necessarily limited to these values, and larger values for these variables may also be considered within the scope of the present disclosure.

With these building blocks, it is possible to describe a range of more specific tri-block and di-block polymers. Again, the structures described below may be prepared using methods described in the Examples, using homologs of the reactants described there. For example, in certain embodiments, the polymers of the present disclosure include those described by a structure of Formula (VII):

(VII)

wherein
Chain A is

Chain B is

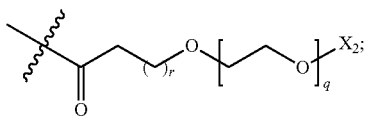

cMAP is

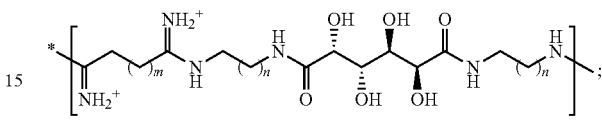

p and q are sufficient to provide a number average molecular weight for the subunits comprising cMAP and PEG, respectively, independently in a range of from about 500 Da to about 50,000 Da;

m is independently at each occurrence 1, 2, 3, 4, 5, 6, 7, 8, 9, or 10 (or even higher), preferably 4-6 or 5;

n and r are independently at each occurrence 0, 1, 2, 3, 4, or 5 (or even higher); and $X_1$ and $X_2$ are independently at each occurrence $C_{1-6}$ alkyl, optionally substituted with —OH, —COOH, —C(=O)O(alkyl), —C(=O)O(aryl), —NH$_2$, —NH(alkyl), —N(alkyl)$_2$, or a salt or protected analog thereof.

Again, values for p and q may be the same or different at each occurrence and the same or different from one another. The same is true for n and r; i.e., values for n and r may be the same or different at each occurrence and the same or different from one another. In certain embodiments, when m is 5 and n is 1, the numeric values for p corresponds to a range of from about 1 to about 100, preferably from about 10 to about 100. Specific embodiments include those where p is in a range of from about 1 to about 10, from about 10 to about 25, from about 25 to about 50, from about 50 to about 75, from 75 to about 100, or any combination of two or more of these ranges. The numeric values for q corresponding to the cited MW$_n$ ranges include those ranging from about 12 to about 1200. Specific embodiments include those where q is in a range of from about 12 to about 100, from about 100 to about 400, from about 400 to about 800, from about 800 to about 1200, or any combination of two or more of these ranges. In specific embodiments, q can also be in a range of from about 100 to about 500. In other subsets of this Embodiment, $X_1$ and $X_2$ are independently at each occurrence —(CH$_2$)$_{1-4}$—COOH and/or —(CH$_2$)$_{1-4}$—NH$_2$.

Given the nature of Chain A and Chain B, such structures may also be designated as a PEG-cMAP-PEG triblock polymer.

In other embodiments, the polymers of the present disclosure include those described by a structure of Formula (VIII):

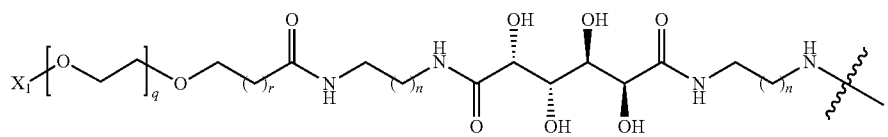

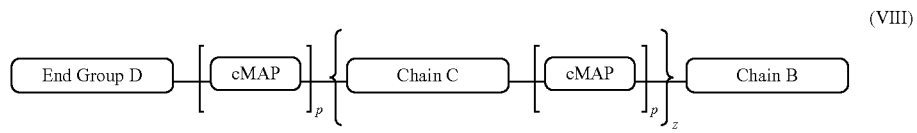

(VIII)

wherein
cMAP is

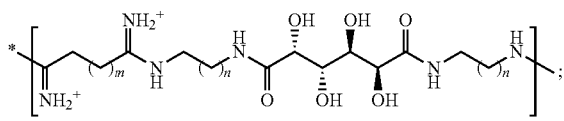

Chain B is

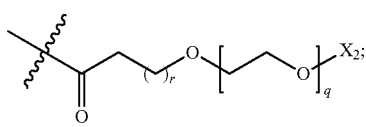

Chain C is

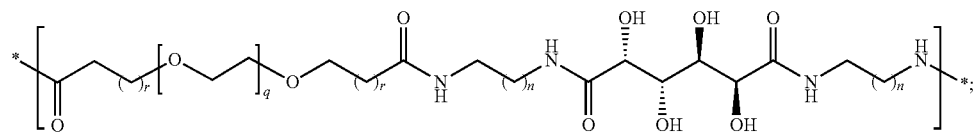

End Group D is:

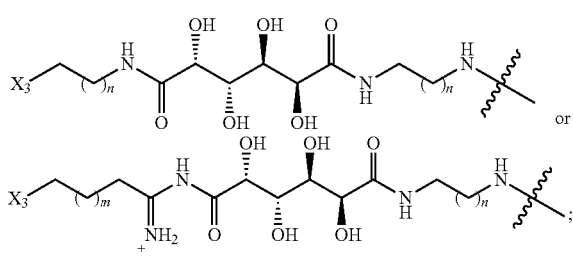

p and q are sufficient to provide a number average molecular weight for the subunits comprising cMAP and PEG, respectively, independently in a range of from about 500 Da to about 50,000 Da;

m is independently at each occurrence 1, 2, 3, 4, 5, 6, 7, 8, 9, or 10, preferably 4-6 or 5;

n and r are independently at each occurrence 0, 1, 2, 3, 4, or 5;

z is equal to or greater than 1 (up to about 2, 4, 6, 8, or 10); and $X_2$ is independently at each occurrence $C_{1-6}$ alkyl, optionally substituted with —OH, —COOH, —C(=O)O(alkyl), —C(=O)O(aryl), —NH$_2$, —NH(alkyl), —N(alkyl)$_2$, or a salt or protected version thereof; and $X_3$ is independently —OH, —COOH, —C(=O)O(alkyl), —C(=O)O(aryl), —NH$_2$, —NH(alkyl), —N (alkyl)$_2$, or a salt or protected analog thereof.

Again, values for p and q may be the same or different at each occurrence and the same or different from one another. The same is true for n and r; i.e., values for n and r may be the same or different at each occurrence and the same or different from one another. In certain embodiments, when m is 5 and n is 1, the numeric values for p corresponds to a range of from about 1 to about 100, preferably from about 10 to about 100. Specific embodiments include those where p is in a range of from about 1 to about 10, from about 10 to about 25, from about 25 to about 50, from about 50 to about 75, from 75 to about 100, or any combination of two or more of these ranges. The numeric values for q corresponding to the cited MW$_n$ ranges include those ranging from about 12 to about 1200. Specific embodiments include those where q is in a range of from about 12 to about 100, from about 100 to about 400, from about 400 to about 800, from about 800 to about 1200, or any combination of two or more of these ranges. In specific embodiments, q can also be in a range of from about 100 to about 500. In other subsets of this Embodiment, $X_1$ and $X_2$ are independently at each occurrence —(CH$_2$)$_{1-4}$—COOH and/or —(CH$_2$)$_{1-4}$—NH$_2$.

Given the nature of the various chain and end group elements, such structures may also be designated as a cMAP-PEG diblock or PEG-cMAP diblock polymer.

In still other embodiments, the polymers of the present disclosure include those described by a structure of Formula (IX):

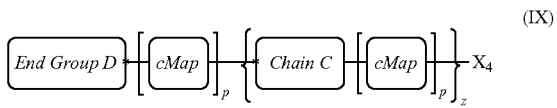

(IX)

wherein
End Group D is:

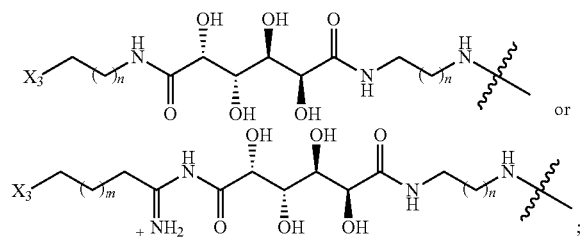

cMAP is

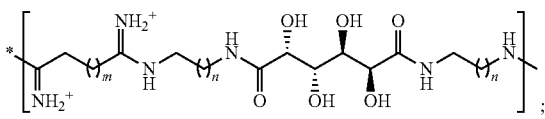

Chain C is

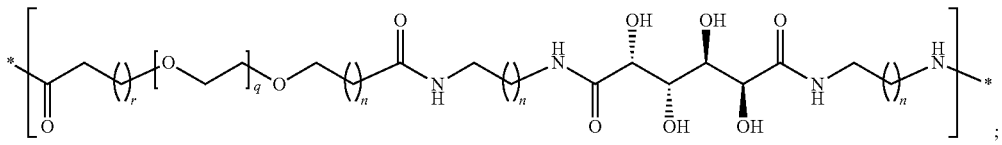

p and q are sufficient to provide a number average molecular weight for the subunits comprising cMAP and PEG, respectively, independently in a range of from about 500 Da to about 50,000 Da, preferably from about 1000 Da to about 5000 Da;

m is independently at each occurrence 1, 2, 3, 4, 5, 6, 7, 8, 9, or 10, preferably 4-6 or 5;

n and r are independently at each occurrence 0, 1, 2, 3, 4, or 5;

z is equal to or greater than 1 (up to about 2, 4, 6, 8, or 10); and $X_2$ is independently at each occurrence $C_{1-6}$ alkyl, optionally substituted with —OH, —COOH, —C(=O)O(alkyl), —C(=O)O(aryl), —$NH_2$, —NH(alkyl), —N(alkyl)$_2$, or a salt thereof; and $X_3$ and $X_4$ are independently at each occurrence —OH, —COOH, —C(=O)O(alkyl), —C(=O)O(aryl), —$NH_2$, —NH(alkyl), —N(alkyl)$_2$, or a salt or protected analog thereof.

Again, values for p and q may be the same or different at each occurrence and the same or different from one another. The same is true for n and r; i.e., values for n and r may be the same or different at each occurrence and the same or different from one another. In certain embodiments, when m is 5 and n is 1, the numeric values for p corresponds to a range of from about 1 to about 100, preferably from about 10 to about 100. Specific embodiments include those where p is in a range of from about 1 to about 10, from about 10 to about 25, from about 25 to about 50, from about 50 to about 75, from 75 to about 100, or any combination of two or more of these ranges. The numeric values for q corresponding to the cited $MW_n$ ranges include those ranging from about 12 to about 1200. Specific embodiments include those where q is in a range of from about 12 to about 100, from about 100 to about 400, from about 400 to about 800, from about 800 to about 1200, or any combination of two or more of these ranges. In specific embodiments, q can also be in a range of from about 100 to about 500. In other subsets of this Embodiment, $X_1$ and $X_2$ are independently at each occurrence —$(CH_2)_{1-4}$—COOH and/or —$(CH_2)_{1-4}$—$NH_2$.

Given the nature of the various chain and end group elements, such structures may also be designated as cMAP-PEG-cMAP triblock polymers.

In each of the structures presented, specific independent embodiments include those where m is independently 4, 5, or 6. In certain embodiments m is 5 at each occurrence.

In each of the structures presented, specific independent embodiments include those where n is 1.

In each of the structures presented, specific independent embodiments include those where r is independently 2, 3, or 4. In some of these embodiments, r is 3 at each occurrence.

In each of the structures presented, specific independent embodiments include those where p is sufficient to provide a number average molecular weight of the subunit comprising cMAP in a range of from about 5 kDa to about 15 kDa, from about 6 kDa to about 14 kDa, 7 kDa to about 13 kDa, from about 8 kDa to about 12 kDa, 9 kDa to about 11 kDa, or about 10 kDa. Where the cMAP fragment has MW of about 420 Da), respectively, this corresponds to numeric values of p in ranges of about 12 to about 36, from about 14 to about 33, from about 17 to about 31, from about 19 to about 29, from about 22 to about 26, or about 24.

In each of the structures presented, specific independent embodiments include those where q is sufficient to provide a number average molecular weight of the subunit comprising PEG in a range of from about 500 Da to about 50 kDa, from about 1 kDa to about 40 kDa, 5 kDa to about 30 kDa, or from about 5 kDa to about 20 kDa. Where the polyalkylene glycol moiety is polyethylene glycol, and given that ethylene glycol fragment has MW of about 44 Da, this corresponds to numeric values of q in ranges of about 11 to about 1200, from about 23 to about 910, from about 110 to about 680, or from about 110 to about 450.

Each combination of values for m, n, p, q, r, or z with any appropriate definition of $X_1$, $X_2$, $X_3$, and/or $X_4$ described herein represents a discrete embodiment, and any combination of these embodiments provides for the definition of another embodiment.

Exemplary, non-limiting schemes for preparing the various polymers described herein are provided in the Examples. Each of these synthetic routes, as well as those using homologs of the specifically described reagents, is considered within the scope of the present disclosure. As used here, the term homolog refers to a compound differing from the exemplar by one or more methylene groups. In one method, a polymer may be prepared by connecting at least one uncharged segment comprising polyalkylene glycol with at least one cationically charged segment comprising at least one polyhydroxy linkage through the use of at least one linking group. In cases where the cationically charged segment is one of the mucic acid derivatives described above, this method comprises stoichiometrically reacting two PEG polymers with a mucic acid polymer, two mucic acid polymers with one PEG polymer, or one mucic acid polymer with one PEG polymer, each with suitable linking groups to form the desired diblock or triblock polymer. Such coupling reactions can be affected using carboxylic acid/amino condensation reactions to form amide linkages as described herein.

The formation of nanoparticles according to several embodiments of the present disclosure can be analyzed with techniques and procedures known by those with skill in the art.

Still other embodiments of the present disclosure include polymer conjugates of the cMAP/PEG-containing polymers described herein. Such polymer conjugates comprise any of the cMAP/PEG-containing polymers and a second boronic acid-containing polymer comprising a structure of Formula (X)

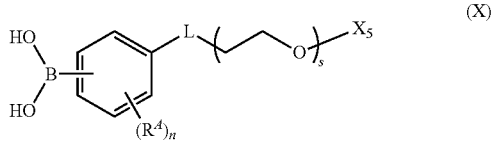

wherein the cMAP/PEG-containing polymer and the second boronic acid-containing polymer are reversible connected to one another by a borate condensation linkage between the boronic acid moieties of Formula (IX) and at least one pair of vicinal diols of the polyhydroxy linkages of Formula (I), (II), (III), (IV), (VI), (VII), (VIII), or (IX), with $X_5$ being at the distal end of this connection;

$R^A$ is nitro (or other electron withdrawing group);

n is 0, 1, 2, 3, or 4, preferably 1;

s is 20-1200;

L is a linking group between the phenyl ring and the polyethylene oxide linkage; and $X_5$ is $C_{1-6}$ alkyl, optionally substituted with —OH, —COOH, —C(=O)O(alkyl), —C(=O)O(aryl), —NH$_2$, —NH(alkyl), —N(alkyl)$_2$, or a salt or protected analog thereof.

In certain of these embodiments, n is 1. Of these embodiments, exemplary structures include:

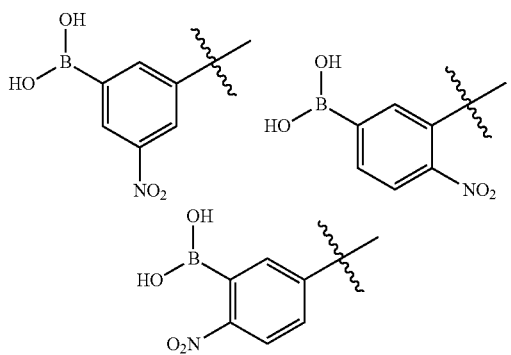

In some embodiments of the polymer conjugates, s is in a range of from 20 to about 120, from about 120 to about 240, from about 240 to about 480, from about 480 to about 720, from about 720 to about 960, from about 960 to about 1200, or any combination of two or more of these ranges.

In other embodiments of the polymer conjugates, L is —(C$_{0-2}$alkylene-)NH—C(=O)—(C$_{0-2}$alkylene)-, —(C$_{0-2}$alkylene)-C(=O)—NH—(C$_{0-2}$alkylene)-, —(C$_{0-2}$alkylene)-O—C(=O)—(C$_{0-2}$alkylene)- or —(C$_{0-2}$alkylene)-C(=O)—O—(C$_{0-2}$alkylene)-. In subsets of these, L is —NH—C(=O)—, —C(=O)—NH—, —O—C(=O)—, or —C(=O)—O—. Single or multiple linking groups of L may be employed with any polymer.

To this point, the disclosure has been described in terms of polymers or polymer conjugates, but important elements of the disclosure include nanoparticles derived from these polymers or polymer conjugates, and the definitions provided for these polymers and polymer conjugates are equally useful in describing the associated nanoparticles. These nanoparticles tend to be substantially similar and depending on the size of the various cMAP or PEG fragments, and/or the lengths of the chains associated with the boronic acid-containing polymer, have cross-sectional dimensions (i.e., diameters) in a range of from about 20 nm to about 300 nm. Specific embodiments can also describe these nanoparticles as having diameters in a range of from about 20 nm to about 40 nm, from about 40 nm to about 80 nm, from about 80 nm to about 120 nm, from about 120 nm to about 180 nm, from about 180 nm to about 240 nm, from about 240 nm to about 300 nm, or a combination of two or more of these ranges.

Likewise, reference to a single nanoparticle should also be considered to include separate embodiments encompassing a population or plurality of nanoparticles. In certain embodiments, the plurality of nanoparticles is substantially monodispersed, with independent embodiments providing that the standard deviation in cross-sectional dimension among the nanoparticles of less than 20%, 30%, 40%, 50%, or 60%, relative to the mean, as measured by cryo-transmission electron microscopy (cryo-TEM). Particle sizes and distributions may be defined by various methods including cryo-TEM photomicrograph analysis. In this method, a predetermined number of particles (more than 100) are analyzed in representative cryo-transmission electron micrographs (typically derived from more than 3 randomly selected liquid samples that have been frozen in liquid ethane) by measuring the mean diameters of the particles, counting particles within a pre-determined size fraction gradient, and statistically correlating those numbers. See also the Examples and Appendix for additional information.

These nanoparticles (comprising any one or more of the inventive polymers or polymer conjugates) are especially attractive for their ability to carry biological "cargo," and in certain embodiments, these nanoparticles further comprise an encapsulated biological agent. These biological agents may be covalently bound or otherwise contained within or by the nanoparticle. In certain embodiments, biological agent is a polynucleotide or a small molecule therapeutic agent. Examples of such therapeutic agents include, but are not limited to, small molecule pharmaceuticals, antibiotics, steroids, polynucleotides (e.g. genomic DNA, cDNA, mRNA, siRNA, shRNA, miRNA, antisense oligonucleotides, viruses, and chimeric polynucleotides), plasmids, peptides, peptide fragments, small molecules (e.g. doxorubicin), chelating agents (e.g. deferoxamine (DESFERAL), ethylenediaminetetraacetic acid (EDTA)), natural products (e.g. Taxol, Amphotericin), and other biologically active macromolecules such as, for example, proteins and enzymes. See also U.S. Pat. No. 6,048,736 which lists active agents (therapeutic agents) that can be used as therapeutic agent with nanoparticles herein described. Small molecule therapeutic agents may not only be the therapeutic agent within the composite particle but, in an additional embodiment, may be covalently bound to a polymer in the composite. In several embodiments, the covalent bond is reversible (e.g. through a prodrug form or biodegradable linkage such as a disulfide) and provides another way of delivering the therapeutic agent. In several embodiments therapeutic agent that can be delivered with the nanoparticles herein described include chemotherapeutics such as epothilones, camptothecin-based drugs, taxol, or a nucleic acid such as a plasmid, siRNA, shRNA, miRNA, antisense oligonucleotides aptamers or their combination, and additional drugs identifiable by a skilled person upon reading of the present disclosure.

In certain preferred embodiments, the biological agent is a polynucleotide that is an RNA molecule. In some of these embodiments, the RNA molecule is an siRNA molecule.

Figure 16A:
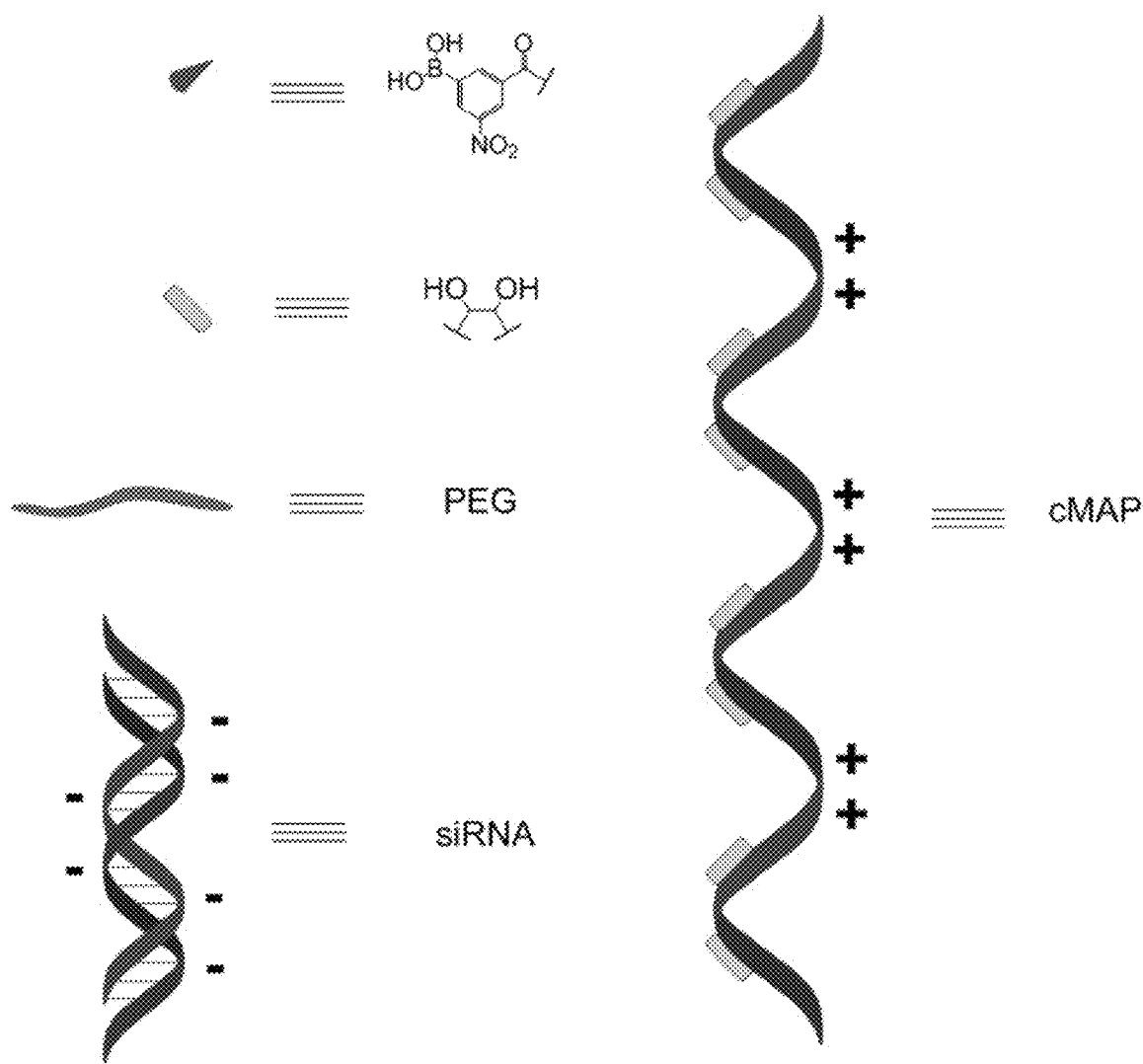
FIGS. 16A and 16B show schematic representations of two diagram showing the various NPs with siRNA that were formed: cMAP (I, not stable and not injected), cMAP+5-nPBA-PEGm (A), cMAP-PEG copolymer (B), cMAP-PEG copolymer+5-nPBA-PEGm (C), mPEG-cMAP-PEGm triblock (D), and mPEG-cMAP-PEGm triblock+5-nPBA-PEGm (E). (Note: Illustration is not drawn to scale or stoichiometry and doesn't reflect how particles are formulated—e.g. in PEGylated formulations the PEG is added to the polymer first, before the siRNA is added).
Figure 16B:
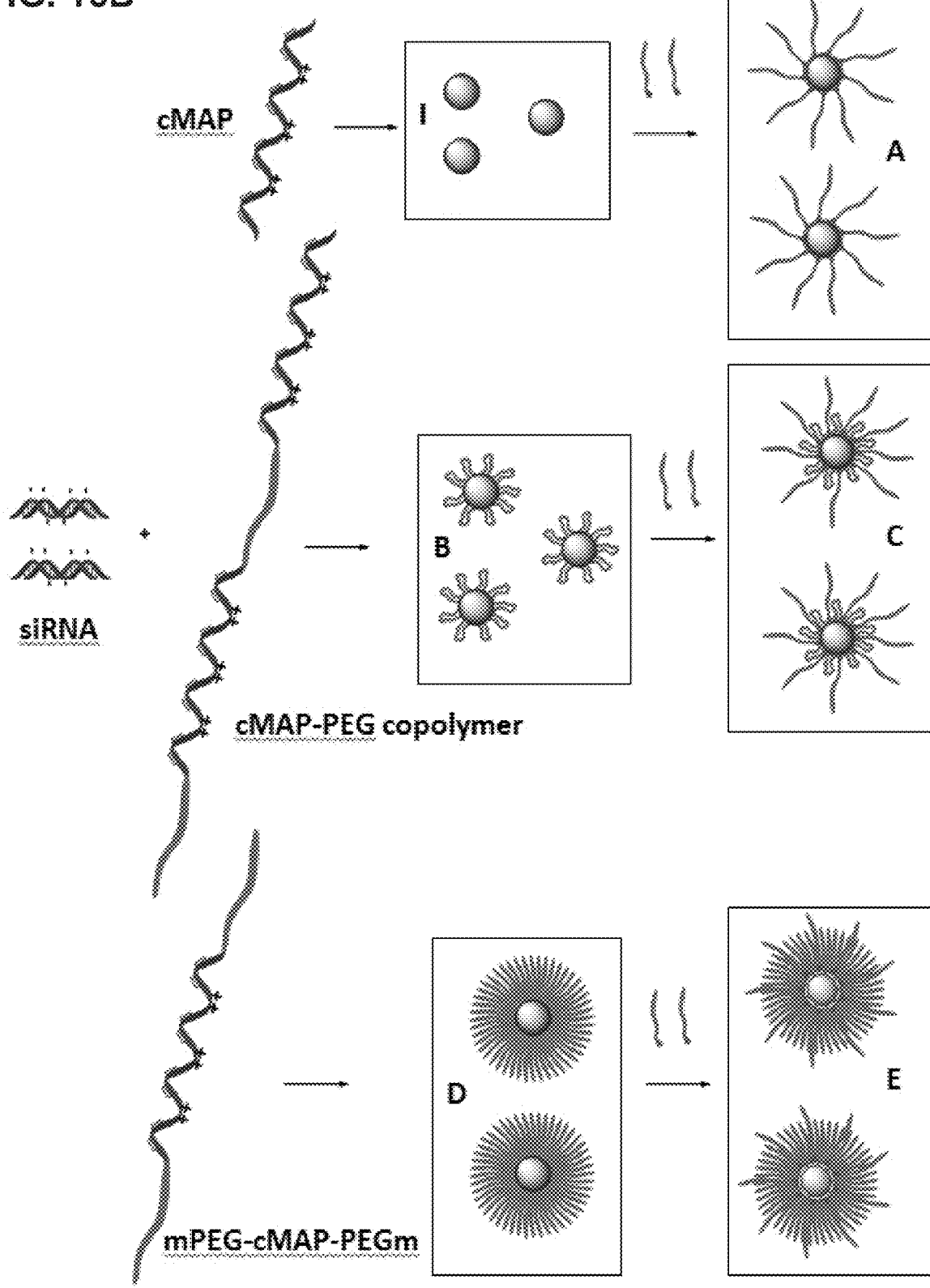

Without intending to be bound by the correctness of any particular theory, it appears that when dispersed in aqueous media, the nanoparticles organize themselves by presenting the hydrophilic linkages to their aqueous environment and maintaining the cationic species in an internal cavity (see, e.g., FIGS. 16A and 16B). Negatively charged cargo, including nucleic acids, associate with the positive charges on the cMAP structures, in some cases aiding in the self-assembly of the nanoparticles.

Where the nanoparticles comprise functionalized (nitro) boronic acid-containing polymer linkages, the nanoparticles may further be conjugated to one or more targeting ligand. In such cases, the conjugation occurs through a condensation linkage between the distal end of the boronic acid-containing polymer and the targeting ligand. In some embodiments, this targeting ligand comprises any one of an antibody, transferrin, a ligand for a cellular receptor, or a cellular receptor protein, an aptamer, or a fragment of an antibody, transferrin, a ligand for a cellular receptor, or a cellular receptor protein. In specific embodiments, a single type of targeting ligand is conjugated to each polymer or nanoparticle or populations of nanoparticles. In other embodiments, multiple types of targeting ligands are conjugated to each polymer or nanoparticle or within a population of nanoparticles. In still other embodiments, a single molecular entity of the targeting ligand is conjugated to each individual nanoparticle. The ability to conjugate single molecular entities to individual nanoparticles is described in U.S. patent application Ser. No. 13/782,458, filed Mar. 1, 2013, which is incorporated by reference herein at least for this purpose. In other embodiments, multiple molecules of the targeting ligand are conjugated to each individual nanoparticle As suggested above, in certain embodiments, the polymers, polymer-conjugates, and/or nanoparticles may exist as dispersions in aqueous media, said aqueous media optionally also containing buffers, surfactants, or other modifiers. The present disclosure also contemplates pharmaceutical compositions comprising one or more biologically active agents and any of the polymers or polymer conjugates or nanoparticles or plurality of nanoparticles described herein and a pharmaceutically acceptable vehicle, carrier or excipient.

The term "vehicle" as used herein indicates any of various media acting usually as solvents, carriers, binders, excipients or diluents for a nanoparticle comprised in the composition as an active ingredient.

The term "excipient" as used herein indicates an inactive substance used as a carrier for the active ingredients of a medication. Suitable excipients for the pharmaceutical compositions herein disclosed include any substance that enhances the ability of the body of an individual to absorb the nanoparticle. Suitable excipients also include any substance that can be used to bulk up formulations with nanoparticles to allow for convenient and accurate dosage. In addition to their use in the single-dosage quantity, excipients can be used in the manufacturing process to aid in the handling of nanoparticles. Depending on the route of administration, and form of medication, different excipients may be used. Exemplary excipients include but are not limited to antiadherents, binders, coatings disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluents include any substance that can decrease the viscosity of a medicinal preparation.

Further details concerning the identification of the suitable carrier agent or auxiliary agent of the compositions, and generally manufacturing and packaging of the kit, can be identified by the person skilled in the art upon reading of the present disclosure.

The compositions comprising the biologically active agents and the polymers, polymer conjugates, and/or nanoparticles of the present disclosure, including the pharmaceutical compositions thereof, are useful for treating patients in need of treatment, in particular because of the enhanced bioavailability engendered by the inventive polymers, polymer conjugates, and/or nanoparticles. The degree of the improvement of the bioavailablity of such compositions, relative to the delivery of the same biologically active agent or agents either by itself or with cMAP by itself was surprisingly high. See Examples. Accordingly, important embodiments include those where the compositions comprising the biologically active agents and the polymers, polymer conjugates, and/or nanoparticles of the present disclosure, including the pharmaceutical compositions thereof, are administered to patients in need of the biologically active agents being administered.

The following listing of embodiments is intended to complement, rather than displace or supersede, the previous descriptions.

Embodiment 1

A polymer comprising alternating charged and uncharged segments comprising one or more of the following structural units of Formula (I) or Formula (II) or Formula (III):

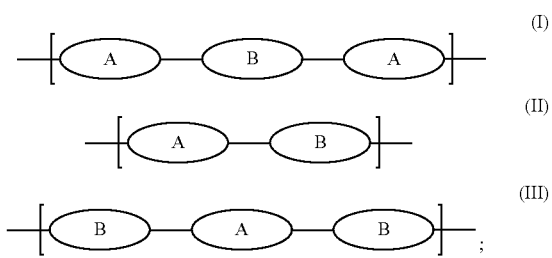

wherein

A is an uncharged segment comprising polyalkylene glycol;

B is a cationically charged segment comprising at least one polyhydroxy linkage comprising at least one pair of vicinal diols. In certain subset embodiments, A and B independently have number average molecular weights in a range 500 Da to about 5000 Da, greater than 5000 da to about 10 kDa, greater than 10 kDa to about 20 kDa, greater than 20 kDa to about 30 kDa, greater than 30 kDa to about 40 kDa, greater than greater than 40 kDa to about 50 kDa, or any combination thereof. In other subsets, either A or B, or both A and B have a number average molecular weight in a range of greater than 5000 Da to about 50,000 Da.

Embodiment 2

The polymer of Embodiment 1, wherein A is or comprises polyethylene glycol and an appropriate linking group.

Embodiment 3

The polymer of Embodiment 1 or 2, wherein the polyalkylene glycol has a nominal number averaged molecular weight in a range of from about 500 Daltons to about 50,000 Daltons. In certain subsets of this Embodiment, the polyalkylene glycol has a nominal number averaged molecular weight in a range of from about 500 Da to about 1 kDa, greater than 1 kDa to about 5 kDa, greater than 5 kDa to about 10 kDa, greater than 10 kDa to about 15 kDa, greater than 15 kDa to about 20 kDa, greater than 20 kDa to about 30 kDa, greater than 30 kDa to about 40 kDa, greater than 40 kDa to about 50 kDa, or any combination of two or more of these ranges.

Embodiment 4

The polymer of any one of Embodiments 1 to 3, where B is a cationically charged segment comprising at least one polyhydroxy sugar linkage comprising at least one pair of vicinal diols.

Embodiment 5

The polymer of any one of embodiments 1 to 4, wherein B comprises at least one repeating subunit comprising a structure of Formula (IV):

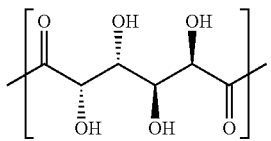

(IV)

Note that the structure designated as

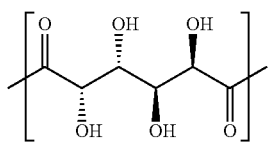

is functionally equivalent to that presented in Formula (IV) and this representation is intended to refer to both.

Embodiment 6

The polymer of any one of Embodiments 1 to 5, wherein B further comprises at least one repeating subunit comprising a structure of Formula (V):

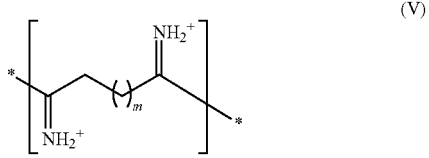

(V)

wherein m is 1, 2, 3, 4, 5, 6, 7, 8, 9, or 10, preferably 4-6 or 5.

Embodiment 7

The polymer of any one of Embodiments 1 to 6, wherein B comprises at least one repeating subunit comprising cMAP, whose subunit structure is represented as Formula (VI):

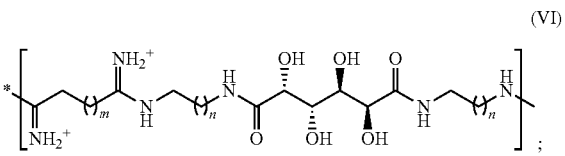

(VI)

wherein
m is independently at each occurrence 1, 2, 3, 4, 5, 6, 7, 8, 9, or 10, preferably 4-6 or 5; and
n is independently at each occurrence 1, 2, 3, 4, or 5. In other related embodiments, m and n can be larger, for example to about 10.

Embodiment 8

The polymer of any one of Embodiments 1 to 7, described by a structure of Formula (VII):

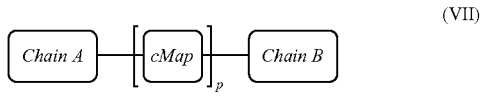

(VII)

wherein
Chain A is

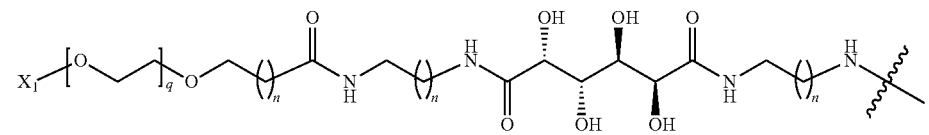

Chain B is

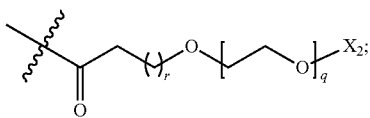

cMAP is

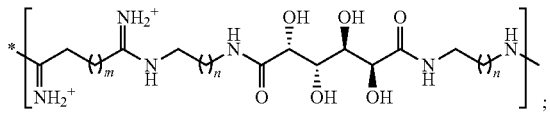

p and q are sufficient to provide a number average molecular weight for the subunits comprising cMAP and PEG, respectively, independently in a range of from about 500 Da to about 50,000 Da;

m is independently at each occurrence 1, 2, 3, 4, 5, 6, 7, 8, 9, or 10, preferably 4-6 or 5;

n and r are independently at each occurrence 0, 1, 2, 3, 4, or 5; and $X_1$ and $X_2$ are independently at each occurrence $C_{1-6}$ alkyl, optionally substituted with —OH, —COOH, —C(=O)O(alkyl), —C(=O)O(aryl), —NH$_2$, —NH(alkyl), —N(alkyl)$_2$, or a salt or protected analog thereof.

Note that, to meet the molecular weight restrictions, the numeric values for p corresponds to a range of from about 1 to about 100, preferably from about 10 to about 100, and the numeric values for q corresponds to as range from about 12 to about 1200. In subsets of these embodiments, q can also be in a range of from about 100 to about 500. In certain subsets of this Embodiment, p and q are sufficient to provide a number average molecular weight for the subunits comprising cMAP and PEG, respectively, independently in a range of from about 500 Da to about 1000 Da, greater than 1000 Da to about 5000 Da, greater than 5000 Da to about 10,000 Da, greater than 10,000 to about 25,000 Da, greater than 25,000 Da to about 50,000 Da, or any combination of two or more of these ranges, as well as the corresponding numeric values for these MW$_n$ ranges. In other subsets of this Embodiment, $X_1$ and $X_2$ are independently —(CH$_2$)$_{1-4}$—COOH and —(CH$_2$)$_{1-4}$—NH$_2$ Embodiment 9

The polymer of any one of Embodiments 1 to 7, described by a structure of Formula (VII):

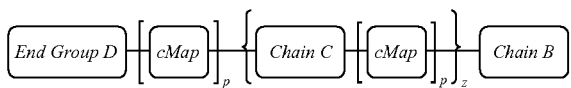

(VIII)

wherein cMAP is

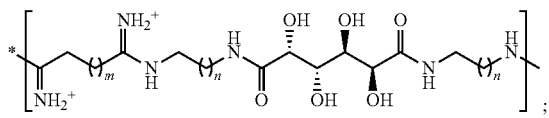

Chain B is

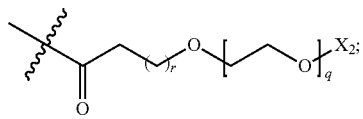

Chain C is

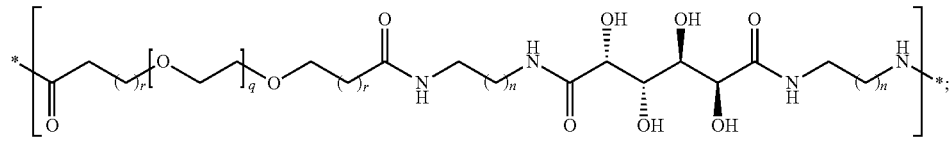

End Group D is:

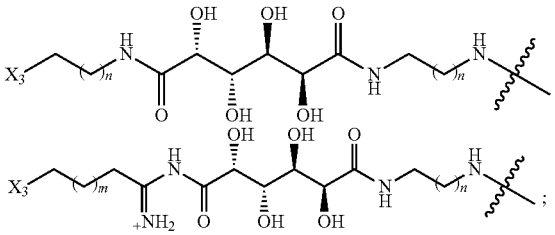

p and q are sufficient to provide a number average molecular weight for the subunits comprising cMAP and PEG, respectively, independently in a range of from about 500 Da to about 50,000 Da;

m is independently at each occurrence 1, 2, 3, 4, 5, 6, 7, 8, 9, or 10, preferably 4-6 or 5;

n and r are independently at each occurrence 0, 1, 2, 3, 4, or 5;

z is equal to or greater than 1 (up to about 2, 4, 6, 8, or 10); and $X_2$ is independently at each occurrence $C_{1-6}$ alkyl, optionally substituted with —OH, —COOH, —C(=O)O(alkyl), —C(=O)O(aryl), —NH$_2$, —NH(alkyl), —N(alkyl)$_2$, or a salt or protected analog thereof and.

$X_3$ is —OH, —COOH, —C(=O)O(alkyl), —C(=O)O(aryl), —NH$_2$, —NH(alkyl), —N(alkyl)$_2$, or a salt or protected analog thereof.

Again, as in Embodiment 9, to meet the molecular weight restrictions, the numeric values for p corresponds to a range of from about 1 to about 100, preferably from about 10 to about 100, and the numeric values for q corresponds to as range from about 12 to about 1200. In subsets of these embodiments, q can also be in a range of from about 100 to about 500. In certain subsets of this Embodiment, p and q are sufficient to provide a number average molecular weight for the subunits comprising cMAP and PEG, respectively, independently in a range of from about 500 Da to about 1000 Da, greater than 1000 Da to about 5000 Da, greater than 5000 Da to about 10,000 Da, greater than 10,000 to about 25,000 Da, greater than 25,000 Da to about 50,000 Da, or any combination of two or more of these ranges, as well as the corresponding numeric values for these $MW_n$ ranges. In other subsets of this Embodiment, $X_1$ and $X_2$ are independently —$(CH_2)_{1-4}$—COOH and —$(CH_2)_{1-4}$—$NH_2$ Embodiment 10

The polymer of any one of Embodiments 1 to 7, described by a structure of Formula (IX):

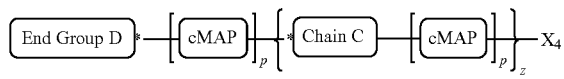

wherein
End Group D is:

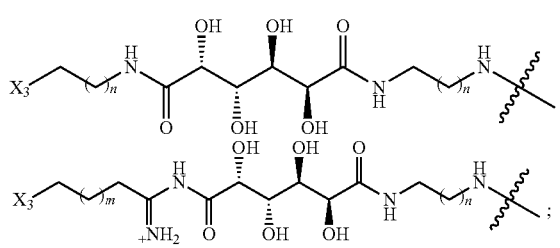

cMAP is

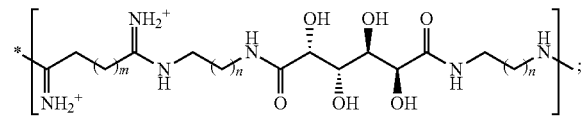

Chain C is

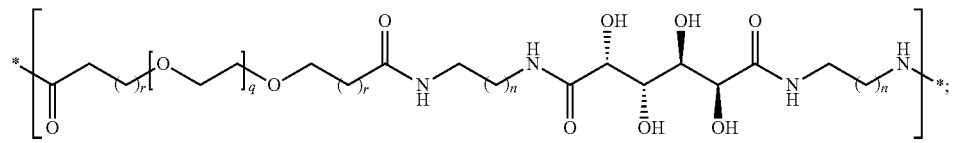

p and q are sufficient to provide a number average molecular weight for the subunits comprising cMAP and PEG, respectively, independently in a range of from about 500 Da to about 50,000 Da, preferably from about 1000 Da to about 5000 Da;

m is independently at each occurrence 1, 2, 3, 4, 5, 6, 7, 8, 9, or 10, preferably 4-6 or 5;
n and r are independently at each occurrence 0, 1, 2, 3, 4, or 5;
z is equal to or greater than 1 (up to about 2, 4, 6, 8, or 10); and
$X_3$ and $X_4$ are independently at each occurrence —OH, —COOH, —C(=O)O(alkyl), —C(=O)O(aryl), —$NH_2$, —NH(alkyl), —N(alkyl)$_2$, or a salt or protected analog thereof.

Again, as in Embodiments 9 and 10, to meet the molecular weight restrictions, the numeric values for p corresponds to a range of from about 1 to about 100, preferably from about 10 to about 100, and the numeric values for q corresponds to as range from about 12 to about 1200. In subsets of these embodiments, q can also be in a range of from about 100 to about 500. In certain subsets of this Embodiment, p and q are sufficient to provide a number average molecular weight for the subunits comprising cMAP and PEG, respectively, independently in a range of from about 500 Da to about 1000 Da, greater than 1000 Da to about 5000 Da, greater than 5000 Da to about 10,000 Da, greater than 10,000 to about 25,000 Da, greater than 25,000 Da to about 50,000 Da, or any combination of two or more of these ranges, as well as the corresponding numeric values for these $MW_n$ ranges. In other subsets of this Embodiment, $X_1$ and $X_2$ are independently —$(CH_2)_{1-4}$—COOH and —$(CH_2)_{1-4}$—$NH_2$ Embodiment 11

The polymer of any one of Embodiments 6 to 10, wherein m is 4, 5, or 6, preferably 5.

Embodiment 12

The polymer of any one of Embodiments 7 to 11, wherein n is 1.

Embodiment 13

The polymer of any one of Embodiments 7 to 12, wherein r is 2, 3, or 4, preferably 3.

Embodiment 14

The polymer according to any one of Embodiments 8 to 13, wherein p is sufficient to provide a number average molecular weight of the subunit comprising cMAP in a range of from about or greater than 5 kDa to about 15 kDa, from about or greater than 6 kDa to about 14 kDa, from about or greater than 7 kDa to about 13 kDa, from about or greater than 8 kDa to about 12 kDa, from about or greater than 9 kDa to about 11 kDa, or about 10 kDa. In some subset Embodiments, for example where the cMAP fragment has $MW_n$ of about 420 Da, this corresponds to p having numeric values in ranges of about 12 to about 36, from about 14 to about 33, from about 17 to about 31, from about 19 to about 29, from about 22 to about 26, or about 24.

Embodiment 15

The polymer according to any one of Embodiments 8 to 13, wherein q is sufficient to provide a number average molecular weight of the subunit comprising PEG in a range of from about or greater than 500 Da to about 50 kDa, from about or greater than 1 kDa to about 40 kDa, from about or greater than 5 kDa to about 30 kDa, or from about or greater than 5 kDa to about 20 kDa. In some of these Embodiments, for example assuming ethylene glycol fragment has $MW_n$ of about 44 Da, this corresponds to q having numeric values in ranges of about 11 to about 1200, from about 23 to about 910, from about 110 to about 680, or from about 110 to about 450.

Embodiment 16

A polymer conjugate comprising a polymer of any one of Embodiments 1 to 15 and a second boronic acid-containing polymer comprising a structure of Formula (X)

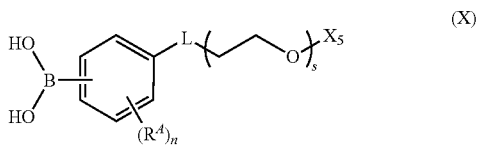

wherein
the polymer and the second boronic acid-containing polymer are reversible connected to one another by a borate condensation linkage between the boronic acid moieties of Formula (IX) and at least one pair of vicinal diols of the polyhydroxy linkages of Formula (I), (II), (III), (IV), (VI), (VII), (VIII), or (IX), $X_5$ being at the distal end of this connection;

$R^A$ is nitro (or other electron withdrawing group);
n is 0, 1, 2, 3, or 4, preferably 1;
s is 20-1200;
L is a linking group between the phenyl ring and the polyethylene oxide linkage; and
$X_5$ is $C_{1-6}$ alkyl, optionally substituted with —OH, —COOH, —C(=O)O(alkyl), —C(=O)O(aryl), —NH$_2$, —NH(alkyl), —N(alkyl)$_2$, or a salt or protected analog thereof. Exemplary structures to be provided as:

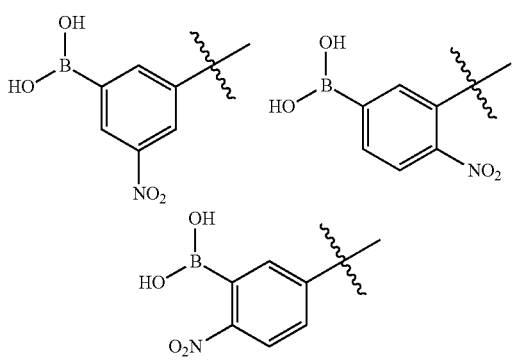

Embodiment 17

The polymer conjugate of Embodiment 16, wherein L is —(C$_{0-2}$alkylene-)NH—C(=O)—(C$_{0-2}$alkylene)-, —(C$_{0-2}$alkylene)-C(=O)—NH—(C$_{0-2}$alkylene)-, —(C$_{0-2}$alkylene)-O—C(=O)—(C$_{0-2}$alkylene)- or —(C$_{0-2}$alkylene)-C(=O)—O—(C$_{0-2}$alkylene)-.

Embodiment 18

The polymer conjugate of Embodiment 17, wherein L is —NH—C(=O)—, —C(=O)—NH—, —O—C(=O)—, or —C(=O)—O—.

Embodiment 19

A nanoparticle comprising a polymer of any one of Embodiments 1 to 15.

Embodiment 20

A nanoparticle comprising a polymer conjugate of any one of Embodiments 16 to 18.

Embodiment 21

The nanoparticle of any one of claims 10 to 16, said nanoparticle being substantially spherical and having a cross-section dimension in a range of from about 20 nm to about 300 nm.

Embodiment 22

A plurality of nanoparticles, each individual nanoparticle being described by the composition of any one of Embodiments 19 to 21.

Embodiment 23

A plurality of nanoparticles, each individual nanoparticle being described by the composition of any one of Embodiments 19 to 22, the plurality of nanoparticles being substantially monodispersed, exhibiting a standard deviation in cross-sectional dimension (i.e., diameter) among the nanoparticles of less than 20%, 30%, 40%, 50%, or 60%, as measured by cryo-transmission electron microscopy (cryo-TEM).

Embodiment 24

A nanoparticle comprising a polymer of any one of Embodiments 1 to 15 or a polymer conjugate of claims 16 to 18, further comprising an encapsulated biological agent.

Embodiment 25

The nanoparticle of Embodiment 24, wherein the biological agent is covalently bound to the polymer or polymer conjugate.

Embodiment 26

The nanoparticle of Embodiment 24 or 25, wherein the biological agent is a polynucleotide or a small molecule therapeutic agent.

Embodiment 27

The nanoparticle of Embodiment 24 or 25, wherein the biological agent is a polynucleotide that is an RNA molecule.

Embodiment 28

The nanoparticle of Embodiment 27, wherein the RNA molecule is an siRNA molecule.

Embodiment 29

The nanoparticle of any one of claims 20 to 28, further conjugated to a targeting ligand, wherein conjugation occurs through a condensation linkage between the distal end of the boronic acid-containing polymer and the targeting ligand.

Embodiment 30

The nanoparticle of Embodiment 29, wherein a single targeting ligand is conjugated to each polymer.

Embodiment 31

The nanoparticle of Embodiments 29, wherein a plurality of targeting ligands is conjugated to each polymer.

Embodiment 32

A pharmaceutical composition comprising a biologically active agent and the polymer or polymer conjugate of any one of claims 1 to 18 and a pharmaceutically acceptable carrier or excipient.

Embodiment 33

A pharmaceutical composition comprising a biologically active agent and the nanoparticle or plurality of nanoparticles of any one of Embodiments 19 to 31 and a pharmaceutically acceptable carrier or excipient.

Embodiment 34

A method comprising administering the nanoparticles of any one of Embodiments 24 to 28 to a patient, wherein the bioavailability of the biological agent is improved relative to an administration of the biological agent by itself.

Embodiment 35

A method of preparing a polymer of any one of Embodiments 1 to 15 comprising covalently connecting at least one uncharged segment comprising polyalkylene glycol with at least one cationically charged segment comprising at least one polyhydroxy linkage through the use of at least one linking group. Exemplary methods are provided in the Examples and Appendices. These methods which include reacting homologs of the specific reactants cited are also considered within the scope of the present disclosure.

Embodiment 36

The method of Embodiment 35, wherein the at least one polyhydroxy linkage comprises mucic acid and at least one linking group is an amide.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric. Any reference to molecular weight, unless said otherwise, is intended to refer to number average molecular weight.

Summary of Experimental Results

A new cationic polymer that possesses repeat units based on mucic acid and dimethyl suberimidate was synthesized and denoted cMAP. Further modification of cMAP into a triblock polymer with mPEG flanking cMAP, mPEG-cMAP-PEGm, resulted in a well-defined polymer with a molecular weight of ca. 20 kDa. This triblock polymer was able to fully encapsulate siRNA at charge ratios of 2+/− or greater. Stable NPs composed of this triblock polymer and siRNA can be formulated directly in PBS with diameters of ca. 30 nm (by both DLS and CryoTEM), and slightly positive surface charge of ca. 0.4 mV in both 10 mM phosphate buffer pH 7.4 and 1 mM KCl pH 5.5. Upon injection into mice, these NPs formed with the mPEG-cMAP-PEGm triblock polymer showed prolonged circulation compared to NPs formulated with cMAP and cMAP-PEG copolymer, with 5-10% of the formulation remaining in the circulation after 1 hour. The circulation time remained the same when a portion of the excess triblock polymer is removed from the formulation. The absence of any excess cationic polymer is advantageous to minimize any adverse effects that these entities cause in vivo.

Example 1. Materials and Methods

Mucic acid and oxalyl chloride were purchased from Sigma-Aldrich, N-boc-ethylenediamine from AK Scientific, dimethyl suberimidate from Thermo Fisher Scientific or Sigma-Aldrich, and 3-carboxyl-5-nitrophenyl boronic acid from Alfa-Aesar. Polyethylene glycol reagents were purchased from either Jenkem Technology USA or Laysan Bio, Inc. Dimethyl suberimidate, the charged monomer with which mucic acid ethylenediamine was polymerized, was used as purchased from Thermo Scientific or Sigma-Aldrich. In order to assign peaks in the proton and carbon spectra of cMAP, NMR spectra of dimethyl suberimidate were acquired. Both proton and carbon NMR spectra of DMS were more complex than expected, suggesting that some hydrolysis was present in a freshly opened bottle. See Table 2.

Nuclear magnetic resonance (NMR) spectra were acquired on Varian 300 MHz, 500 MHz, or 600 MHz instruments at 25 degrees Celsius, without spinning, at 500 or 600 MHz. For most $^1$H proton spectra, a delay time of 1-1.5 s was used; for quantitative integration of the polymer, a 25 s delay was used. $^{13}$C carbon spectra were acquired at 500 MHz with default settings. $^1$H-$^{13}$C heteronuclear single quantum coherence (HSQC), $^1$H-$^1$H correlation spectroscopy (COSY), and $^1$H-$^{13}$C heteronuclear multiple-bond correlation spectroscopy (HMBC) spectra using default VNMRJ3.0 HSQCAD, COSY, and HMBC settings were acquired. Additionally, diffusion ordered spectroscopy (DOSY) spectra using the bipolar pulse pair stimulated echo with convection compensation (Dbppste cc) method in VNMRJ3.0 with diffusion gradient length of 4.0 ms and diffusion delay of 100.0 ms was acquired for synthesized polymers.

Electrospray ionization masses of small molecules were acquired using a Finnigan LCQ ion trap mass spectrometer. Matrix-assisted laser desorption/ionization-time of flight (MALDI-TOF) mass spectra for polymers were acquired on an Applied Biosystems Voyager DE-PRO using a 10 mg/mL alpha-cyano-4-hydroxycinnamic acid matrix.

Example 2. Synthesis of the Mucic Acid Containing Polymers

Example 2.1. Synthesis of cationic Mucic Acid Polymer (cMAP) (FIG. 1)

Methanol (360 mL) was added to mucic acid (15 g, 71 mmol, 1 equiv) in a 500 mL round bottom flask containing a stir bar. Concentrated sulfuric acid (1.2 mL, 22.5 mmol, 0.3 equiv) was added to this suspension, which was then stirred overnight and refluxed at 85° C. The mixture was cooled to room temperature and filtered through a Buchner funnel using Whatman #5 filter paper. The solid was washed with 600 mL of methanol and then returned to the 500 mL round bottom flask. 240 mL of methanol and 1.5 mL of triethylamine were added and the solid was recrystallized at 85° C. reflux for 1 h. The mixture was cooled to room temperature, filtered through a Buchner funnel, and washed with 600 mL of methanol. The solid was dried under vacuum at 75° C. overnight to afford mucic acid dimethyl ester (13.72 g, 80% yield), a white solid. $^1$HNMR (300 MHz, DMSO-$d_6$): 4.91 (d, 2H), 4.80 (q, 2H), 4.29 (d, 2H), 3.76 (q, 2H), 3.62 (s, 6H).

Methanol (220 mL) was added to mucic acid dimethyl ester (13.72 g, 57.6 mmol, 1 equiv) in a 500 mL round bottom flask containing a stir bar. Triethylamine (20.9 mL, 150 mmol, 2.6 equiv) was added and the mixture was stirred and refluxed at 85° C. for 30 min, during which time a yellow suspension formed. N-boc-ethylenediamine (23.7 mL, 150 mmol, 2.6 equiv) in methanol (55 mL) was added to the suspension and stirring and refluxing at 85° C. was resumed overnight. The mixture was cooled to room temperature and filtered through a Buchner funnel using Whatman #5 filter paper. The solid was washed with methanol (750 mL) and recrystallized with methanol (350 mL) at 85° C. for 1.5 h. The mixture was again cooled to room temperature, filtered through a Buchner funnel, and washed with methanol (750 mL). The solid was dried under vacuum at 75° C. overnight to afford N-boc protected mucic acid ethylenediamine (19.27 g, 68% yield), a white solid. $^1$H NMR (300 MHz, DMSO-d6): 7.71 (t, 2H), 6.81 (t, 2H), 5.13 (d, 2H), 4.35 (q, 2H), 4.10 (d, 2H), 3.77 (q, 2H), 3.13 (m, 4H), 2.97 (m, 4H), 1.36 (s, 18H). ESI 495.1 [M+H]$^+$, 517.4 [M+Na]$^+$.

N-boc protected mucic acid ethylenediamine (19.2 g) in a 500 mL round bottom flask with a stir bar was placed in a water bath. Methanol (260 mL), followed by concentrated 12 N hydrochloric acid (65 mL), was added to the flask to make 3 N HCl in methanol. The reaction flask was sealed with a septum and vented with a needle. The water bath was set to 25° C. and the suspension was stirred for 6-8 h. The reaction was monitored by thin layer chromatography (TLC) with a mobile phase of 1% methanol in $CH_2Cl_2$ and the spots were visualized in an iodine tank. Reaction completion was also confirmed by ESI. The slurry was filtered through a glass frit with a fine grain and washed with methanol (750 mL) until the filtrate was close to a neutral pH. The solid was dried under vacuum at 80° C. overnight to afford mucic acid ethylenediamine (12.96 g, 91% yield) as a white solid. $^1$H NMR (500 MHz, DMSO-d6): 7.97-7.83 (m, 8H), 5.30 (d, 2H), 4.55 (d, 2H), 4.16 (d, 2H), 3.82 (m, 2H), 2.85 (m, 4H). $^{13}$C NMR (500 MHz, DMSO-d6): 174.79, 71.39, 70.98, 39.25, 36.76. ESI 295.1 [M+H]$^+$, 588.93 [2M+H]$^+$.

Mucic acid ethylenediamine (100 mg, 0.3 mmol, 1 equiv) was added to a 4 mL glass vial with a stir bar. 0.5 M sodium carbonate solution in nanopure water (1 mL) was added to the vial and the solution was stirred for 5 min. Dimethyl suberimidate (DMS) (74.4 mg, 0.3 mmol, 1 equiv) was then added to the mixture and the reaction was stirred for 16 h overnight at 25° C. The reaction was diluted with nanopure water (10 mL) and 1N HCl was added drop wise to adjust the pH to 4. The resulting solution was dialyzed with a 15 mL Amicon Ultra 3 kD spin filter against nanopure water until the filtrate pH was neutral. The solution of polymer was concentrated to 3-4 mL, filtered through a 0.2 um PVDF syringe filter into a pre-weighed 20 mL glass vial, and lyophilized to dryness to afford cationic mucic acid polymer (29.2 mg, 16% yield) as a white solid, which was stored under argon at −20° C. $^1$HNMR (600 MHz, DMSO-d6): 9.59-8.74, 7.92, 5.40, 4.53, 4.16, 3.82, 3.55, 3.26, 2.86-2.00, 1.60, 1.28. $^{13}$C NMR (125 MHz, DMSO-d6): 174.61, 168.12, 71.19, 70.96, 51.67, 42.09, 36.71, 32.48, 27.84, 26.65.

Figure 2:
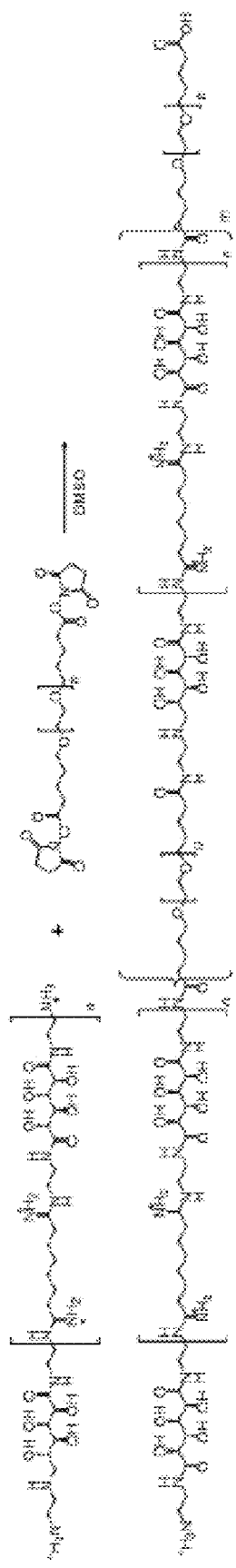
FIG. 2 shows a schematic representation of a synthesis of cMAP-PEG copolymer.

Example 2.2. Synthesis of cMAP-PEG Copolymer (FIG. 2)

Starting materials were equilibrated to room temperature for 1 h after removing them from the −20° C. freezer. cMAP (50 mg, 0.009 mmol, 2 equiv) and di-SPA-PEG-3.5 kD (succinimidyl propionic acid ester, 15.7 mg, 0.0046 mmol, 1 equiv) were weighed into an oven-dried 10 mL flask with stir bar. The flask was capped with a septum, the two solids were dried under vacuum for 1 h. and then the flask was filled with argon. Anhydrous DMSO (2 mL) was added using a needle and syringe to dissolve the two white solids, and the solution was stirred for 24 h. Nanopure water (20 mL) was added to dilute the DMSO, and the solution was dialyzed against nanopure water using a 10 kD MWCO Amicon Ultra filter >8 times. The retentate, cMAP-PEG3.4k copolymer, was filtered through a 0.2 urn PVDF membrane and lyophilized to a white powder (29.6 mg, 45% yield). $^1$H NMR (600 MHz, DMSO-d6): 9.84-8.48, 7.90, 5.41, 4.53, 4.15, 3.82, 3.55, 3.49 (PEG), 3.26, 2.86-2.00, 1.59, 1.27. $^{13}$C NMR (125 MHz, DMSO-d6): 174.66, 168.17, 71.24, 71.00, 70.24, 67.22, 51.69, 42.11, 36.75, 32.58, 27.89, 26.66. A similar procedure was followed using 5 kD di-SVA-PEG (succinimidyl valeric acid ester) to synthesize cMAP-PEG5k copolymer using a 15 kD SpectraPor 7 MWCO membrane (Spectrum Labs) for dialysis.

The cMAP-PEG-cMAP Triblock Polymer was isolated from the cMAP-PEG copolymer by fractionation through centrifugal spin filters of various MWCO. cMAP-PEG3.4k copolymer was dialyzed using a 20 kD MWCO centrifugal spin filter, and the filtrate was then dialyzed through a 10 kD MWCO spin filter to isolate cMAP-PEG3.4K-cMAP, which was filtered through a 0.2 um PVDF membrane and lyophilized to a white powder (10.6 mg, 16% yield). cMAP-PEG5k-cMAP was isolated in the same way.

Example 2.3

Figure 3:
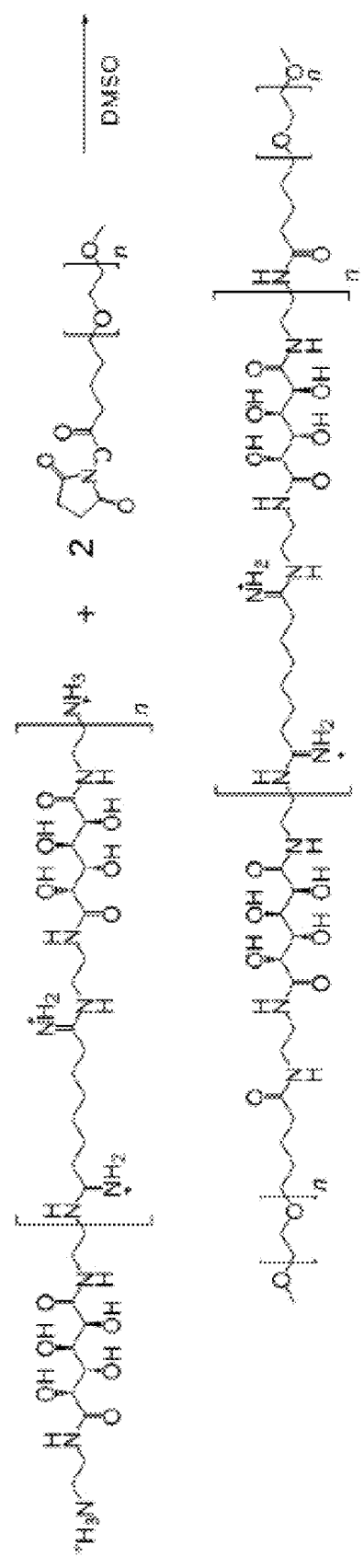
FIG. 3 shows a schematic representation of a synthesis of mPEG-cMAP-PEGm triblock. polymer.

Synthesis of mPEG-cMAP-PEGm triblock polymer (FIG. 3). Starting materials were equilibrated to room temperature for 1 h after removing them from the −20° C. freezer. cMAP (40 mg, 0.006 mmol, 2 equiv) and mPEG5k-SVA (85.7 mg, 0.017 mmol, 3 equiv) were weighed into an oven-dried 10 mL flask with stir bar. The flask was capped with a septum, the two solids were dried under vacuum for 1 h, and then the flask was filled with argon. Anhydrous DMSO (4 mL) was added using a needle and syringe to dissolve the two white solids, and the solution was stirred for 48 h. Nanopure water (40 mL) was added to dilute the DMSO, and the solution was dialyzed against nanopure water using a 20 kD MWCO centrifugal spin filter >8 times. The retentate, mPEG5k-cMAP-PEG5 km, was filtered through a 0.2 um PVDF membrane and lyophilized to a white powder (11.3 mg, 9% yield). $^1$H NMR (600 MHz, DMSO-d6): 9.84-8.48, 7.90, 5.41, 4.53, 4.15, 3.82, 3.55, 3.49 (PEG), 3.26, 3.20, 2.86-2.00, 1.59, 1.27.

A similar procedure was followed using 2 kD mPEG-SVA to synthesize mPEG-cMAP-PEGm with 2 kD blocks. For 2 kD PEG, a 10 kD MWCO centrifugal spin filter was used to isolate the triblock polymer.

Figure 4:
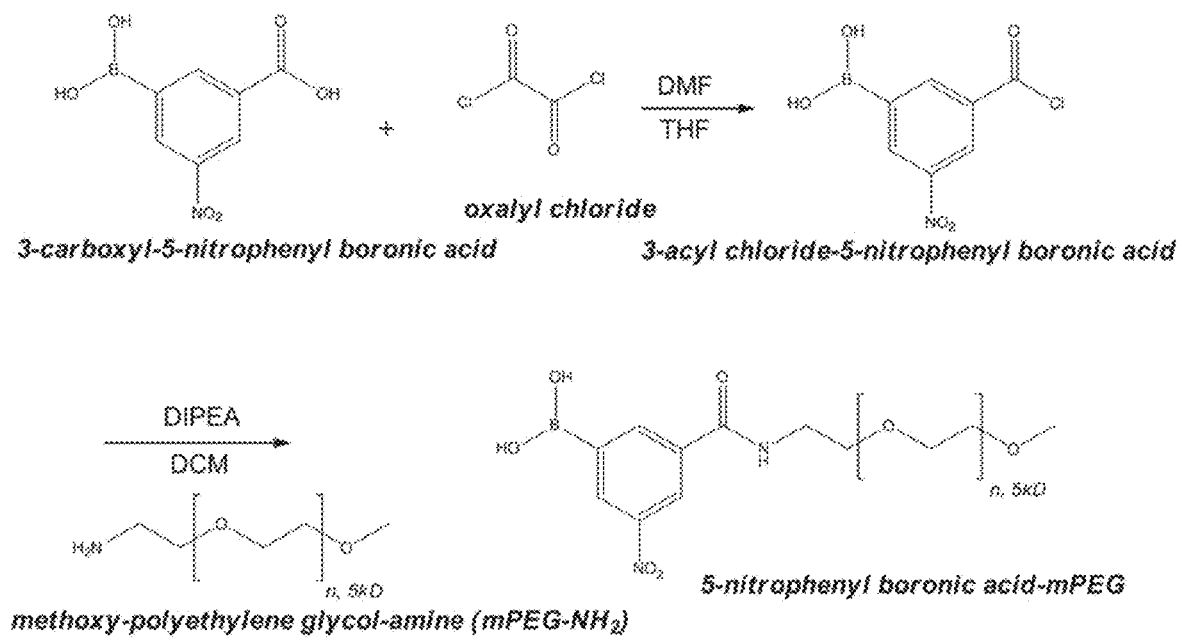
FIG. 4 shows a schematic representation of a synthesis of 5-nitrophenylboronic acid-PEGm.

Example 2.4. Synthesis of 5-Nitrophenylboronic Acid-PEGm (5-nPBA-PEGm) (FIG. 4)

3-carboxyl-5-nitrophenylboronic acid (200 mg, 0.95 mmol, 1 equiv) was added to an oven-dried 2-necked 10 mL round bottom flask containing a dry stir bar. The flask was vented with argon and sealed with a rubber septum. Anhydrous tetrahydrofuran with BHT inhibitor (5 mL) was added to dissolve the boronic acid, followed by anhydrous DMF (14.7 µL, 0.19 mmol, 0.2 equiv). The flask was cooled to 0° C. in an ice-water bath. Oxalyl chloride (195.4 µL, 2.28 mmol, 2.4 equiv) was then added drop wise to the reaction mixture. The ice-water bath was removed after oxalyl chloride addition was complete, and the reaction continued stirring for 2 hours at room temperature, with an argon vent to allow for the escape of volatiles. Solvent and DMF was removed via rotary evaporator and then under vacuum for 2 days under dark to afford 3-acyl chloride-5-nitrophenyl boronic acid (217.5 mg, 100% yield) as a yellow solid. 3-acyl chloride-5-nitrophenylboronic acid (27.5 mg, 0.12 mmol, 2 equiv) was added to an oven-dried 25 mL round bottom flask containing a dry stir bar. The flask was sealed with a rubber septum, vented with argon, and cooled to 0° C. in an ice-water bath. Anhydrous dichloromethane (4 mL) was added to dissolve the boronic acid. 5 kD mPEG-amine (300 mg, 0.06 mmol, 1 equiv) in an oven-dried 10 mL round bottom flask vented with argon, dissolved in anhydrous dichloromethane (5 mL) and diisopropylethylamine (DIPEA, 20.9 µL, 0.12 mmol, 2 equiv) dried with activated molecular sieves, was slowly added to the boronic acid solution. The reaction flask was left in the ice-water bath to slowly warm up to room temperature, and the reaction was stirred overnight under dark. The solvent and DIPEA was removed via rotary evaporator and then under vacuum for 2 days under dark. The solid residue was reconstituted in 0.5 N HCl (5 mL) and stirred for 15 min. The resulting suspension was filtered through a 0.2 um Supor syringe filter, and the resulting clear solution was dialyzed with a 15 mL Amicon Ultra 3 kD spin filter against nanopure water until the pH was constant. The solution of polymer was concentrated to 3-4 mL, filtered through a 0.2 um PVDF syringe filter into a pre-weighed 20 mL glass vial, and lyophilized to dryness to afford 5-nitrophenylboronic acid-PEGm (219.2 mg, 70% yield) as a fluffy white solid. $^1$H NMR (600 MHz, DMSO-d6): 8.89 (t, 1H), 8.72 (m, 1H), 8.68 (m, 1H), 8.64 (m, 1H), 8.60 (s, 2H), 3.5 (s-PEG, 510H), 3.22 (s, 3H). $^{11}$B NMR (160 MHz, 10 mM phosphate buffer, pH 7.4 in D20): 11.26 (broad s). MALDI: 5825.5.

Example 3. Polymer Characterization

Example 3.1. Gel Permeation Chromatography

An Agilent 1100 HPLC with binary pump and injector was connected to a Tosoh TSKgel G3000PWXL-CP size exclusion column with Wyatt DAWN HELEOS light scattering and Wyatt Optilab Rex refractive index detection. Lyophilized polymer was dissolved at six different concentrations in 0.1 M NaNO3 and injected into the refractive index detector directly via a syringe pump for do/dc determination. For absolute molecular weight determination by light scattering, 100 µL of polymer solution was injected onto the column and the detected polymer peak analyzed using ASTRA V software.

Example 3.2. TNBSA Assay of cMAP for Primary Amines

The instructions provided by Thermo Scientific with the 2,4,6-trinitrobenzene Sulfonic Acid 5% w/v in methanol stock solution were followed, with modifications as described next. Briefly, cMAP and glycine were each dissolved in the reaction buffer and serially diluted for a concentration range of 2 to 0.0039 mg/mL and 20 to 0.00195 mg/mL, respectively. 100 µL of each sample concentration and 50 µL of TNBSA working solution were added to a 96-well plate in triplicates and briefly shaken. The absorbance was read on a Tecan infinite M200 plate reader at a wavelength of 335 nm, incubated at 37 degrees Celsius for 2 h, and read again. Glycine was used as a positive control.

Example 3.3. Polymer siRNA Encapsulation Assays

The ability of the cMAP polymers to encapsulate siRNA was analyzed using two methods: a gel retardation assay and a RiboGreen assay. For the gel retardation assay, increasing volumes of 0.5 mg/mL polymer was mixed with 1 µL of 1 mg/mL siRNA at (+/−) charge ratios of 0, 0.5, 1, 1.5, 2, 2.5, 3, and 5 in water for a total volume of 15 µL. The mixtures were briefly vortexed, centrifuged down, and allowed to sit for 15 min at room temperature. 3 µL of 6×DNA loading dye was added to each mixture, which was then loaded onto a 1 wt % agarose gel and run at 95V for 1.5 h in 0.5×TBE buffer. The gel was imaged on a UVP BioDoc-It Imaging System.

The RiboGreen assay was performed in a similar manner to the gel retardation assay, except using increasing volumes of 0.1 mg/mL polymer and 1 µL of 0.1 mg/mL siRNA in water for a total volume of 100 µL in 96-well plate. To each of these mixtures, 100 µL of the Quant-iT RiboGreen RNA reagent working solution, prepared according to the kit's protocol, was added. The plate was briefly shaken, incubated in the dark for 5 min at room temperature, and the fluorescence intensity read on a Tecan infinite M200 plate reader at an excitation wavelength of 480 nm and an emission wavelength of 520 nm. Measurements were done in triplicate.

Example 4. Nanoparticle Formulation and Characterization

Example 4.1. Nanoparticle Formulation cMAP NPs were formulated by first mixing a 1:1 molar ratio of cMAP vicinal diols to 5-nPBA-PEGm (1 mg cMAP to 22 mg 5-nPBA-mPEG) in 10 mM phosphate buffer pH 7.4, briefly vortexing, centrifuging down, and letting the mixture sit for 15 min at room temperature. siRNA in an equivalent volume of RNAse-free water was then added at a 3:1 charge ratio of cMAP to siRNA, and at a concentration of up to 0.8 mg/mL siRNA. cMAP-PEG copolymer, cMAP-PEG-cMAP triblock, and mPEG-cMAP-PEGm triblock formulations were made in a similar fashion, though the charge ratio was varied from 3:1 down to a 1:1 charge ratio of polymer to siRNA, and at a concentration of up to 1 mg/mL siRNA. For formulations without any 5-nPBA-PEGm, the polymer and siRNA in equal volumes were simply mixed at an appropriate charge ratio. For injection into mice, 0.1 volumes of 10× phosphate buffered saline (PBS) were added to attain a 1×PBS solution, with a final concentration of 0.73 mg/mL siRNA. For the cMAP-PEG copolymer and mPEG-cMAP-PEGm NPs which were formulated in PBS, both the polymer and siRNA solutions were in PBS, and then mixed together; this was able to be directly injected into mice. For removal of excess components (i.e., polymer, PEG), the NP formulation was placed in a 0.5 mL 30 kD MWCO Amicon Ultra spin filter and dialyzed with PBS at 2,000 rpm for 10 min 5-10 times.

Example 4.2. Nanoparticle Size and Zeta Potential

NP size was determined using two different methods: dynamic light scattering (DLS) and cryo-transmission electron microscopy (cryoTEM). DLS was performed on a Brookhaven Instruments Corporation (BIC) Zeta-PALS with BIC Particle Sizing Software. The particles were diluted down to a concentration of 0.2 mg/mL siRNA or less, depending on the formulation, until a stable size was recorded for ten 1-minute measurements. The results of at least 10 measurements were averaged.

CryoTEM imaging was performed on particles in solution that were frozen on R2/2 Quantifoil grids in liquid ethane after blotting with filter paper using an FEI Mark IV Vitrobot with a 2 s blot time (blot force 6) and a 1 s drain time. Images were collected on a Tecnai 120-keV transmission electron microscope equipped with a Gatan 2k×2k UltraScan CCD camera and Serial EM automated software. Acquired images were analyzed using ImageJ software to measure NP diameter.

The NPs' surface charge, or zeta potential, was measured using the same Zeta-PALS used for DLS, with the addition of a Brookhaven aqueous electrode assembly. 10 µL of particle formulation was mixed with 1.5 mL of either 10 mM phosphate buffer, pH 7.4 or 1 mM potassium chloride, pH 5.5 in a cuvette. The electrode was inserted into the cuvette and zeta potential measured using BIC PALS Zeta Potential Analyzer software with a target residual of 0.012. The results of at least 10 measurements were averaged.

Example 4.3. Nanoparticle Stoichiometry

Example 4.3.1. Quantification of 5-nPBA-PEGm Bound to NP

NPs were formulated with 5-nPBA-PEGm and excess components were removed as described above. 50 µL of filtrate from the 30 kD MWCO spin filter (containing excess components) were injected on an Agilent 1200 HPLC with quaternary pump and autosampler connected to a Phenomenex Gemini C18 reverse phase column and multiple wavelength detector. The absorbance at 254 nm was recorded and compared with a calibration curve of 5-nPBA-PEGm.

Example 4.3.2. Quantification of Cationic Polymer Bound to NP

NPs were formulated in the absence of 5-nPBA-PEGm. For cMAP, excess cationic polymer was removed from aggregated NPs as described above. The cationic polymer bound to the NP was directly quantitated by taking the retentate from the 30 kD MWCO spin filter containing the NPs, and disassembling and sequestering the siRNA using BcMag SAX (Strong Anion Exchange) magnetic beads (Bioclone Inc). 50 µL of the liquid containing cMAP was injected onto the GPC setup described above and the amount of polymer bound to the NP was directly determined using the refractive index signal as compared to a cMAP calibration curve. For cMAP-PEG copolymer and mPEG-cMAP-PEGm, 50 µL of the formulation was injected onto the GPC setup described above. The refractive index signal corresponding to polymer not bound to the NP was recorded and compared with a calibration curve of the same cationic polymer. This amount was subtracted from the total amount of polymer used for the formulation to determine the percent of polymer bound to the NP.

Example 5. In Vivo Mouse Pharmacokinetic (PK) Studies

All animal studies were approved by the Institutional Animal Care and Use Committee at Caltech. NPs were formulated as described above, except 20% of the siRNA was substituted with a Cy3-fluorophore tagged siRNA. The NP formulation was injected intravenously via the mouse tail vein at a dose of 5 mg siRNA per kg mouse. The hind legs of Balb/c mice (Taconic and Jackson Labs) were shaved for blood collection from the saphenous vein in red top clot activator containing Sarstedt Microvette CB300 capillary tubes. Blood was collected at various time points starting at 2 min after NP injection, with up to six points per mouse. The tubes were centrifuged at 14,000×g for 15 min at 4° C. and the serum at the top of the tube used for analysis of Cy3 fluorescence, with excitation wavelength 530 nm and emission wavelength 570 nm, as compared to a standard curve of the NP formulation in mouse serum. The fraction of Cy3-siRNA remaining in serum was calculated using the serum volume based on mouse weight and the amount of formulation injected. Data points are from 3 mice per formulation.

Example 6. Results and Discussions

Example 6.1. cMAP Synthesis, NMR Characterization, and End-Group Determination

A cationic mucic acid polymer (cMAP) was synthesized by using the series of reactions schematically illustrated in FIG. 1. The mucic acid and the intermediate reaction products leading to the preparation of mucic acid ethylenediamine were fully characterized (Table 1).

TABLE 1

Figure 6:
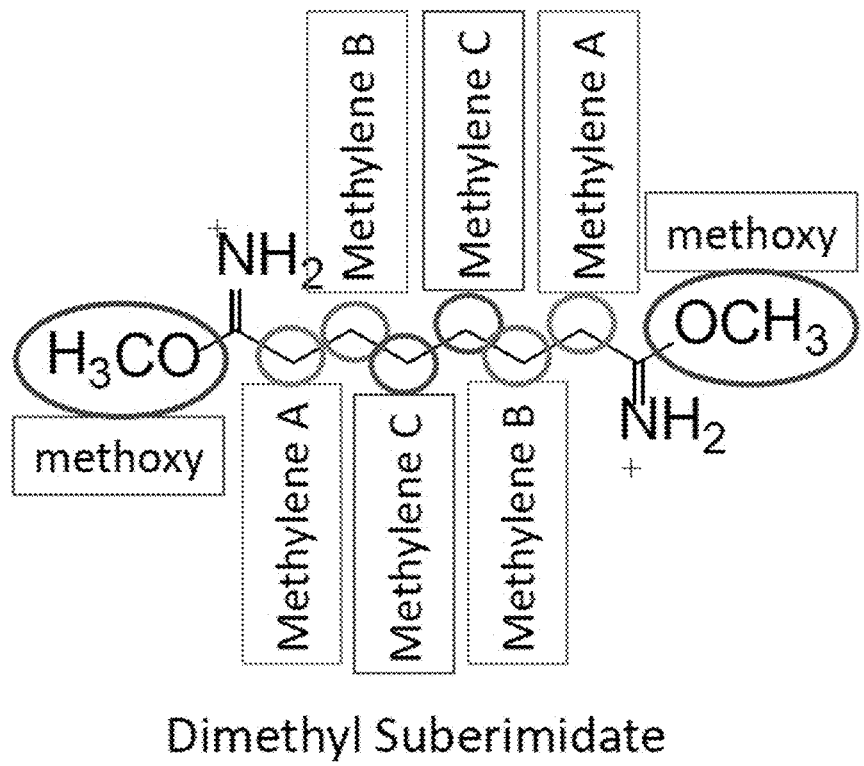
FIG. 6 shows the structure of Dimethyl Suberimidate (see Table 2).

NMR peak assignments for mucic acid ethylene diamine (see FIG. 6)

| | $^1$H in D$_2$O Chemical Shift (ppm) | $^1$H in DMSO-d$_6$ Chemical Shift (ppm) | $^{13}$C in DMSO-d$_6$ Chemical Shift (ppm) |
|---|---|---|---|
| Methylene A | 3.04 | 2.85 | 36.76 |
| Methylene B | 3.45 | Not observed | 39.25 |
| Methyne A | 3.9 | 3.82 | 70.98 |
| Methyne B | 4.32 | 4.15 | 71.39 |
| Hydroxyl A | Not observed | 4.55 | N/A |
| Hydroxyl B | Not observed | 5.30 | N/A |
| Amide and amines | Not observed | 7.83, 7.97 | N/A |
| Amide Carbonyl Carbon | N/A | N/A | 174.78 |

The condensation reaction between mucic acid ethylenediamine and Dimethyl Suberimidate (DMS) yielded the cMAP material. Because DMS can hydrolyze at conditions like those used for the polymerization, we investigated the reaction pathway for this reaction and the products formed (Table 2).

TABLE 2

Figure 7:
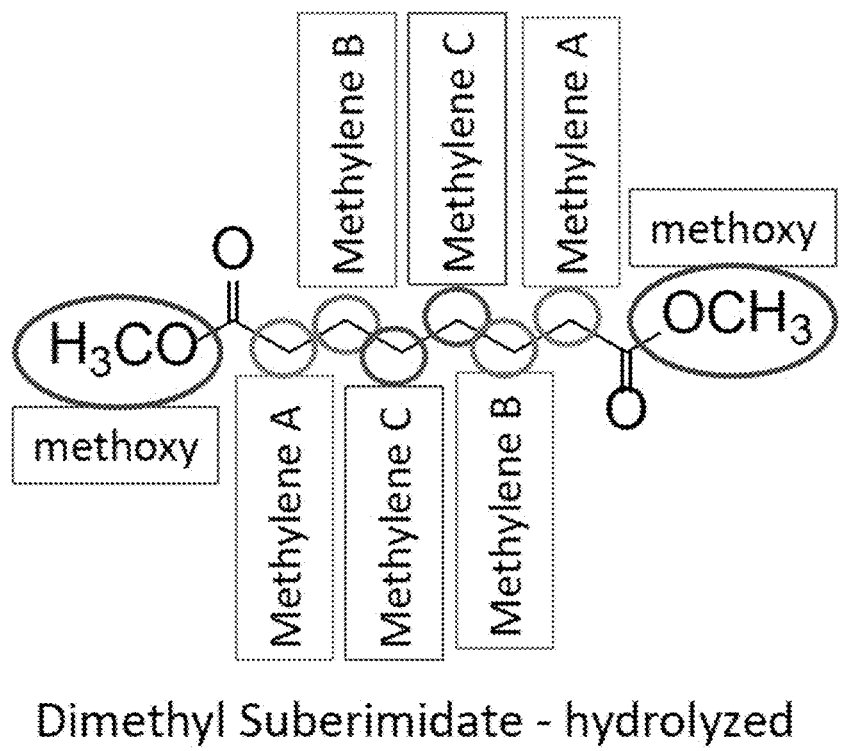
FIG. 7 shows the structure of Dimethyl Suberimidate hydrolyzed to the dimethyl ester (see Table 2).
Figure 8:
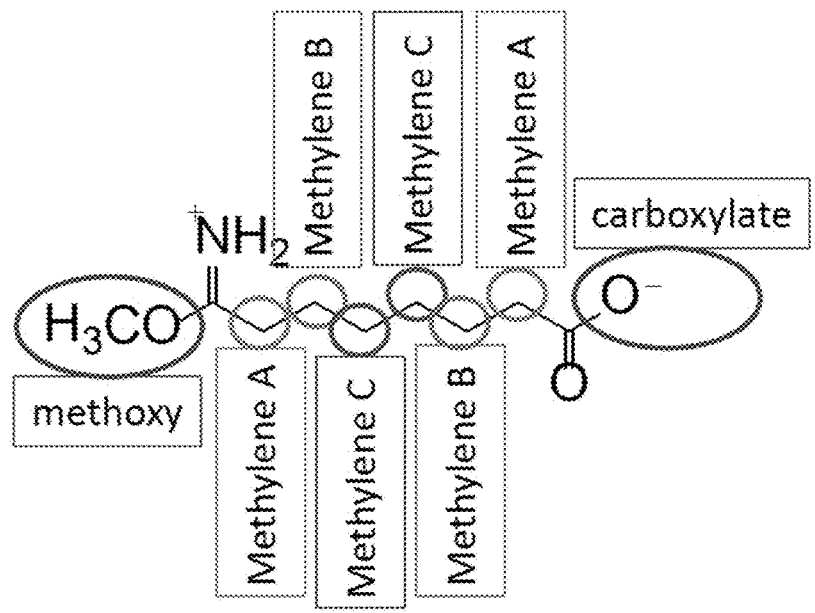
FIG. 8 shows the structure of Dimethyl Suberimidate with one side hydrolyzed to the carboxylate (see Table 2).

$^1$H NMR peak assignments for Dimethyl Suberimidate with varying degrees of hydrolysis (See FIGS. 6-8)

| | Methoxy | Methylene A | Methylene B | Methylene C |
|---|---|---|---|---|
| Dimethyl suberimidate (FIG. 6) | 4.08 | 2.64 | 1.60 | 1.30 |
| Dimethyl suberimidate hydrolyzed to the dimethyl ester (FIG. 7) | 3.55 | 2.25 | 1.45 | 1.20 |
| Dimethyl suberimidate hydrolyzed to carboxylate (FIG. 8) | None | 2.01 | 1.46 | 1.20 |

The presence of dimethyl suberimidate containing one methoxy group which was completely hydrolyzed to a carboxylate group was further confirmed by both the ESI mass spectrum peak at m/z of 187.9 and the $^1$H—$^{13}$C HMBC NMR spectrum. The methylene A peak in this case was present on $^1$H NMR with a chemical shift of 2.01 ppm.

This information assisted in the characterization of the cMAP product.

NMR analysis of cMAP (including $^1$H-$^{13}$C HSQC NMR, $^1$H-$^1$H COSY NMR, and $^1$H-$^{13}$C HMBC NMR data (Tables 3-4) enabled the assignment of all resonances to the various carbon and hydrogen environments in the polymer. Of importance was the identification of the end group composition of cMAP, as these functionalities are utilized in subsequent reactions with functionalized PEG to form cMAP-PEG copolymers or mPEG-cMAP-PEGm triblock polymers.

TABLE 3

Figure 9:
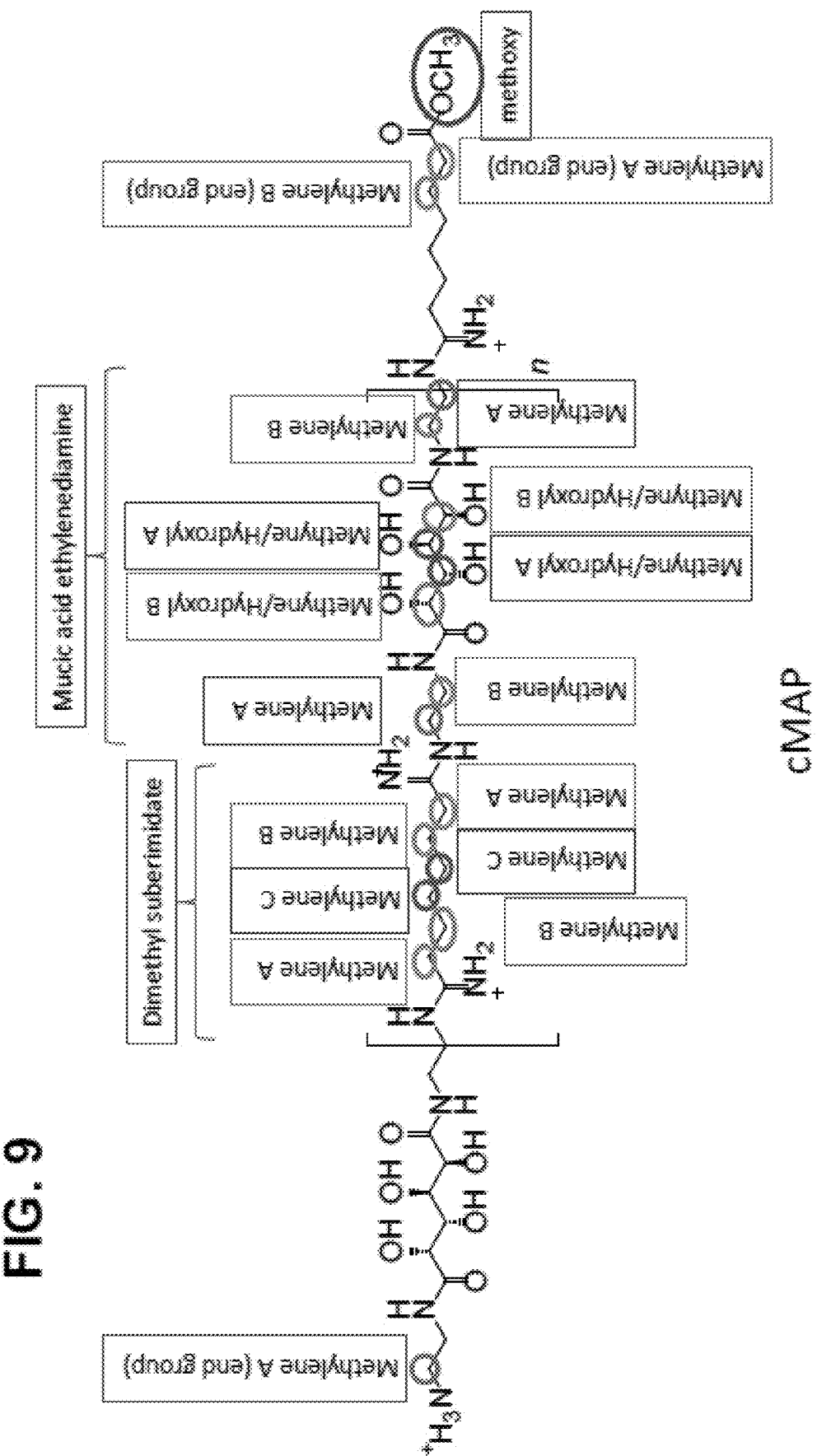
FIG. 9 shows the structure of cationic Mucic Acid Polymer (cMAP).

$^1$H NMR peak assignments for cMAP; see FIG. 9

| | Originating Monomer | $^1$H in DMSO Chemical Shift (ppm) |
|---|---|---|
| Amidine | Mucic acid and dimethyl suberimidate | 9.65 |
| Amidine | Mucic acid and dimethyl suberimidate | 9.28 |
| Amidine | Mucic acid and dimethyl suberimidate | 8.78 |
| Amide | Mucic acid and dimethyl suberimidate | 7.92 |
| Hydroxyl B | Mucic acid | 5.42 |

TABLE 3-continued $^1$H NMR peak assignments for cMAP; see FIG. 9

| | Originating Monomer | $^1$H in DMSO Chemical Shift (ppm) |
|---|---|---|
| Hydroxyl A | Mucic acid | 4.56 |
| Methyne B | Mucic acid | 4.18 |
| Methyne A | Mucic acid | 3.84 |
| Methoxy (end group) | Dimethyl suberimidate | 3.58 |
| Methylene B | Mucic acid | 3.40 |
| Methylene A | Mucic acid | 3.29 |
| Methylene A (end group) | Mucic acid | 2.87 |
| Methylene A | Dimethyl suberimidate | 2.42 |
| Methylene A (end group) | Dimethyl suberimidate | 2.30 |
| Methylene A (end group) | Dimethyl suberimidate - hydrolyzed to carboxylate | 2.03 |
| Methylene B | Dimethyl suberimidate | 1.63 |
| Methylene B (end group) | Dimethyl suberimidate | 1.52 |
| Methylene C | Dimethyl suberimidate | 1.30 |

TABLE 4

$^{13}$C NMR peak assignments for cMAP; see FIG. 9.

| | Originating Monomer | $^{13}$C in DMSO Chemical Shift (ppm) |
|---|---|---|
| Amide Carbonyl | Mucic acid | 174.29 |
| Methoxy Carbonyl (end group) | Dimethyl suberimidate | 173.47 |
| Amide Carbonyl (end group) | Mucic acid | 171.03 |
| Amidine Carbonyl | Dimethyl suberimidate | 167.79, 166.82 |
| Methyne B | Mucic acid | 70.83 |
| Methyne A | Mucic acid | 70.61 |
| Methoxy (end group) | Dimethyl suberimidate | 51.31 |
| Methylene A | Mucic acid | 41.73 |
| Methylene B | Mucic acid | 36.37 |
| Methylene A | Dimethyl suberimidate | 32.15 |
| Methylene C | Dimethyl suberimidate | 27.48 |
| Methylene B | Dimethyl suberimidate | 26.31 |
| Methylene A (end group) | Dimethyl suberimidate - hydrolyzed to carboxylate | 35.06 |
| Methylene A (end group) | Dimethyl suberimidate | 33.22 |
| Methylene B (end group) | Dimethyl suberimidate | 24.23 |

Figure 10:
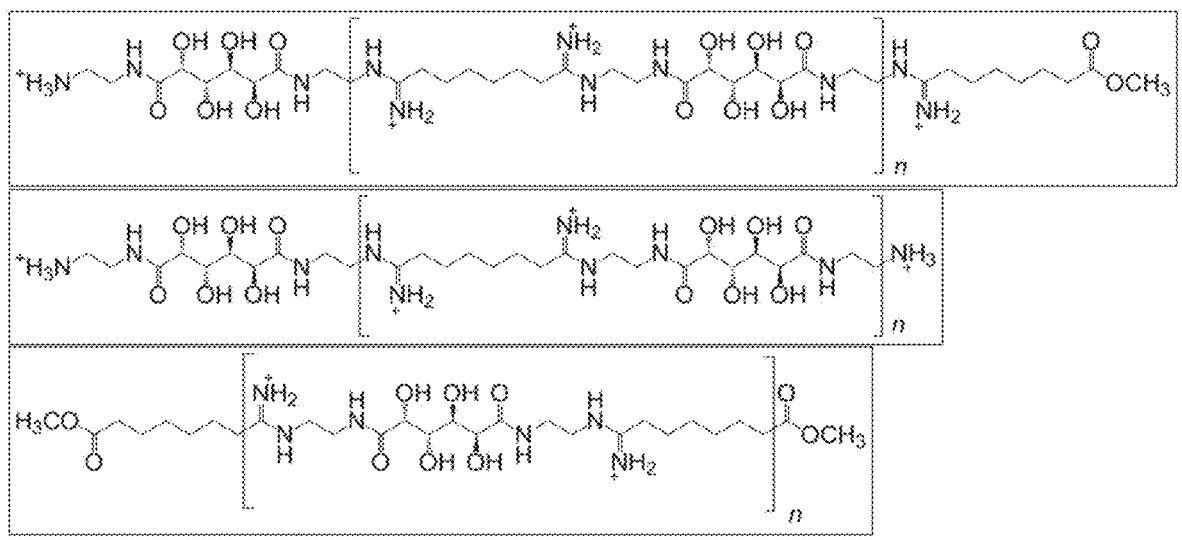
FIG. 10 shows exemplary end groups of cMAP. Polymers can have one amine and one methoxy (top), both amine (middle), or both methoxy (bottom) end groups. A small amount of carboxylic acid is also observed and would be generated from hydrolysis of one end of DMS.
Figure 11:
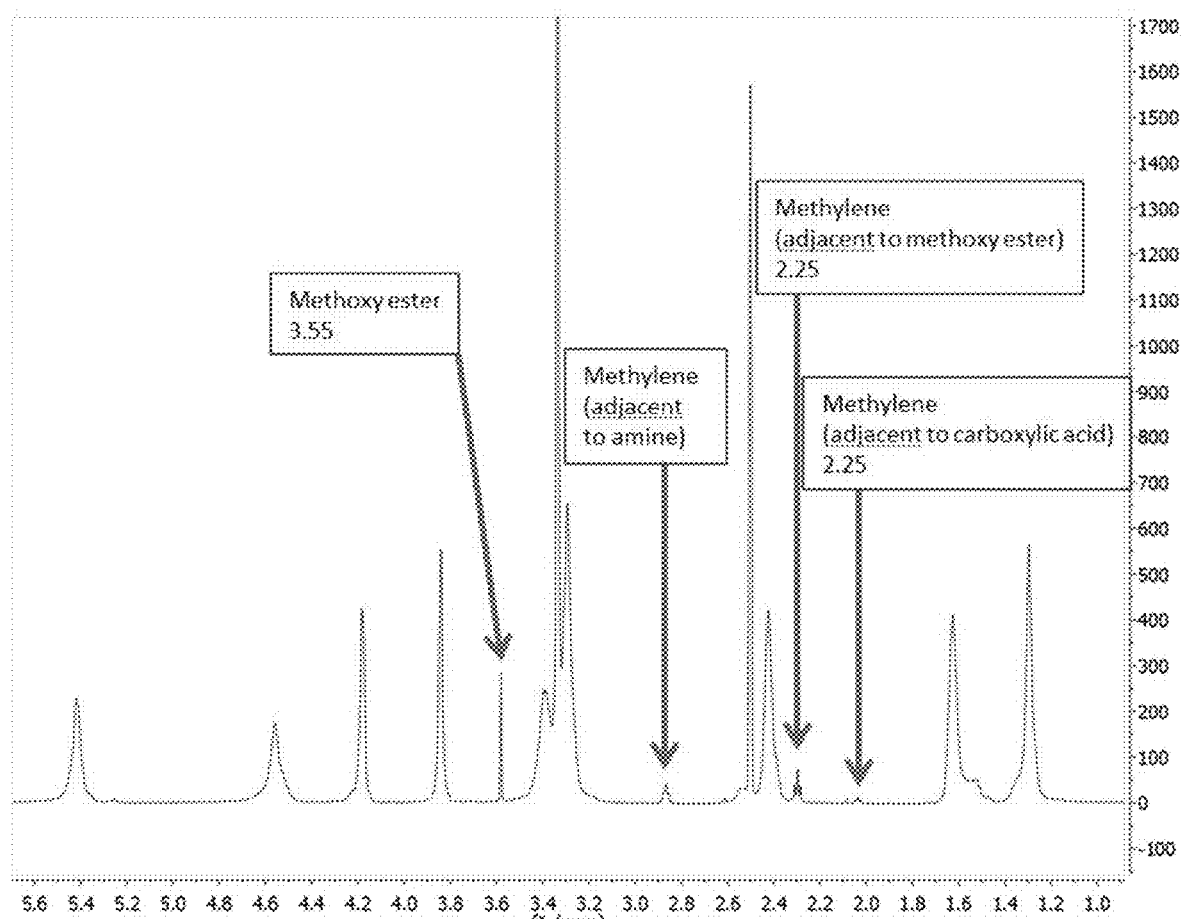
FIG. 11 is a $^1$H NMR (600 MHz) spectrum of cMAP showing resonances from the methoxy group and methylene groups adjacent to the end group functionalities.

The cMAP end groups include methoxy of a methoxy ester, amine, and small amounts of carboxylic acid (FIG. 10). $^1$H NMR analysis of cMAP shows the presence of a characteristic sharp methoxy peak at 3.55 ppm (FIG. 11), and this assignment is supported by $^1$H-$^{13}$C HSQC NMR measurements (not shown). The methoxy group originates from the loss of ammonia from the imidate group of the DMS through hydrolysis (Table 2, FIGS. 6-8), and had been previously reported. The methylene group adjacent to the methoxy can be observed as a triplet at 2.25 ppm in the $^1$H NMR spectrum (FIG. 11). The amine end group that originates from the mucic acid ethylenediamine cannot be directly observed with $^1$H NMR. However, analysis of the NMR spectrum of the monomer and the HMBC NMR spectrum of cMAP enabled assignment of the triplet at 2.85 ppm to be from a methylene group adjacent to the amine functional group. Additionally, a TNBSA assay for primary amines was positive, thus confirming that the cMAP has a terminal primary amine as an end group. Lastly, there was a small amount of carboxylic acid as an end group that arises from complete hydrolysis of the methyl ester or as an impurity in the starting DMS. The methylene group adjacent to the carboxylic acid is observed as a small triplet at 2.00 ppm in the $^1$H NMR spectrum (FIG. 11). The ratios of these end groups in a batch of cMAP can be determined by comparing the integrations of the triplets at 2.85 (amine), 2.25 (methoxy), and 2.00 (carboxylate) ppm, and are shown for 8 batches in Table 5. The average values for the % amine, % methoxy, and % carboxylate are 49%, 42%, and 9%, respectively.

TABLE 5

Ratios of amine:methoxy:carboxylate end groups in 8 batches of cMAP by comparing NMR integrations.

| Batch | % amine | % methoxy | % carboxylate |
|---|---|---|---|
| 11 | 52.52 | 33.96 | 13.52 |
| 12 | 38.45 | 54.15 | 7.40 |
| 13 | 48.58 | 45.89 | 5.53 |
| 14 | 47.07 | 45.71 | 7.22 |
| 15 | 47.75 | 51.17 | 1.08 |
| 16 | 55.58 | 37.14 | 7.28 |
| 17 | 63.22 | 29.92 | 6.86 |
| 18 | 38.76 | 39.50 | 21.75 |
| Average | 48.99 ± 2.93 | 42.18 ± 2.99 | 6.22 ± 2.20 |

Example 6.1. cMAP-PEG Copolymer and mPEG-cMAP-PEGm Triblock cMAP was reacted with activated carboxylic acid end groups on PEG, such as succinimidyl propionic acid ester (SPA) or succinimidyl valeric acid ester (SVA). cMAP reacted with di-SPA-PEG or mPEG-SVA generated copolymers or triblock polymers, respectively, with PEG lengths of 2, 3.4, or 5 kD.

Because a significant amount of diamine terminated polymer chains exist in the cMAP mixture, reaction with di-SPA-PEG (FIG. 2) resulted in cMAP-PEG copolymers with large size distributions (copolymers ranged from a diblock cMAP-PEG copolymer just slightly larger than 10 kD, to a cMAP-PEG-cMAP triblock polymer terminated by a methyl ester or carboxylic acid on the cMAPs, to a long polymer of over 100 kD; size distributions reported in Tables 6-7 are from the polymer yields obtained by fractionating the crude polymer through sequentially smaller molecular weight cutoff centrifugal spin filters).

TABLE 6

Retained mass on each MWCO filter after fractionating crude cMAP-PEG3.4k copolymer.

| MWCO (kD) | Mass (mg) | Comment |
|---|---|---|
| 100 | 9.5 | High molecular weight cMAP-PEG copolymer |
| 50 | 3.4 | High molecular weight cMAP-PEG copolymer |
| 30 | 5 | High molecular weight cMAP-PEG copolymer |
| 20 | 12.3 | |

TABLE 6-continued

Retained mass on each MWCO filter after fractionating crude cMAP-PEG3.4k copolymer.

| MWCO (kD) | Mass (mg) | Comment |
|---|---|---|
| 10 | 10.6 | Pure cMAP-PEG-cMAP triblock |
| 3 | 13.2 | Unreacted cMAP, excess PEG |
| Total | 54 | |

A reaction was started with 50 mg of cMAP and 16.5 mg di-SPA-PEG3.4k. After stirring for 24 hours, the reaction was diluted in water and filtered through sequentially smaller molecular weight cutoff (MWCO) Amicon centrifugal spin filters. Some material loss does occur onto the filter membrane and during transfer steps, but the retained material on each of these filters after lyophilization to dryness is shown. A significant amount of high molecular weight cMAP-PEG3.4k copolymer is formed in the synthesis due to the presence of diamine end groups on cMAP.

TABLE 7

Retained mass on each MWCO filter after fractionating crude cMAP-PEG5k copolymer.

| MWCO (kD) | Mass (mg) | Comment |
|---|---|---|
| 30 | 18.3 | High molecular weight cMAP-PEG copolymer |
| 20 | 20.8 | |
| 10 | 12 | Pure cMAP-PEG-cMAP triblock + cMAP-PEG diblock |
| Total | 51.1 | |

Similarly, a reaction was started with 50 mg of cMAP and 22.3 mg di-SVA-PEG5k. After stirring for 24 hours, the reaction was diluted in water and filtered through sequentially smaller molecular weight cutoff (MWCO) Amicon centrifugal spin filters. Some material loss does occur onto the filter membrane and during transfer steps, but the retained material on each of these filters after lyophilization to dryness is shown. A significant amount of higher molecular weight cMAP-PEG5k copolymer is formed in this synthesis similar to the analogous reaction above.

Because a polymer with such a large molecular weight could pose substantial toxicity in vivo, in an effort to synthesize a well-defined polymer with a reasonable length, the cMAP-PEG-cMAP triblock polymer species was isolated from the copolymer using this fractionation method. Other triblock polymers of this repeat structure of a cationic polymer flanking a PEG or PLA polymer has been explored previously for gene and iron oxide-carbon nanotube delivery.

Reacting cMAP with mPEG-SVA limited the structure of the resulting product to the mPEG-cMAP-PEGm triblock polymer (FIG. 3). Some cMAP-PEGm diblock polymer was also present and separated from the desired triblock by fractionation.

Example 6.2. Molecular Weights of Polymers by GPC

Gel permeation chromatography was used to characterize the molecular weight of cMAP. Though the elution time of the polymer can be correlated to its size, with new cationic polymers there are no ideal size standards for calibration. Therefore, we determined the absolute molecular weight of the polymers using a multi-angle light scattering detector. The advantage of this method is its dependence only on the polymer's scattering ability and its concentration; it does not require a standard for comparison. The differential refractive index with respect to concentration, dn/dc, of cMAP was determined (Table 8) and used to measure molecular weight. The average molecular weight of 9 batches of cMAP was around 6 kD with a polydispersity index (PDI) of less than 1.1 (Table 8). The results from the individual batches can be found in Table 9.

TABLE 8

Molecular weights of cMAP-based polymers.

| Polymer | dn/dc (mL/g) | Mn (kD) | Mw (kD) | PDI (Mw/Mn) |
|---|---|---|---|---|
| cMAP (9 batches ± std. error) | 0.1806 ± 0.0002 | 6.30 ± 0.40 | 6.76 ± 0.40 | 1.08 ± 0.01 |
| cMAP-PEG5k copolymer (2 batches ± std. error) | 0.1660 ± 0.0003 | 28.72 ± 4.55 | 41.49 ± 14.65 | 1.40 ± 0.29 |
| mPEG5k-cMAP-PEG5km (3 batches ± std. error) | 0.1420 ± 0.0004 | 20.98 ± 0.67 | 21.95 ± 0.67 | 1.05 ± 0.02 |

TABLE 9

Gel Permeation Chromatography Analysis of cMAP Batches.

| Sample | Mn | Mw | Mw/Mn (PDI) |
|---|---|---|---|
| cMAP-DP11 | 5323 | 6068 | 1.14 |
| cMAP-DP12 | 5213 | 5839 | 1.12 |
| cMAP-DP13 | 5936 | 6365 | 1.07 |
| cMAP-DP14 | 5747 | 5940 | 1.03 |
| cMAP-DP15 | 5050 | 5568 | 1.10 |
| cMAP-DP16 | 6102 | 6357 | 1.04 |
| cMAP-DP17 | 7712 | 8235 | 1.07 |
| cMAP-DP18 | 7313 | 7524 | 1.03 |
| cMAP-DP19 | 8353 | 8984 | 1.08 |

Values are reported as the average of 3 runs.

Using a similar method, the 5k cMAP-PEG copolymer had a larger size distribution with a PDI of 1.4, and an Mw of 42 kD and Mn of 29 kD (Table 8). The 5k mPEG-cMAP-PEGm triblock was about 21 kD with a PDI of less than 1.1 (Table 8). Additionally, results for the 3.4 kD PEG cMAP-PEG copolymer and the 2 kD PEG mPEG-cMAP-PEGm triblock, as well as the cMAP-PEG-cMAP triblocks derived from fractionating the cMAP-PEG copolymer are all reported in Table 10.

TABLE 10

GPC Analysis of cMAP copolymers and triblocks (other than 5 kD PEG reported in main article text).

| Polymer | dn/dc (mL/g) | Mn (kD) | Mw (kD) | PDI (Mw/Mn) |
|---|---|---|---|---|
| cMAP-PEG3.4k Copolymer | 0.1660 | 128.30 | 289.25 | 2.27 |
| cMAP-PEG3.4k-cMAP | 0.1660 used (not for pure triblock) | 12.89 | 14.20 | 1.10 |
| cMAP-PEG5k-cMAP | 0.1660 used (not for pure triblock) | 24.17 | 26.84 | 1.11 |
| mPEG2k-cMAP-PEG2km | 0.1654 | 9.75 | 9.81 | 1.01 |

Example 6.3. siRNA Encapsulation by cMAP-Based Polymers

Figure 12:
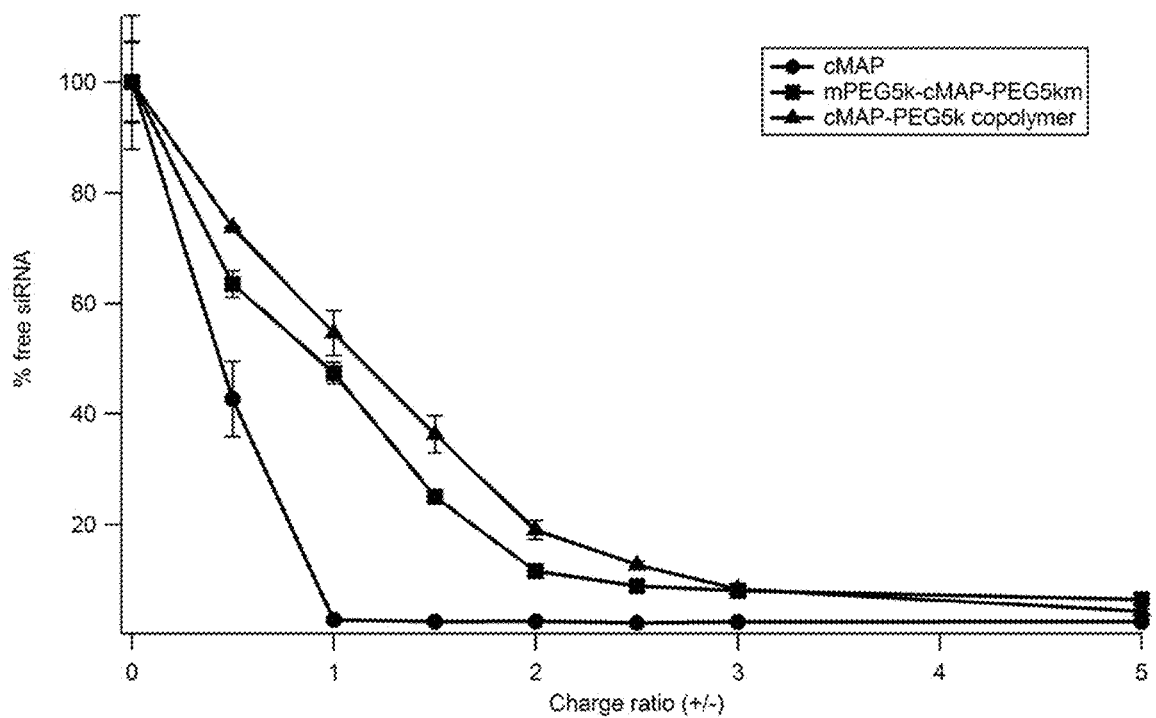
FIG. 12 shows the relationship between the percentage of siRNA with charge ratio (encapsulated by cMAP, cMAP-PEG5k copolymer, and mPEG5k-cMAP-PEG5 km triblock polymer) using the RiboGreen assay.
Figure 13:
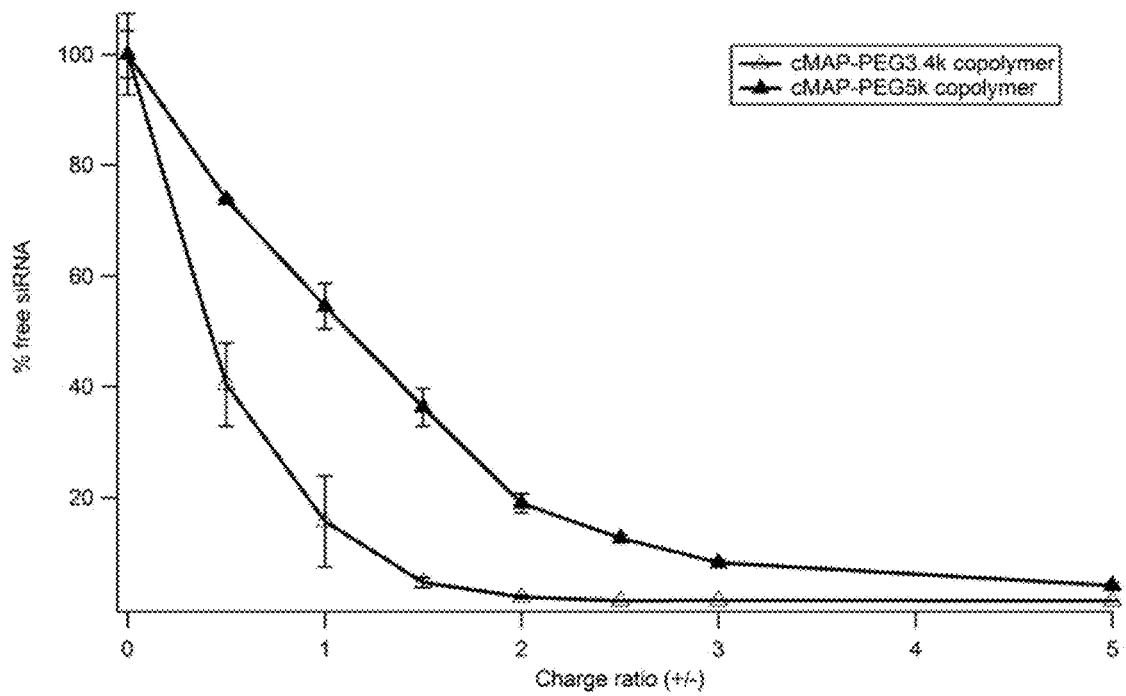
FIG. 13 shows cMAP-PEG copolymer RiboGreen assay showing siRNA encapsulation by a charge ratio of 3+/− for 3.4 k and 5 k PEG blocks.
Figure 14:
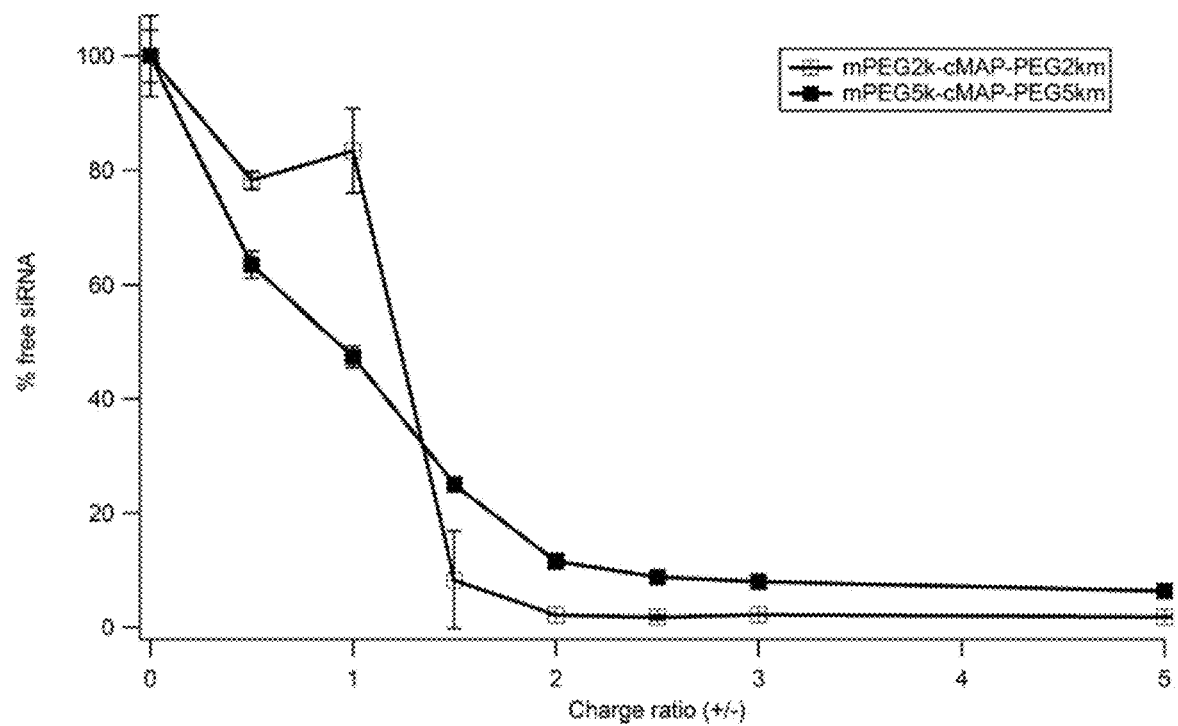
FIG. 14 shows mPEG-cMAP-PEGm triblock RiboGreen assay showing siRNA encapsulation by a charge ratio of 3+/− for 2 k and 5 k PEG blocks.
Figure 15:
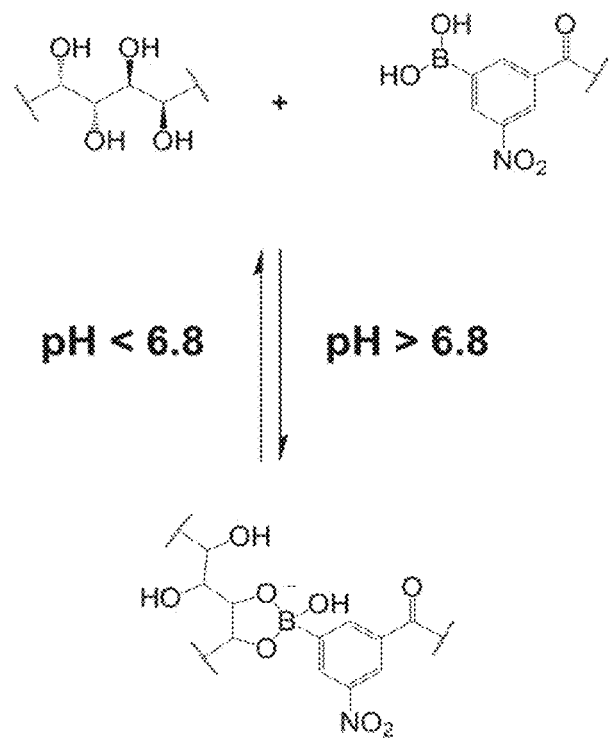
FIG. 15 shows the pH dependence of 5-nitrophenylboronic acid-PEGm which forms the boronic acid ester with vicinal diols on cMAP at a physiological pH of around 7.4, but which will dissociate at acidic pH.

The ability of cMAP, cMAP-PEG copolymer, and mPEG-cMAP-PEGm triblock polymer to encapsulate siRNA was confirmed using both a RiboGreen assay and a gel retardation assay. cMAP is able to encapsulate siRNA at a charge ratio (+/−) of 1+/−, and the cMAP-PEG5k copolymer and the mPEG5k-cMAP-PEG5 km triblock both are able to fully encapsulate siRNA by a charge ratio of 3 or 2, respectively, using the fluorescent RiboGreen assay (FIG. 12). Similar siRNA encapsulation data is reported for copolymers and triblock polymers of the other PEG lengths in FIGS. 13-14.

The results of the RiboGreen assay are perhaps more sensitive, but comparable to those from a gel retardation assay.

Example 7. Nanoparticle Formulations and Properties

Figure 17:
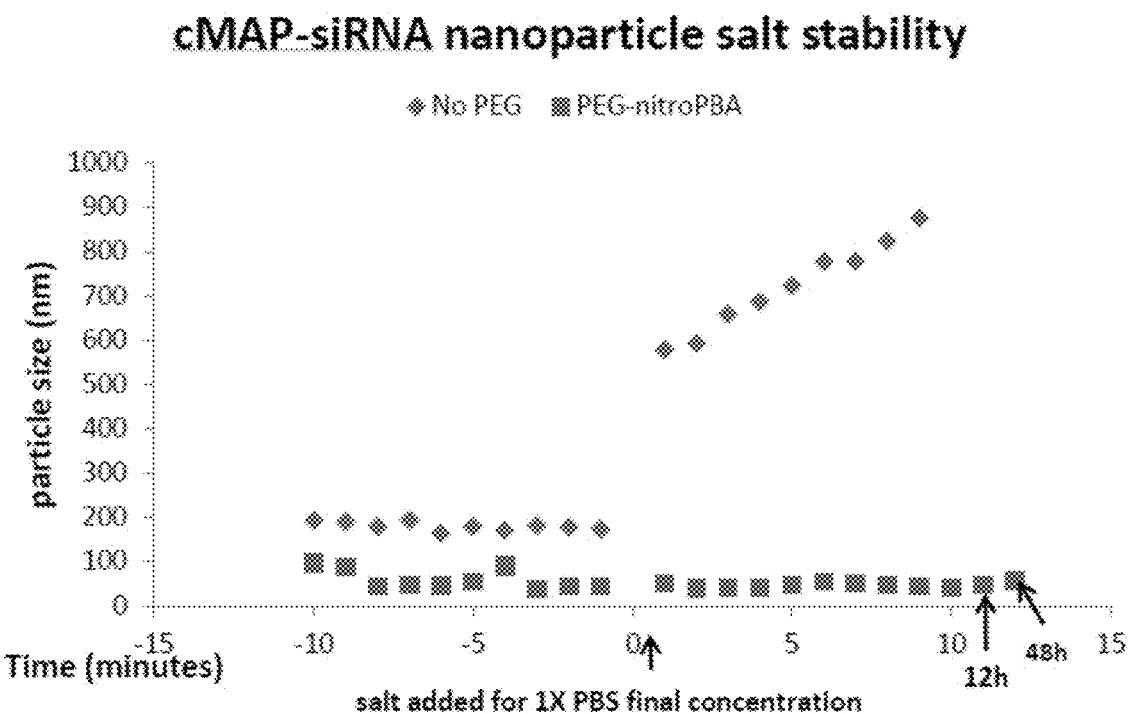
FIG. 17 shows cMAP siRNA NP salt stability data. Without PEG, the cMAP-siRNA NP was unstable once in 1×PBS, but was stable for 2 days when 5-nPBA-PEGm is used to stabilize the NP.

Example 7.1. Formulations 5-nitrophenyl boronic acid-PEGm (5-nPBA-PEGm) contains a boronic acid group that allows one end of this 50) PEG to bind to vicinal diol groups on mucic acid in cMAP at a pH above 6.8 to provide steric stabilization of the siRNA-containing NPs as illustrated in 15. The various NP formulations using cMAP, cMAP-PEG copolymer, and mPEG-cMAP-PEGm, triblock polymer with or without extra 5-nPBA-PEGm are shown in FIGS. 16(A-B). A NP prepared by mixing cMAP and siRNA at a 3+/− charge ratio without the addition of 5-nPBA-PEGm, while stable in water, is unstable in PBS (one 5-nPBA-PEGm per diol added to the formulation, FIG. 17).

Figure 18:
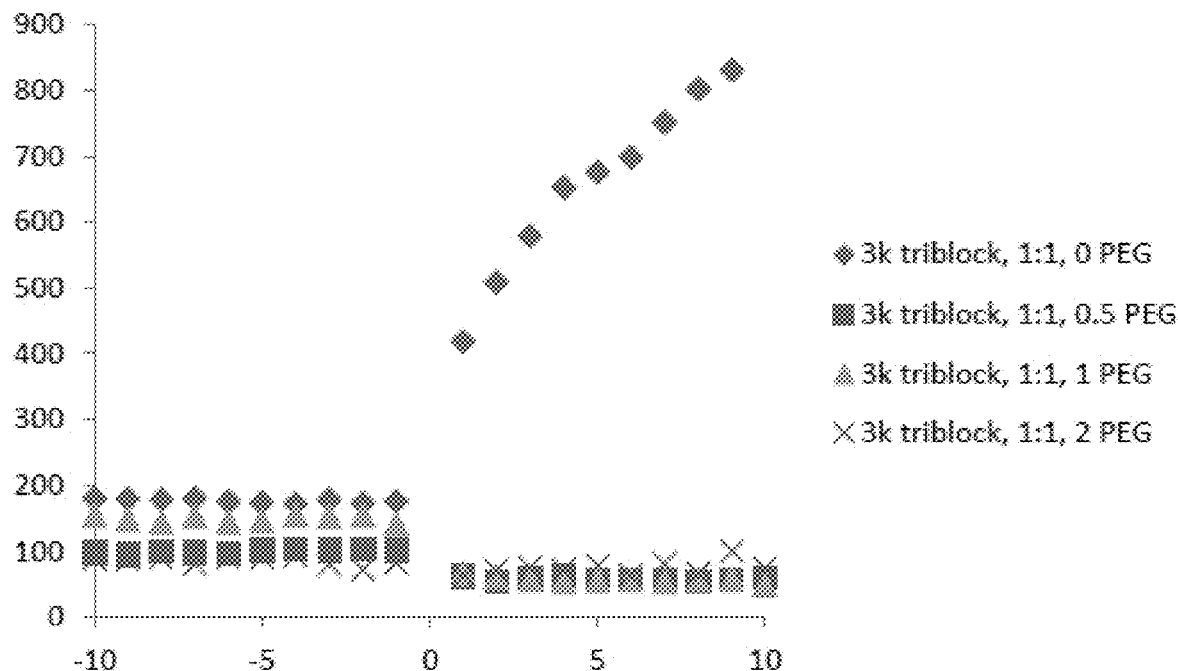
FIG. 18 shows cMAP-PEG-cMAP pure triblock siRNA NP salt stability Without added 5-nPBA-PEGm, the cMAP-PEG3.4k-cMAP siRNA NP formulated at a 1+/− charge ratio aggregates once in IX PBS, but is stable when at least one 5-nPBA-PEGm per two diol groups (0.5 PEG) on cMAP is added to the formulation.
Figure 19:
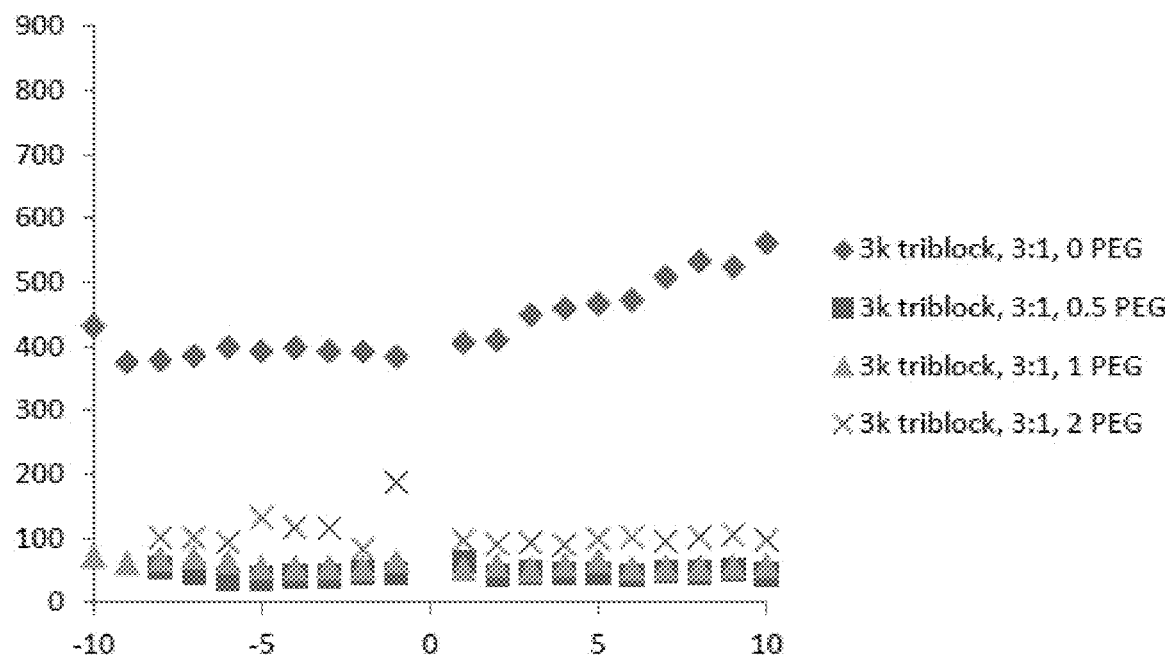
FIG. 19 shows cMAP-PEG-cMAP pure triblock siRNA NP salt stability. Without added 5-nPBA-PEGm, the cMAP-PEG3.4k-cMAP siRNA NP formulated at a 3+/− Charge ratio aggregates once in 1×PBS, but is stable when at least one 5-nPBA-PEGm per two diol groups (0.5 PEG) on cMAP is added to the formulation.
Figure 20:
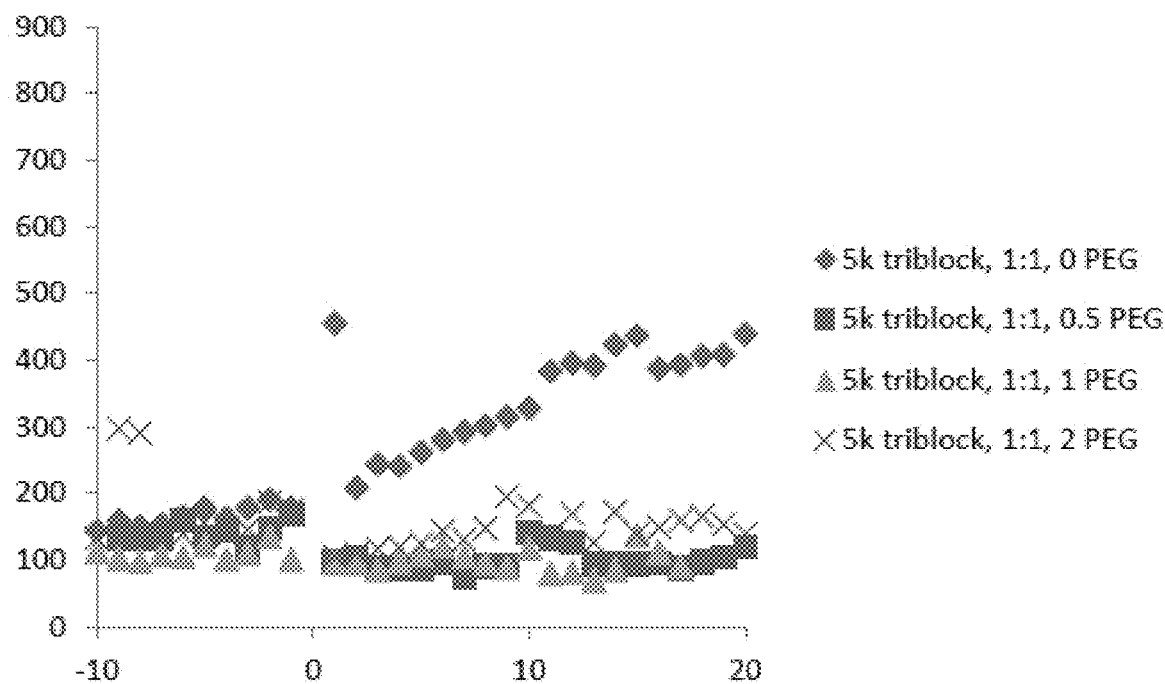
FIG. 20 shows cMAP-PEG-cMAP pure triblock siRNA NP salt stability. Without added 5-nPBA-PEGm, the cMAP-PEG5k-cMAP siRNA NP formulated at a 1+/− charge ratio aggregates once in IX PBS, but is stable when at least one 5-nPBA-PEGm per two diol groups (0.5 PEG) on cMAP is added to the formulation.
Figure 21A:
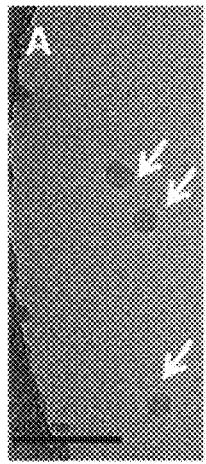
FIGS. 21A-E show cryoTEM images of NP formulations: cMAP+5-nPBA-PEG5 km (FIG. 21A), cMAP-PEG5k copolymer (FIG. 21B), cMAP-PEG5k copolymer+5-nPBA-PEG5 km (FIG. 21C), mPEG5k-cMAP-PEG5 km (FIG. 21D), and mPEG5k-cMAP-PEG5 km+5-nPBA-PEG5 km (FIG. 21E).
Figure 21B:
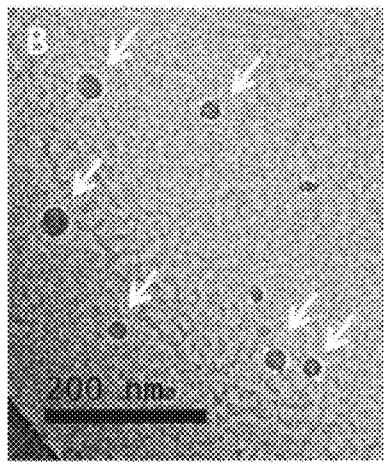
Figure 21C:
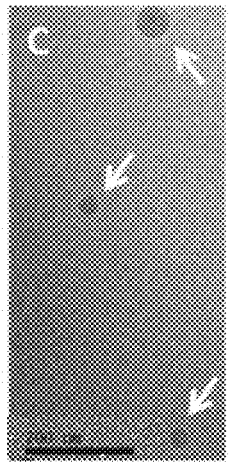
Figure 21D:
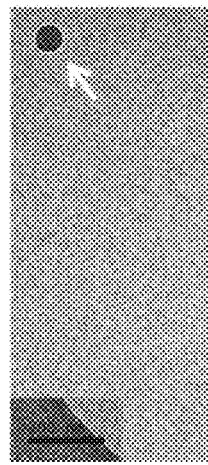
Figure 21E:
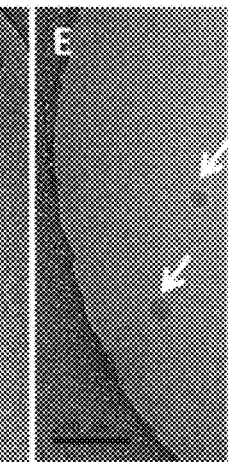
Figure 22A:
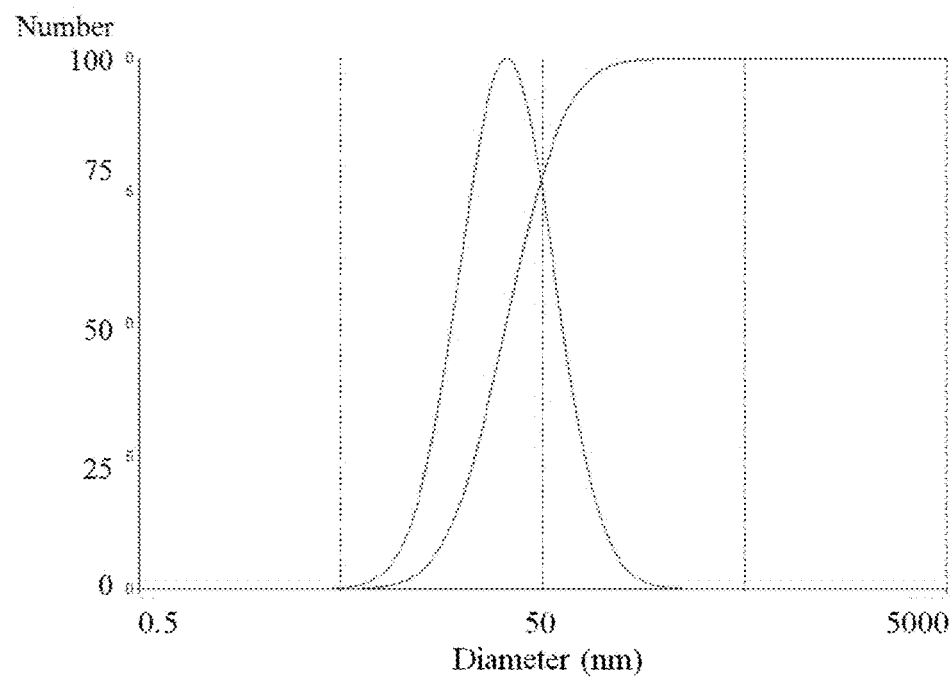
FIG. 22(A-E) shows DLS Nanoparticle Size Distributions: Log normal size distribution by DLS for the cMAP+5-nPBA-PEGm NP (FIG. 22(A)); for the CMAP-PEG copolymer NP (FIG. 22(B)); for the cMAP-PEG copolymer+5-nPBA-PEGm NP (FIG. 22(C)); for the mPEG-cMAP-PEGm NP (FIG. 22(D)); and for the mPEG-cMAP-PEGm+5-nPBA-PEGm NP (FIG. 22(E)).
Figure 22B:
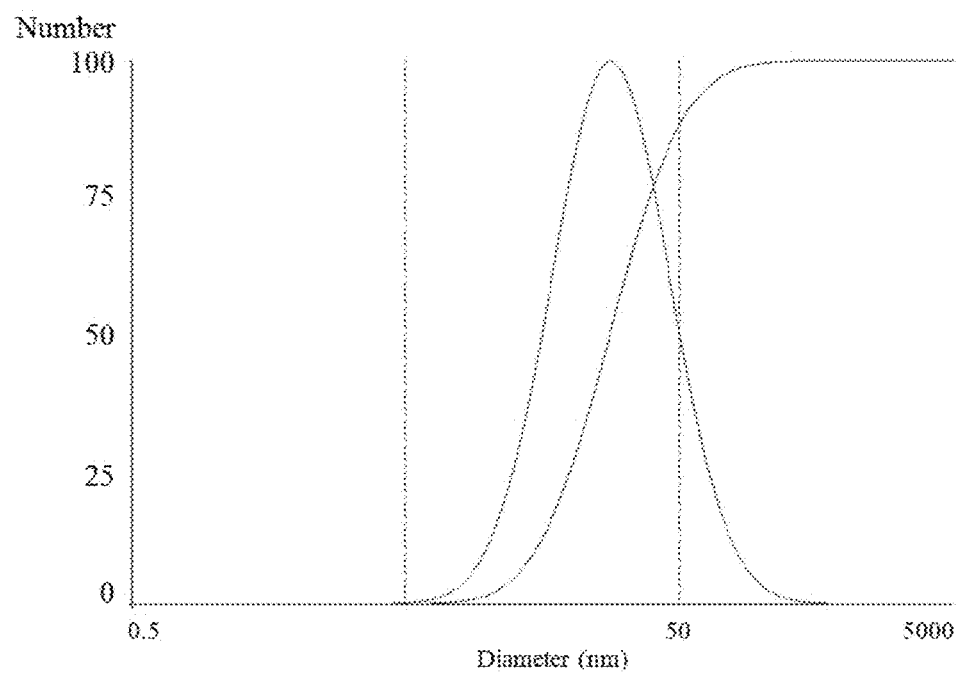
Figure 22C:
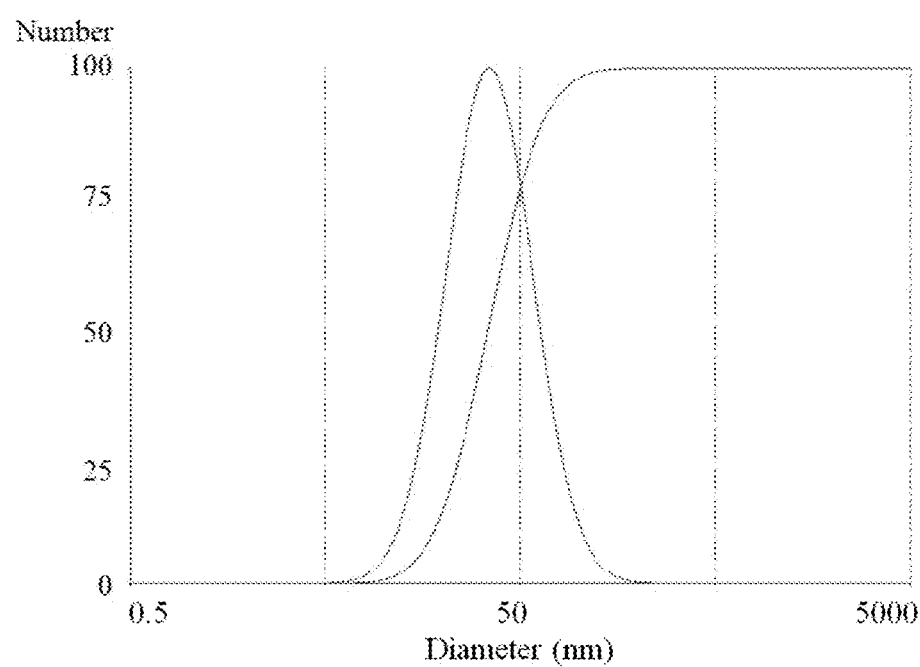
Figure 22D:
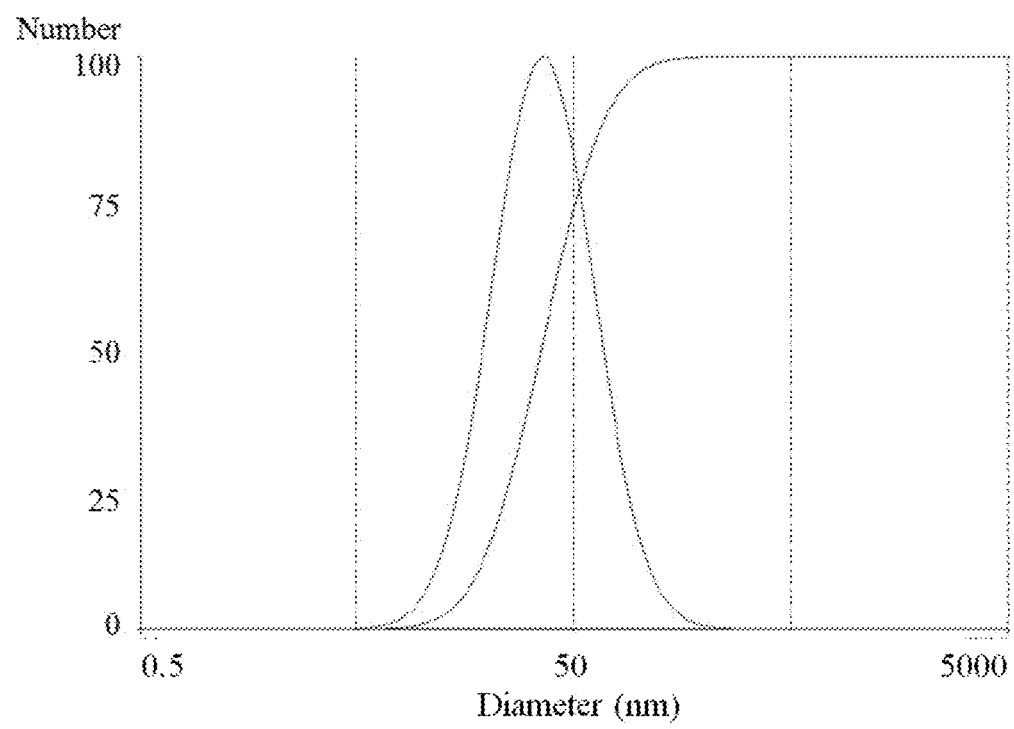
Figure 22E:
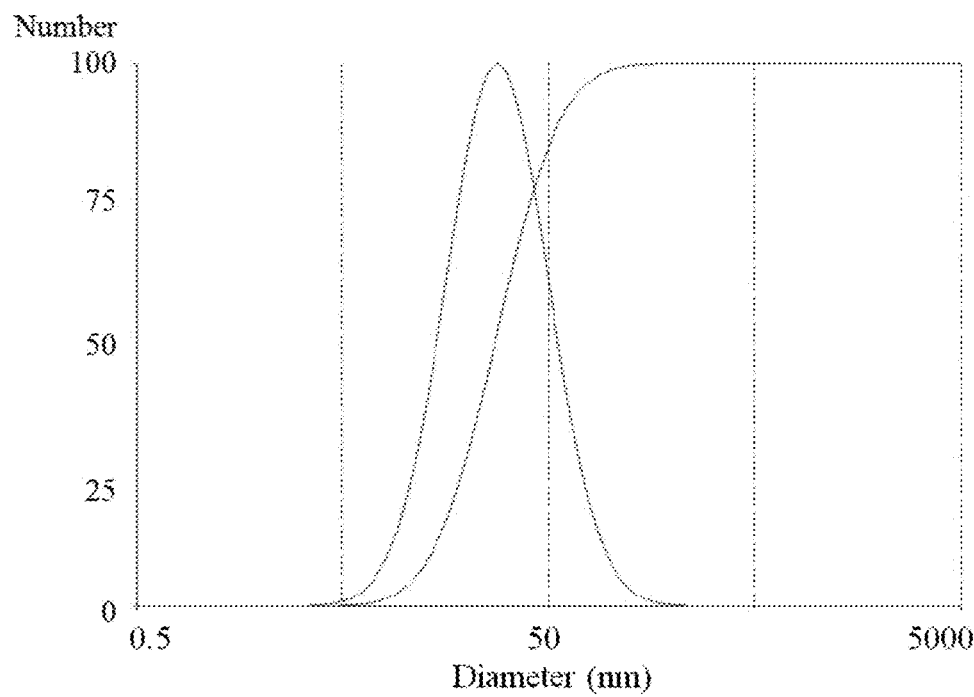
Figure 23A:
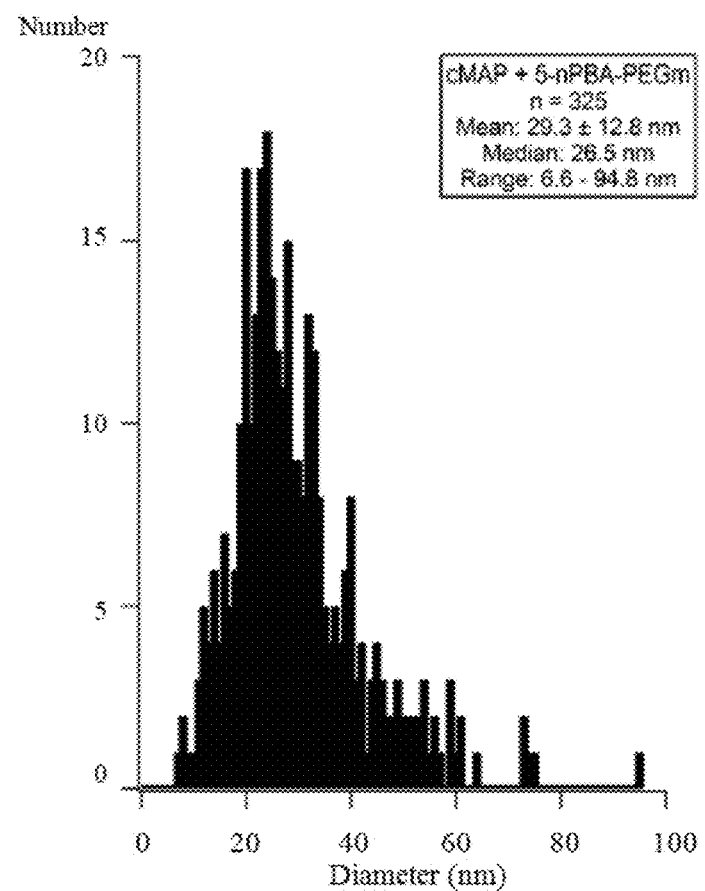
FIG. 23(A-E) shows the size distribution by CryoTEM for the cMAP+5-nPBA-PEGm NP (FIG. 23(A)); for the for the cMAP-PEG copolymer NP (FIG. 23(B)); for the cMAP-PEG copolymer+5-nPBA-PEGm NP (FIG. 23(C)); for the mPEG-cMAP-PEGm NP (FIG. 23(D)); and for the mPEG-cMAP-PEGm+5-nPBA-PEGm NP (FIG. 23(E)).
Figure 23B:
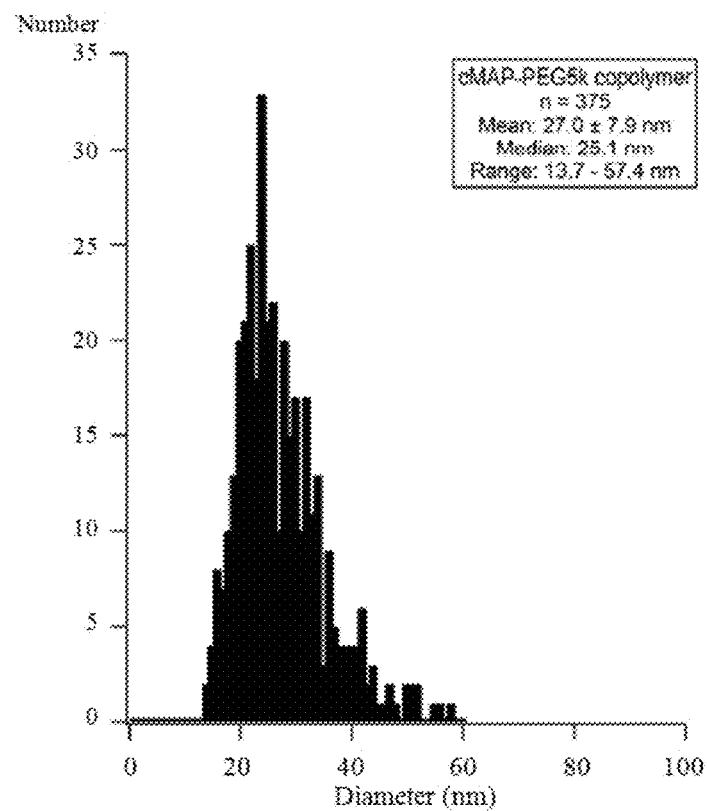
Figure 23C:
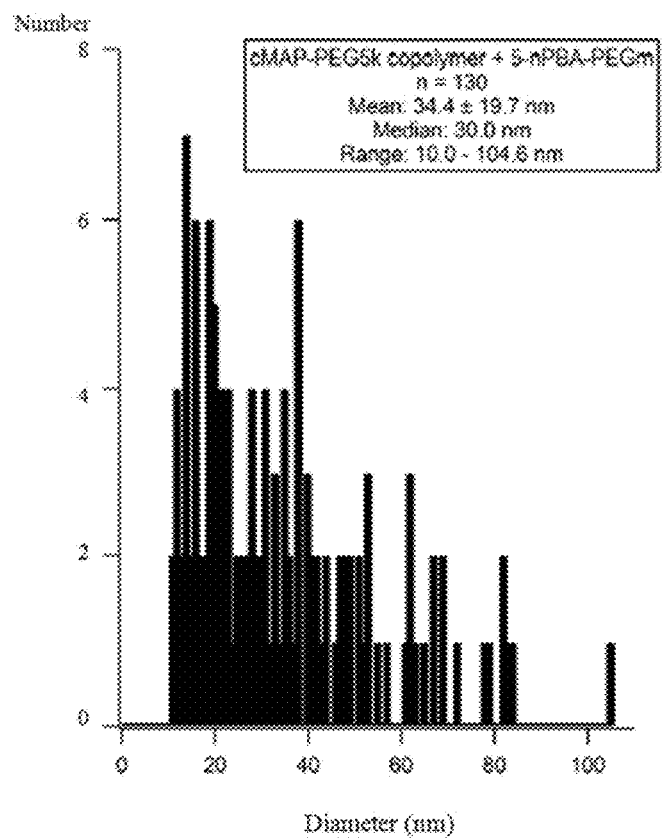
Figure 23D:
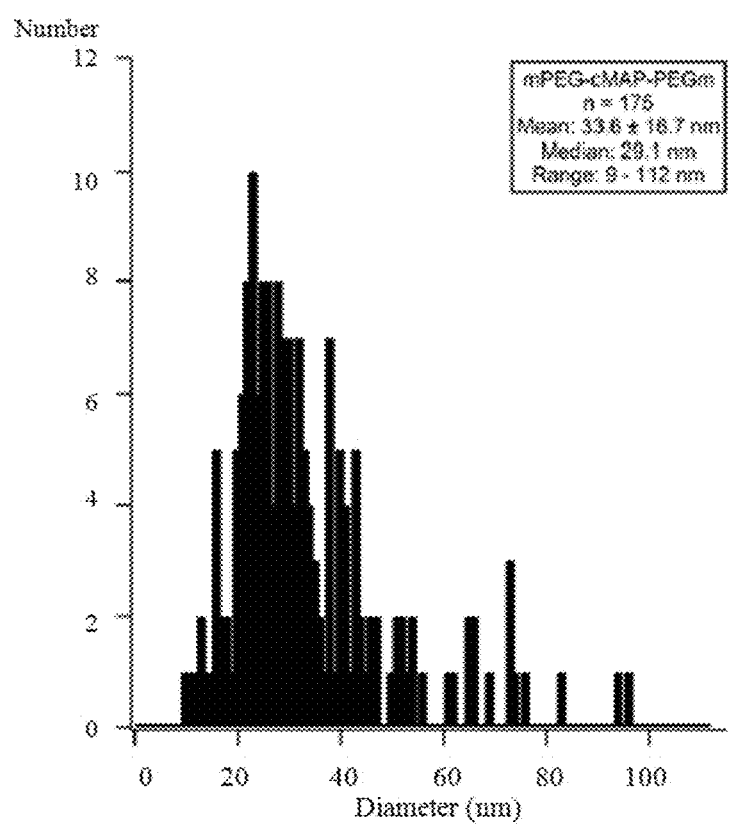
Figure 23E:
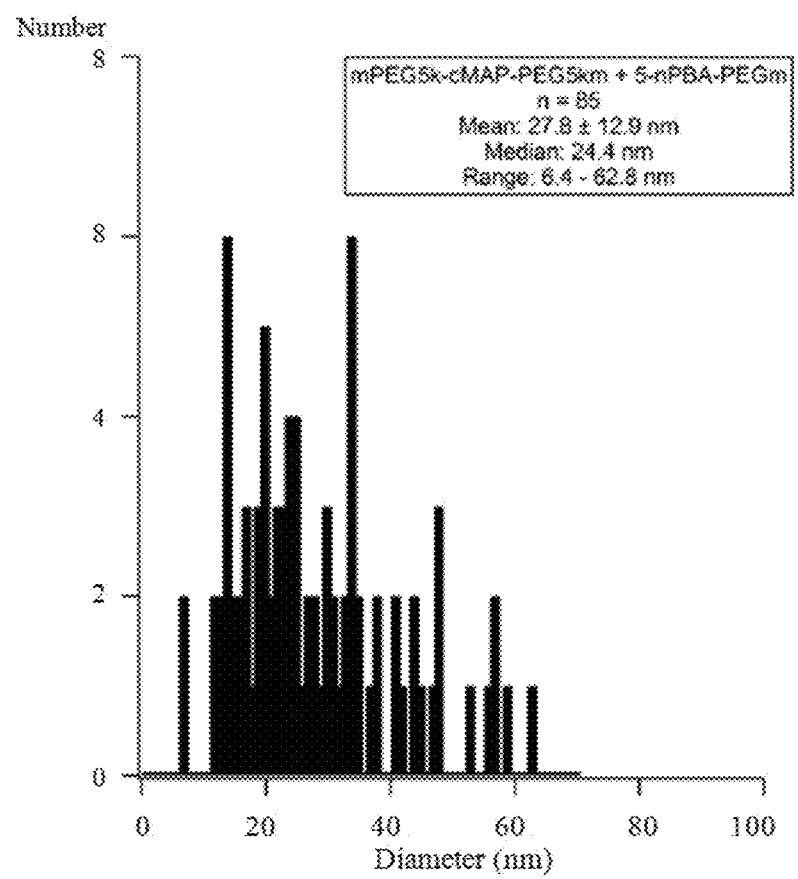

In contrast to cMAP alone, cMAP-PEG copolymer and mPEG-cMAP-PEGm triblock polymer were able to form stable particles without additional 5-nPBA-PEGm. However, the pure cMAP-PEG-cMAP triblock polymer isolated from the cMAP-PEG copolymer was not able to form stable siRNA-containing NPs without added 5-nPBA-PEGm, perhaps because it did not contain enough PEG to fully shield. and sterically stabilize the NP (Table 11 and FIGS. 18-20).

TABLE 11

NPs formed without extra 5-nPBA-PEGm using cMAP-PEG-cMAP triblock isolated from cMAP-PEG copolymer aggregates in 1X PBS, but is stable when at least one PEG per 2 diol groups is added to the formulation.

| Formulation | 10 mM phosphate buffer Avg. size (nm) | PBS Avg. size (nm) |
|---|---|---|
| 3.4k triblock, 1:1, 0 PEG | 176.6 ± 1.0 | aggregates |
| 3.4k triblock, 1:1, 0.5 PEG | 100.1 ± 0.8 | 57.9 ± 0.9 |
| 3.4k triblock, 1:1, 1 PEG | 149.5 ± 1.6 | 56.5 ± 1.5 |
| 3.4k triblock, 1:1, 2 PEG | 85.9 ± 2.0 | 74.5 ± 3.4 |
| 3.4k triblock, 3:1, 0 PEG | 392.3 ± 5.0 | aggregates |
| 3.4k triblock, 3:1, 0.5 PEG | 42.8 ± 2.0 | 47.3 ± 2.0 |
| 3.4k triblock, 3:1, 1 PEG | 61.3 ± 2.3 | 55.7 ± 1.2 |
| 3.4k triblock, 3:1, 2 PEG | 115.9 ± 11.4 | 96.6 ± 1.6 |
| 5k triblock, 1:1, 0 PEG | 165.2 ± 4.7 | aggregates |
| 5k triblock, 1:1, 0.5 PEG | 141.3 ± 5.2 | 99.8 ± 3.8 |
| 5k triblock, 1:1, 1 PEG | 109.2 ± 3.6 | 97.5 ± 4.2 |
| 5k triblock, 1:1, 2 PEG | 179.1 ± 19.9 | 143.5 ± 5.4 |

Although the cMAP-PEG copolymer and mPEG-cMAP-PEGm triblock polymer formed stable NPs in PBS. formulations with additional 5-nPBA-PEGm were also prepared to test whether the extra PEG offered greater steric stability to the NPs when tested in vivo. The amount of PEG bound to the NPs was approximately 20% (Table 13). The polymeric components of the NP were mixed together with an equal volume of siRNA to form NPs at concentrations of 0.8-1 mg siRNA/mL. Furthermore, the cMAP-PEG copolymer and mPEG-cMAP-PEGm triblock polymers were able to formulate stable NPs directly in PBS, eliminating the need to first formulate stable particles in a low salt buffer followed by addition of PBS (required by the cMAP).

Example 7.2, Nanoparticle Size

The sizes of the formulated NPs were characterized by dynamic light scattering (DLS) and cryo-transmission electron microscopy (CryoTEM). The diameters of these NPs are all ca. 30-40 nm as determined by both DLS and CryoTEM (Table 12). The NPs had a spherical morphology (CryoTEM imaging, shown in FIG. 21). Additional images and the distributions of sizes by both DLS and CryoTEM are reported in FIGS. 22 and 23.

TABLE 12

Size and surface charge of formulated nanoparticles.

| Formulation | Hydrodynamic Diameter by DLS (nm) | Diameter by CryoTEM (nm) | Zeta potential (mV) in 10 mM phosphate buffer, pH 7.4 | Zeta potential (mV) in 1 mM KCl, pH 5.5 |
|---|---|---|---|---|
| cMAP + 5-nPBA-PEG5km | 40.9 ± 8.9 | 29.3 ± 12.8 | −3.14 ± 0.56 | 0.76 ± 0.37 |
| cMAP-PEG5k copolymer | 25.1 ± 5.6 | 27.0 ± 7.9 | 0.69 ± 0.71 | 1.77 ± 0.76 |
| cMAP-PEG5k copolymer + 5-nPBA-PEG5km | 38.1 ± 15.3 | 34.4 ± 19.7 | −2.25 ± 0.64 | 0.70 ± 0.74 |
| mPEG5k-cMAP-PEG5km | 36.8 ± 20.2 | 33.6 ± 16.7 | 0.42 ± 0.73 | 0.40 ± 0.64 |
| mPEG5k-cMAP-PEG5km + 5-nPBA-PEG5km | 29.8 ± 9.2 | 27.8 ± 12.9 | −0.36 ± 0.64 | 1.44 ± 0.83 |

Example 7.3. Nanoparticle Zeta Potential

The zeta potential of the NPs (a measure of the NP surface charge), was measured in two solutions of different pH: 10 mM phosphate buffered at pH 7.4, when 5-nPBA-PEGm would be bound to the vicinal diols on cMAP; and 1 mM KCl at pH 5.5, when 5-nPBA-PEGm. would dissociate from the diols of the mucic acid. cMAP-siRNA NPs with 5-nPBA-mPEG had a slightly negative zeta potential at −3 mV in pH 7.4 phosphate buffer when 5-nPBA-mPEG was present on the NP. However, when these NPs were placed in 1 mM KCl at pH 5.5, the zeta potential was about +1 mV. These results were consistent with the boronic acid binding to diols on the mucic acid to form a tetrahedral boronate complex at pH 7.4 that shielded the positive charge on cMAP, and with the boronic acid dissociating from the NP at acidic pH 5.5. Similar effects were observed with the cMAP-PEG copolymer and mPEG-cMAP-PEGm triblock polymer with and without 5-11PBA-PEGm (Table 12).

Example 7.4. Nanoparticle Stoichiometry

The amount of cMAP and copolymers bound to the NPs is shown in Table 13. For all three polymers (cMAP, cMAP-PEG copolymer, and mPEG-cMAP-PEGm triblock polymer), approximately 33% of the total polymer used for formulation was bound for an effective NP charge ratio of 1+/−. The amount of 5-nPBA-PEGm present on the NP formulations containing excess PEG for stabilization is also shown in Table 13. The amount of 5-nPBA-PEGm bound to the cMAP+5-nPBA-PEGm NP was about 34%, or one PEG per diol (Table 13). About 20% of the PEG was found to be bound to the NP for the cMAP-PEG copolymer and the mPEG-cMAP-PEGm triblock polymer NP formulations. Considering the excess cationic polymer present when the particles were formulated at a 3+/− charge ratio and because the effective NP charge ratio is 1+/−, this meant that a little less than 1 PEG per diol was present on the NP. Virtually all of the siRNA was encapsulated in the NPs, as was shown above in the data on siRNA encapsulation (FIG. 12).

TABLE 13

Nanoparticle composition for NPs formulated at a charge ratio of 3+/−. Mean +/− S.E.M. of 3 runs (for PEG) or 2 runs (for polymer).

| Formulation | % 5-nPBA-PEGm bound to NP | % cationic polymer bound to NP |
|---|---|---|
| cMAP | N/A | 33.0 ± 0.2 |
| cMAP + 5-nPBA-PEG5km | 34.2 ± 8.7 | N/A |
| cMAP-PEG5k copolymer | N/A | 46.1 ± 1.3 |
| cMAP-PEG5k copolymer + 5-nPBA-PEG5km | 21.5 ± 1.7 | N/A |
| mPEG5k-cMAP-PEG5km | N/A | 34.4 ± 0.8 |
| mPEG5k-cMAP-PEG5km + 5-nPBA-PEG5km | 18.4 ± 4.5 | N/A |

Example 8. In Vivo Pharmacokinetic Studies in Mice

Stable formulations of NPs were tested in vivo via tail vein injection into Balb/c mice. At the doses injected, no toxicities were observed from any formulation. The PKs of the various NPs were measured, and the results are illustrated in FIGS. 24(A-C).

Figure 5:
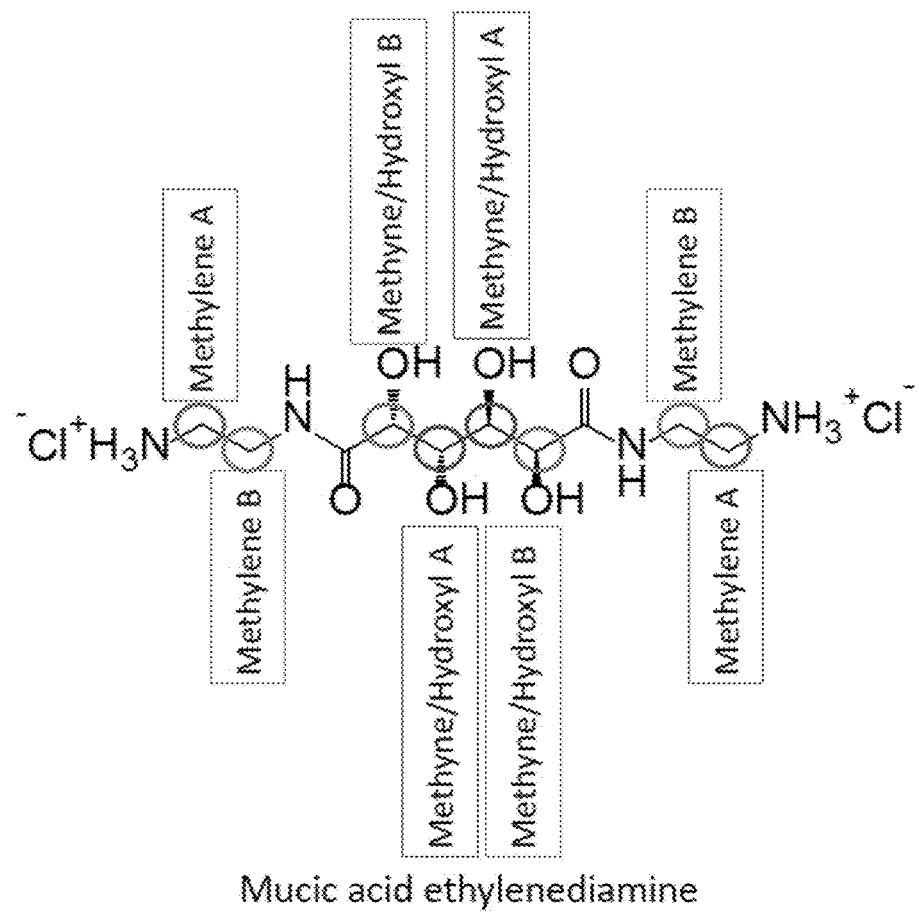
FIG. 5 shows the structure of Mucic Acid Ethylenediamine (see Table 1).

A NP composed of the cMAP polymer and siRNA mixed at a 3+/− charge ratio and stabilized with 5-nPBA-PEGm was tested, as this NP formulation was analogous to the CDP formulation that was used for clinical studies (CALAA-01). The cMAP-based NP has slightly longer circulation times than CALAA-01 (FIG. 5A). Because CALAA-01 used an inclusion complex for the interaction of CDP and adamantane-PEG (AD-PEG), the AD-PEG could detach from the NP during circulation to cause the NP to lose stability.

Figure 24A:
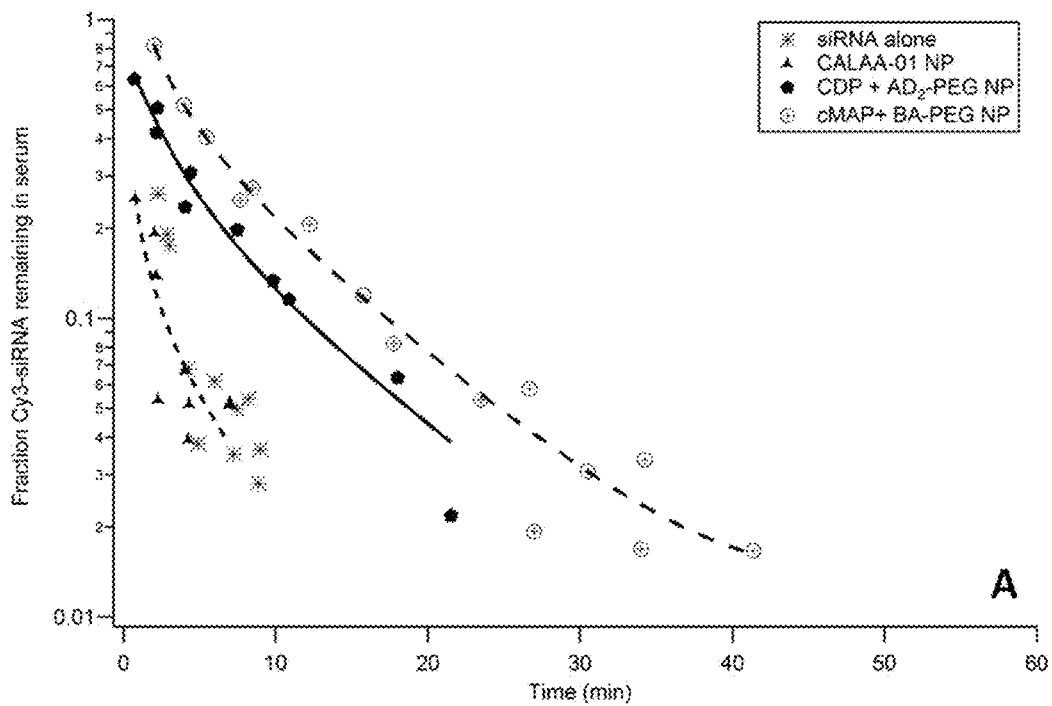
FIGS. 24A-C shows PK of formulated siRNA NPs compared to siRNA alone.

Others have synthesized AD2-PEG, and have shown that this compound has greater ability to stabilize CDP-based NPs than the AD-PEG in the original CALAA-01 formulation. This is believed to be due to the enhanced binding of the two adamantanes per PEG (into two CDs) that therefore results in more steric stabilization during circulation (FIG. 24A). With the present cMAP boronic acid system, the interaction between the PEG compound and the polymer is through a boronic acid ester that is formed from the boronic acid and diols on the polymer, with ca. 30% of the PEG bound to the NP. Because only ⅓ of the cMAP used to formulate the NP was bound to the particle (Table 3), this was roughly equivalent to one PEG present per diol. The boronic acid-diol interaction was expectedly stronger than the inclusion complex between adamantine and cyclodextrin, so that the 5-nPBA-PEGm was able to stay attached to cMAP longer than AD-PEG to CDP to result in greater steric stabilization and the improvement in circulation time.

Figure 24B:
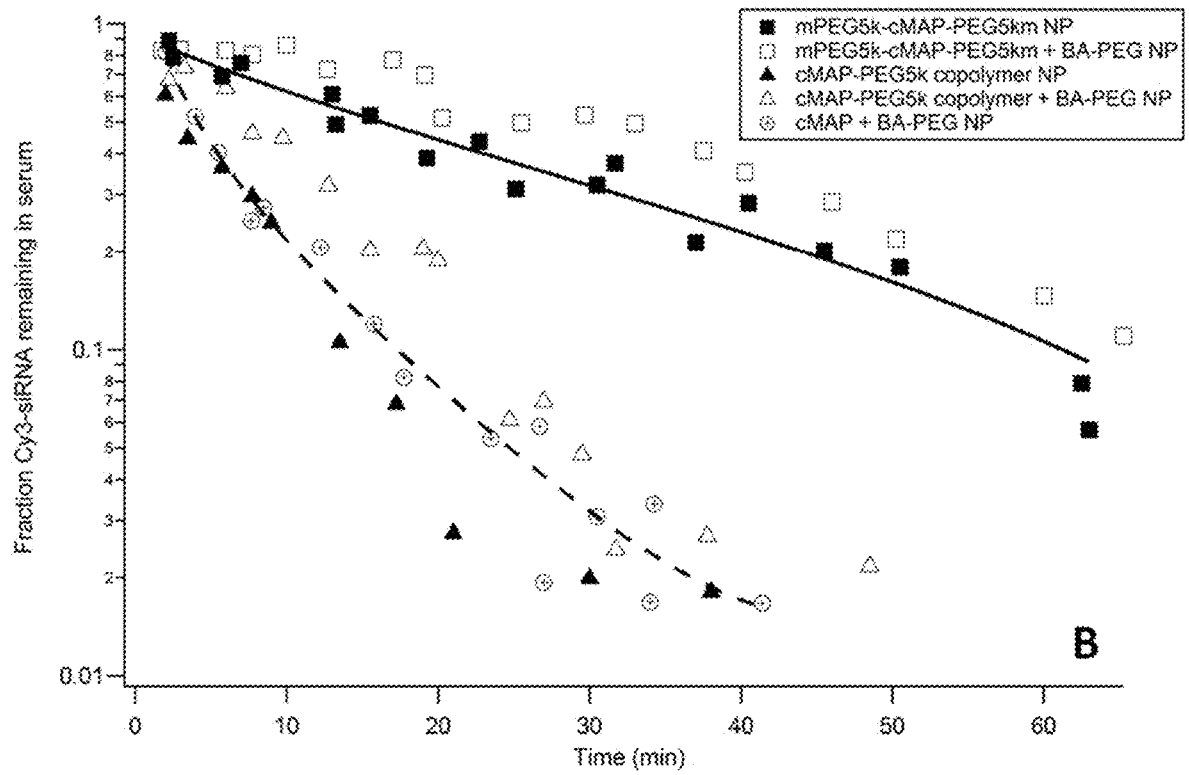

NPs formed using the cMAP-PEG copolymer can be stably formulated with siRNA in PBS at a 3+/− charge ratio into a NP without the use of 5-nPBA-mPEG (vide supra). The PEG in the cMAP-PEG copolymer is thought to form PEG loops to shield the NP core. Additional 5-nPBA-mPEG can be used for further stabilization of the NPs. The zeta potential switching from negative at pH 7.4 to positive at pH 5.5, in addition to the 20% PEG bound to the particles by measuring the amount of excess PEG filtered away, showed that the 5-nPBA-PEGm was able to interact with the cMAP-PEG copolymer in the NP formulations. The NPs formulated with cMAP-PEG copolymer did not provide for longer circulation times over the cMAP:5-nPBA-PEGm-based NPs whether or not 5-nPBA-PEGm is added (FIG. 24B).

Figure 24C:
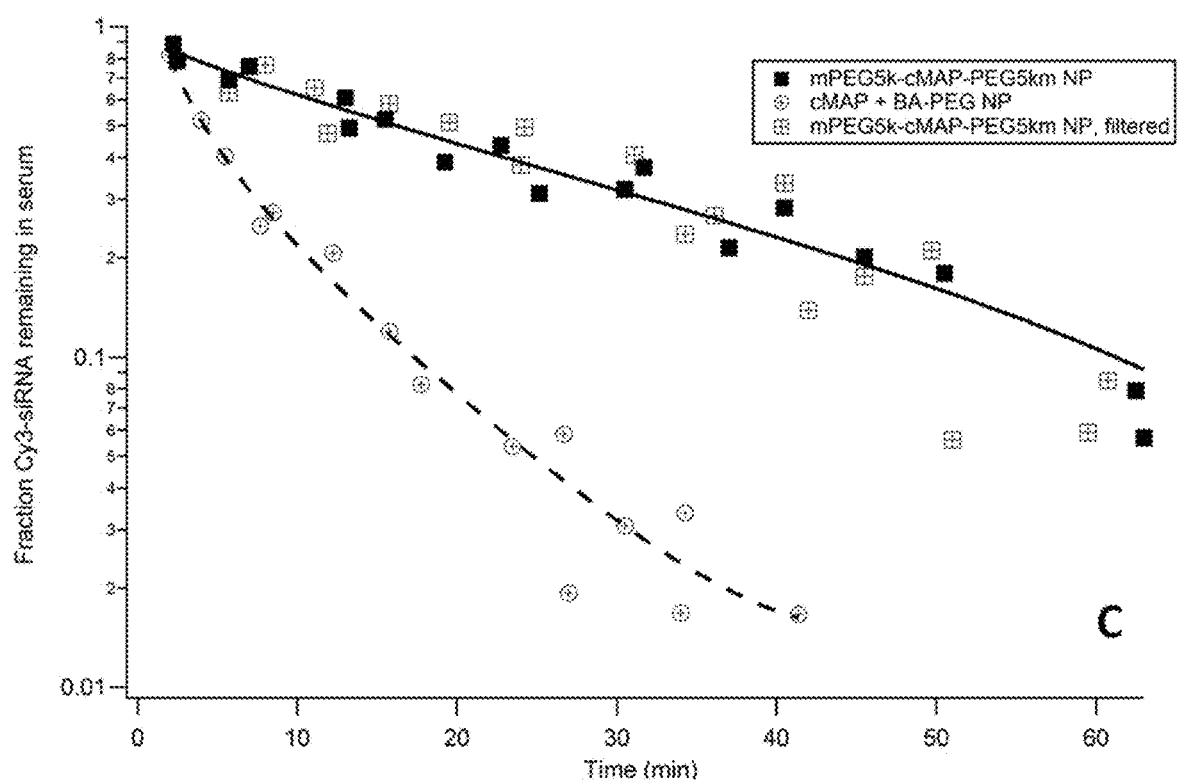
Figure 25:
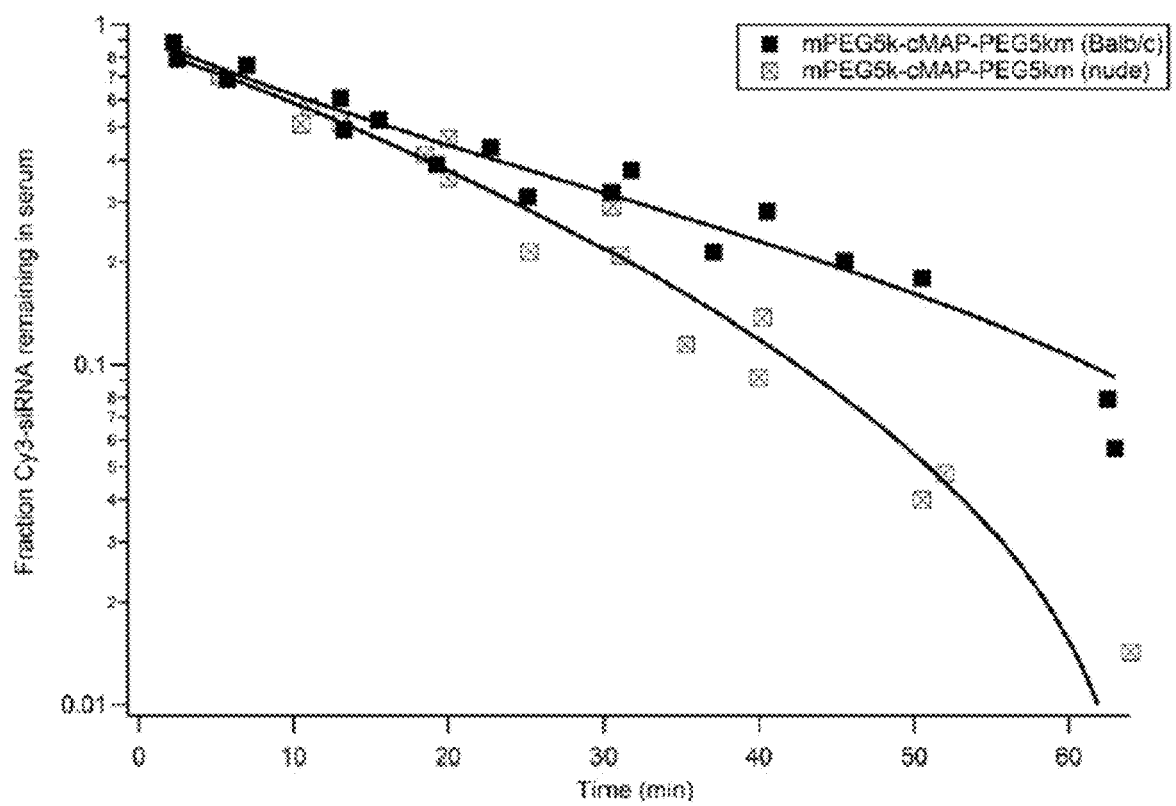
FIG. 25 shows data for the circulation time of the mPEG-cMAP-PEGm siRNA NP is similar in Balb/c and nude mice. n=3 mice. Fraction Cy3-siRNA remaining in serum as a function of time (to 60 min)

NPs formed using the mPEG-cMAP-PEGm triblock formed stable NPs in PBS (vide supra), and are believed to have a brush-like configuration of the PEG on the surface of the NPs. As shown by the data provided in FIG. 24B, injection of these NPs into mice resulted in an improved PK profile compared to all other cMAP-based NPs, with approximately 5-10% of the NPs remaining in mouse circulation after 60 minutes (other formulations were below the limit of detection by 60 minutes). Similar results are observed with this formulation in nude mice (FIG. 25). These longer circulation times are consistent with the NPs having a greater degree of steric stabilization presumably derived from a PEG polymer brush configuration on the surface of the NPs. The addition of 5-nPBA-PEGm to the triblock polymer-siRNA NP did not provide for improvements in the circulation time (FIG. 24B). Furthermore, a siRNA-containing NP formulation with a charge ratio of 2+/− that was obtained by removing some of the 66% excess triblock polymer from the 3+/− NP formulation by spin filtering the formulation with a 30 kD MWCO membrane did not result in a decrease in circulation time (FIG. 24C). Using this method of purification, it was difficult to remove all of the excess polymer. These results suggested that the polymer that was not contained within the NP did not alter the PK.

Of the polymer variations investigated here, the mPEG-cMAP-PEGm NP provided for the longest circulation time and the circulation time did not increase with additional bound 5-nPBA-PEGm. Although the 5-nPBA-PEGm interaction with the diols on cMAP were likely stronger than the interactions between adamantane and CDP, there was still likely to be some amount of PEG shedding from the NP. On the other hand, the triblock polymer, with 2 PEGs per cMAP unit, may have been able to achieve a PEG density on the NP surface required for a good brush layer. However, the amount of PEG covalently linked on this triblock polymer was less than that on the cMAP+5-nPBA-PEGm NP. The PK data from these systems suggested that the PEG shedding during circulation still occurred, but was less than what happens with the CDP-adamantane system. Some of the 5-nPBA-PEGm must be staying on the NPs during the circulation.

In order to provide further evidence that the NPs are remaining intact during circulation, serum collected from mice 20 minutes post-dosing was run on a gel and the siRNA visualized by either ethidium bromide or the fluorophore-tagged siRNA on a Typhoon imager. Results from these experiments showed that the siRNA and fluorescently tagged siRNA remain in intact NPs while circulating in vivo.

The following references may be useful in understanding certain aspects of the present disclosure:

1. Wu, S. Y., Lopez-Berestein, G., Calin, G. A. & Sood, A. K. (2014) RNAi Therapies: Drugging the Undruggable. *Science Transl. Med.* 6, 240ps7.
2. Kanasty, R., Dorkin, J. R., Vegas, A. & Anderson, D. (2013) Delivery materials for siRNA therapeutics. *Nat. Mater.* 12, 967-977.
3. Davis, M. E. (2009) The First Targeted Delivery of siRNA in Humans via a Self-Assembling Cyclodextrin Polymer-Based nanoparticle: From Concept to Clinic. *Mol. Pharm.* 6, 659-668.
4. Davis, M. E. et al. (2010) Evidence of RNAi in humans from systemically administered siRNA via targeted nanoparticles. *Nature* 464, 1067-1070.
5. Zuckerman, J. E. et al. (2014) Correlating animal and human phase Ia/Ib clinical data with CALAA-01, a targeted, polymer-based nanoparticle containing siRNA. *Proc. Natl. Acad. Sci. USA* 111, 11449-11454.
6. Zuckerman, J. E., Choi, C. H. J., Han, H., and Davis, M. E. (2012) Polycation-siRNA nanoparticles can disassemble at the kidney glomerular basement membrane. *Proc. Natl. Acad. Sci.* 109, 3137-3142.
7. Naeye, B., Deschout, H., Caveliers, V., Descamps, B., Braeckmans, K., Vanhove, C., Demeester, J., Lahoutte, T., De Smedt, S. C., Raemdonck, K. (2013) In vivo disassembly of IV administered siRNA matrix nanoparticles at the renal filtration barrier. *Biomaterials*, 34, 2350-2358.
8. Christie, R. J., Matsumoto, Y., Miyata, K., Nomoto, T., Fukushima, S., Osada, K., Hainaut, J., Pittella, F., Kim, H. J., Nishiyama, N., and Kataoka, K. (2012) Targeted polymeric micelles for siRNA treatment of experimental cancer by intravenous injection. *ACS Nano.*, 6, 5174-5189.
9. Nelson, C. E., Kintzing, J. R., Hanna, A., Shannon, J. M., Gupta, M. K., and Duvall, C. L. (2013) Balancing cationic and hydrophobic content of PEGylated siRNA polyplexes enhances endosome escape, stability, blood circulation time, and bioactivity in vivo. *ACS Nano.*, 7, 8870-8880.
10. Barrett, S. E., et al. (2014) Development of a liver-targeted siRNA delivery platform with a broad therapeutic window utilizing biodegradable polypeptide-based polymer conjugates. *Journal of Controlled Release*, 183, 124-137.
11. Gallas, A., Alexander, C., Davies, M. C., Puri, S., and Allen, S. (2012) Chemistry and formulations for siRNA therapeutics. *Chem. Soc. Rev.*, 42, 7983-7997.
12. Barros, S. A., and Gollob, J. A. (2012) Safety profile of RNAi nanomedicines. *Advanced Drug Delivery Reviews*, 64, 1730-1737.
13. Ballarin-Gonzalez, B. and Howard, K. A. (2012) Polycation-based nanoparticle delivery of RNAi therapeutics: Adverse effects and solutions. *Advanced Drug Delivery Reviews*, 64, 1717-1729.

14. Gomes-da-Silva, L. C., Simoes, S., Moreira, J. N. (2013) Challenging the future of siRNA therapeutics against cancer: the crucial role of nanotechnology. *Cell. Mol. Life. Sci.*, 71, 1417-1438.
15. Han, H. and Davis, M. E. (2013) Targeted nanoparticles assembled via complexation of boronic acid-containing targeting moieties to diol-containing polymers. *Bioconjugate Chem.* 24, 669-677.
16. Han, H. and Davis, M. E. (2013) Single-Antibody, Targeted Nanoparticle Delivery of Camptothecin. *Mol. Pharmaceutics* 10, 2558-2567.
17. Pun, S. H. and Davis, M. E. (2002) Development of a nonviral gene delivery vehicle for systemic application. *Bioconjugate Chem.* 13, 630-639.
18. Brissault, B., Leborgne, C., Scherman, D., Guis, C., and Kichler, A. (2011) Synthesis of poly(propylene glycol)-block-polyethylenimine tri block copolymers for the delivery of nucleic acids. *Macromol. Biosci.,* 11, 652-661.
19. Xue, L., Ingle, N. P., Reineke, T. M. (2013) Highlighting the role of polymer length, carbohydrate size, and nucleic acid type in potency of glycopolycation agents for pDNA and siRNA delivery. *Biomacromolecules,* 14, 3903-3915.
20. Yuthavong, Y., Feldman, N., and Boyer, P. (1975) Some chemical characteristics of dimethylsuberimidate and its effect on sarcoplasmic reticulum vesicles. *Biochimica et Biophysica Acta,* 382, 116-124.
21. Zhong, Z., Feijen, J., Lok, M. C., Hennink, W. E., Christensen, L. V., Yockman, J. W., Kim, Y.-H., and Kim, S. W. (2005) Low molecular weight linear polyethyleneimine-b-poly(ethylene glycol)-b-polyethyleneimine triblock copolymers: Synthesis, characterization, and in vitro gene transfer properties. *Biomacromolecules,* 6, 3440-3448.
22. Adeli, M., Ashiri, M., Chegeni, B. K., and Sasanpour, P. (2013) Tumor-targeted drug delivery systems based on supramolecular interactions between iron oxide-carbon nanotubes PAMAM-PEG-PAMAM linear-dendritic copolymers. *J. Iran. Chem. Soc.,* 10, 701-708.
23. Zhu, Y., Sheng, R., Luo, T., Li, H., Sun, W., Li, Y., and Cao, A. (2011) Amphiphilic cationic [dendritic poly(L-lysine)]-block-poly(L-lactide)-block-[dendritic poly(L-lysine)]s in aqueous solution: Self-aggregation and interaction with DNA as gene delivery carries. *Macromol. Biosci.,* 11, 174-186.
24. Sato, A., Choi, S. W., Hirai, M., Yamayoshi, A., Moriyama, R., Yamano, T., Takagi, M., Kano, A., Shimamoto, A., Maruyama, A. (2007) Polymer brush-stabilized polyplex for a siRNA carrier with long circulatory half-life. *Journal of Controlled Release,* 122, 209-216.
25. D'Addio, S. M., Saad, W., Ansell, S. M., Squiers, J. J., Adamson, D. H., Herrera-Alonso, M., Wohl, A. R., Hoye, T. R., Macosko, C. W., Mayer, L. D., Vauthier, C., and Prud'homme, R. K. (2012) Effects of block copolymer properties on nanocarrier protection from in vivo clearance. *Journal of Controlled Release,* 162, 208-217.
26. Han, H. Development of targeted, polymeric delivery vehicles for camptothecin and siRNA via boronic acid-diol complexation. Ph.D. Thesis, California Institute of Technology, Pasadena, Calif., 2012.
27. Eriksen, F. Relationship between in vitro stability and in vivo pharmacokinetic behavior of a polymeric gene delivery system. M. S. Thesis, ETH, Zurich, Switzerland, 2011.

As those skilled in the art will appreciate, numerous modifications and variations of the present disclosure are possible in light of these teachings, and all such are contemplated hereby. For example, in addition to the embodiments described herein, the present disclosure contemplates and claims those inventions resulting from the combination of features of the disclosure cited herein and those of the cited prior art references which complement the features of the present disclosure. Similarly, it will be appreciated that any described material, feature, or article may be used in combination with any other material, feature, or article, and such combinations are considered within the scope of this disclosure.

The disclosures of each patent, patent application, and publication cited or described in this document are hereby incorporated herein by reference, each in its entirety, for all purposes. In addition to the references already mentioned, the present disclosure contains subject matter related to U.S. patent application Ser. No. 12/540,319, filed Aug. 12, 2009, now U.S. Pat. No. 8,557,292; Ser. No. 13/782,458, filed Mar. 1, 2013; Ser. No. 13/782,486, filed Mar. 1, 2013; Ser. No. 13/852,303, filed: Mar. 28, 2013; and International Application No. PCT/US2009/053620, filed Aug. 12, 2009, the contents of which are incorporated by reference for all purposes, including their teachings of chemistries, applications, and methods of making and using the block copolymers described therein.

What is claimed:

1. A nanoparticle comprising a first polymer comprising alternating charged and uncharged segments comprising one or more of the following structural units of Formula (I) or Formula (III):

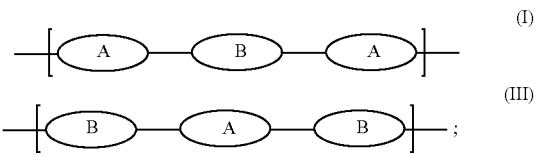

wherein
A is the uncharged segment comprising a polyalkylene glycol;
B is the charged segment comprising at least one cationic charged moiety and at least one polyhydroxy linkage comprising at least one pair of vicinal diols;
wherein the nanoparticle further comprises an encapsulated or covalently bound or linked biologically active agent; and
wherein the nanoparticle optionally comprises a polymer comprising a boronic acid-containing structure of Formula (X)

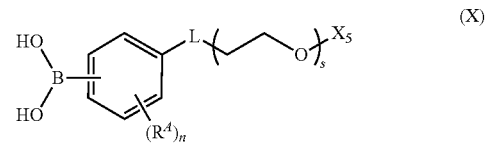

conjugated to the first polymer by a borate condensation linkage between the boronic acid moieties of Formula (X) and the at least one pair of vicinal diols of the polyhydroxy linkages of Formula (I) or (III), $X_5$ being at a distal end thereof;
$R^4$ is nitro;
n is 0, 1, 2, 3, or 4;
s is 20-1200;

L is NH—C(=O)—, —C(=O)—NH—, —O—C(=O)—, or C(=O)—O—; and $X_5$ is $C_{1-6}$ alkyl, optionally substituted with —OH, —COOH, —C(=O)O(alkyl), —C(=O)O(aryl), —NH$_2$, —NH(alkyl), —N(alkyl)$_2$, or a salt or protected analog thereof; and wherein if the nanoparticle comprises the polymer comprising the boronic acid-containing structure of Formula (X), the nanoparticle optionally further comprises a conjugated targeting ligand, wherein conjugation occurs through a condensation linkage between the conjugated boronic acid-containing polymer and the targeting ligand.

2. The nanoparticle of claim 1, wherein A comprises polyethylene glycol and an appropriate linking group, wherein the polyethylene glycol has a nominal weight in a range of from about 500 Daltons to about 50,000 Daltons.

3. The nanoparticle of claim 1, where B is a cationically charged segment comprising at least one mucic acid linkage comprising the at least one pair of vicinal diols and comprising at least one repeating subunit comprising a structure of Formula (IV):

(IV)

4. The nanoparticle of claim 1, where B is a cationically charged segment comprising at least one repeating subunit comprising a structure of Formula (V):

(V)

wherein m is 1, 2, 3, 4, 5, or 6.

5. The nanoparticle of claim 1, wherein B comprises at least one repeating subunit comprising cMAP, whose subunit structure is represented as Formula (VI):

(VI)

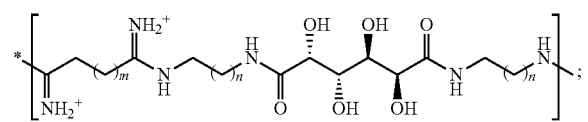

wherein
m is independently at each occurrence 1, 2, 3, 4, 5, 6, 7, 8, 9, or 10; and
n is independently at each occurrence 1, 2, 3, 4, or 5.

6. The nanoparticle of claim 1, described by a structure of Formula (VII):

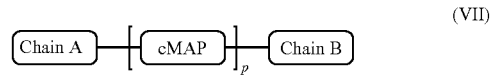

(VII)

wherein
Chain A is:

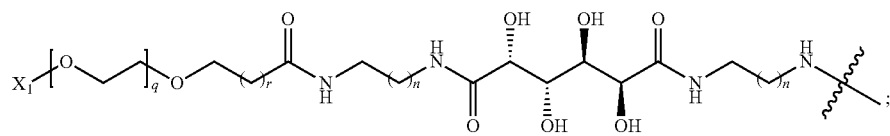

Chain B is:

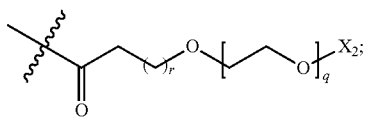

cMAP is:

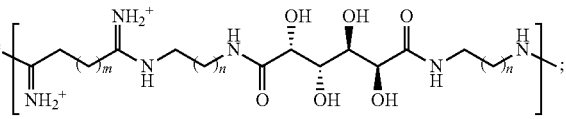

p and q are sufficient to provide a number average molecular weight for the subunits comprising cMAP and PEG, respectively, independently in a range of from 500 Da to 50,000 Da;

m is independently at each occurrence 1, 2, 3, 4, 5, 6, 7, 8, 9, or 10; and n is independently at each occurrence 1, 2, 3, 4, or 5; and $X_1$ and $X_2$ are independently at each occurrence $C_{1-4}$ alkyl, optionally substituted with —COOH, —C(=O)O(alkyl), —NH$_2$, —NH(alkyl), —N(alkyl)$_2$, or a salt or protected analog thereof.

7. The nanoparticle of claim 1, described by a structure of Formula (VII):

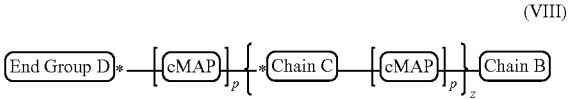

(VIII)

wherein
cMAP is:

[chemical structure]

Chain B is:

[chemical structure]

Chain C is:

[chemical structure]

End Group D is:

[chemical structure]

p and q are sufficient to provide a number average molecular weight for the subunits comprising cMAP and PEG, respectively, independently in a range of from 500 Da to 50,000 Da;

m is independently at each occurrence 1, 2, 3, 4, 5, 6, 7, 8, 9, or 10, preferably 4, 5, or 6;

n and r are independently at each occurrence 0, 1, 2, 3, 4, or 5, preferably 1, 2, or 3;

z is equal to or greater than 1 and up to 10; and $X_2$ is independently at each occurrence $C_{1-6}$ alkyl, optionally substituted with —OH, —COOH, —C(=O)O(alkyl), —NH$_2$, —NH(alkyl), —N(alkyl)$_2$, or a salt or protected analog thereof; and $X_3$ is —NH$_2$, —COOH, —C(=O)O(alkyl), or a salt or protected analog thereof.

8. The nanoparticle of claim 1, described by a structure of Formula (IX):

$$\text{[End Group D]}*\!-\!\!\left[\!\left[\text{cMAP}\right]_p\right]\!-\!*\!\left[\text{Chain C}\right]\!-\!\left[\text{cMAP}\right]_p\!\right]_z\!\!-\!X_4 \quad (\text{IX})$$

wherein
End Group D is:

[chemical structure]  or

-continued

[chemical structure];

cMAP is:

[chemical structure];

Chain C is:

[chemical structure];

p and q are sufficient to provide a number average molecular weight for the subunits comprising cMAP and PEG, respectively, independently in a range of from about 500 Da to about 50,000 Da;

m is independently at each occurrence 1, 2, 3, 4, 5, 6, 7, 8, 9, or 10;

n and r are independently at each occurrence 0, 1, 2, 3, 4, or 5;

z is equal to or greater than 1 and up to 10; and $X_3$ and $X_4$ are independently at each occurrence —NH$_2$, —COOH, —C(=O)O(alkyl), or a salt or protected analog thereof.

9. The nanoparticle of claim 1, wherein the biologically active agent is encapsulated.

10. The nanoparticle of claim 1, wherein the biologically active agent is covalently bound or linked to the nanoparticle.

11. The nanoparticle of claim 1, wherein the biologically active agent is a biologically active protein or enzyme.

12. The nanoparticle of claim 1, wherein the biologically active agent is a small molecule therapeutic agent.

13. The nanoparticle of claim 1, wherein the biologically active agent is a small molecule therapeutic that is covalently bound or linked to the nanoparticle, as a prodrug or through a biodegradable linkage.

14. The nanoparticle of claim 1, wherein the biologically active agent is an antibiotic, steroid, oligonucleotide, polynucleotide, plasmid, peptide, peptide fragment, or natural product therapeutic.

15. The nanoparticle of claim 1, wherein the biologically active agent is a chemotherapeutic epothilone, camptothecin-based drug, taxol, or nucleic acid.

16. The nanoparticle of claim 1, wherein the biologically active agent is a genomic DNA, cDNA, mRNA, siRNA, shRNA, miRNA, antisense oligonucleotide, virus, or chimeric polynucleotide.

17. The nanoparticle of claim 1, further comprising the polymer comprising the boronic acid-containing structure of Formula (X)

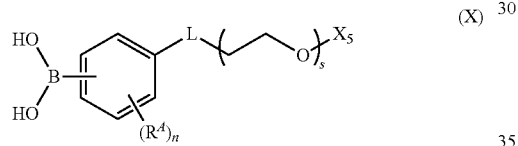
(X)

conjugated to the first polymer by a borate condensation linkage between the boronic acid moieties of Formula (X) and the at least one pair of vicinal diols of the polyhydroxy linkages of Formula (I) or (III), $X_5$ being at a distal end thereof;

$R^A$ is nitro;

n is 1;

s is 20-1200;

L is —NH—C(=O)—, —C(=O)—NH—, —O—C(=O)—, or —C(=O)—O—; and $X_5$ is $C_{1-6}$ alkyl, optionally substituted with —OH, —COOH, —C(=O)O(alkyl), —C(=O)O(aryl), —NH$_2$, —NH(alkyl), —N(alkyl)$_2$, or a salt or protected analog thereof.

18. The nanoparticle of claim 17, further comprising the conjugated targeting ligand, wherein conjugation occurs through the condensation linkage between the conjugated boronic acid-containing polymer and the targeting ligand.

19. The nanoparticle of claim 18, wherein the targeting ligand comprises an antibody, an aptamer, or a fragment of an antibody, a ligand for a cellular receptor, or a cellular receptor protein.

20. The nanoparticle of claim 18, wherein the targeting ligand comprises transferrin, or a fragment thereof.

21. An aqueous dispersion comprising a plurality of nanoparticles of claim 1, optionally wherein the nanoparticles are monodispersed and have a mean cross-sectional dimension in a range of from 20 nm to 300 nm with a standard deviation in cross-sectional dimension of less than 60%.

22. The aqueous dispersion of claim 21, wherein the nanoparticles are stable against aggregation when exposed to a 10 mM phosphate buffered saline solution at pH 7.4 or a 1 mM KCl solution at pH 5.5.

23. The aqueous dispersion of claim 22, wherein the nanoparticles comprise the polymer comprising the boronic acid-containing structure of Formula (X):

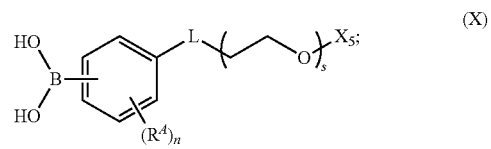
(X)

n is 1;

the at least one polyhydroxy linkage comprises mucic acid, and the molar ratio of the polymer comprising the boronic acid-containing structure of Formula (X) and the mucic acid is 0.5:1.

24. A method for making a controlled release pharmaceutical composition, the method comprising combining:
(a) a nanoparticle comprising a first polymer comprising alternating charged and uncharged segments comprising one or more of the following structural units of Formula (I) or Formula (III):

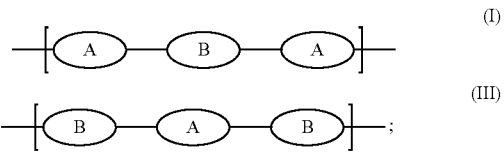

wherein
A is the uncharged segment comprising a polyalkylene glycol;
B is the charged segment comprising at least one cationic charged moiety and at least one polyhydroxy linkage comprising at least one pair of vicinal diols; and
(b) a biologically active agent;
wherein the combining results in the encapsulation or covalent binding or linking of the biologically active agent within or to the nanoparticle, respectively.

25. The method of claim 24, further comprising admixing the nanoparticle with a pharmaceutically acceptable vehicle, carrier or excipient.

26. The method of claim 24, wherein the biologically active agent is an antibiotic, enzyme, steroid, oligonucleotide, polynucleotide, plasmid, peptide, peptide fragment, protein, or a small molecule or natural product therapeutic.

* * * * *